US011370841B2

(12) United States Patent
Ling et al.

(10) Patent No.: US 11,370,841 B2
(45) Date of Patent: Jun. 28, 2022

(54) METHODS OF TREATING FIBROBLAST GROWTH FACTOR 19-MEDIATED CANCERS AND TUMORS

(71) Applicant: NGM Biopharmaceuticals, Inc., South San Francisco, CA (US)

(72) Inventors: Lei Ling, Foster City, CA (US); Hui Tian, Foster City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 13 days.

(21) Appl. No.: 16/327,756

(22) PCT Filed: Aug. 25, 2017

(86) PCT No.: PCT/US2017/048609
§ 371 (c)(1),
(2) Date: Feb. 22, 2019

(87) PCT Pub. No.: WO2018/039557
PCT Pub. Date: Mar. 1, 2018

(65) Prior Publication Data
US 2019/0194337 A1  Jun. 27, 2019

Related U.S. Application Data

(60) Provisional application No. 62/380,324, filed on Aug. 26, 2016.

(51) Int. Cl.
| C07K 16/24 | (2006.01) |
| A61K 39/395 | (2006.01) |
| A61K 31/14 | (2006.01) |
| C07K 16/28 | (2006.01) |
| A61K 31/519 | (2006.01) |
| A61P 35/00 | (2006.01) |
| A61K 9/00 | (2006.01) |
| C12Q 1/6851 | (2018.01) |
| C12Q 1/686 | (2018.01) |
| C12Q 1/6886 | (2018.01) |
| A61K 39/00 | (2006.01) |

(52) U.S. Cl.
CPC ........ C07K 16/2866 (2013.01); A61K 9/0019 (2013.01); A61K 31/14 (2013.01); A61K 31/519 (2013.01); A61K 39/395 (2013.01); A61K 39/3955 (2013.01); A61P 35/00 (2018.01); C12Q 1/686 (2013.01); C12Q 1/6851 (2013.01); C12Q 1/6886 (2013.01); A61K 2039/505 (2013.01); A61K 2039/844 (2018.08); G01N 2800/52 (2013.01)

(58) Field of Classification Search
None
See application file for complete search history.

(56) References Cited

U.S. PATENT DOCUMENTS

| 6,635,468 B2 | 10/2003 | Ashkenazi |
| 6,716,626 B1 | 4/2004 | Itoh |
| 6,806,352 B2 | 10/2004 | Desnoyers |
| 6,812,339 B1 | 11/2004 | Venter |
| 6,987,121 B2 | 1/2006 | Kliewer |
| 7,115,415 B2 | 10/2006 | Goddard |
| 7,129,072 B1 | 10/2006 | Schlessinger |
| 7,208,312 B1 | 4/2007 | Desnoyers |
| 7,259,248 B2 | 8/2007 | Itoh |
| 7,288,406 B2 | 10/2007 | Bogin |
| 7,390,879 B2 | 6/2008 | Ashkenazi |
| 7,459,540 B1 | 12/2008 | Thomason |
| 7,491,697 B2 | 2/2009 | Beals |
| 7,576,190 B2 | 8/2009 | Glaesner |
| 7,582,607 B2 | 9/2009 | Frye |
| 7,622,445 B2 | 11/2009 | Frye |
| 7,655,627 B2 | 2/2010 | Frye |
| 7,667,008 B2 | 2/2010 | Thomason |
| 7,705,195 B2 | 4/2010 | French |
| 7,723,297 B2 | 5/2010 | Itoh |
| 7,947,866 B2 | 5/2011 | Sparks |
| 8,012,931 B2 | 9/2011 | Cujec |
| 8,034,770 B2 | 10/2011 | Belouski |
| 8,188,040 B2 | 5/2012 | Belouski |
| 8,324,160 B2 | 12/2012 | Li |
| 8,361,963 B2 | 1/2013 | Belouski |
| 8,383,365 B2 | 2/2013 | Cujec |
| 8,410,051 B2 | 4/2013 | Belouski |
| 8,420,088 B2 | 4/2013 | Glass |
| 8,481,031 B2 | 7/2013 | Glass |

(Continued)

FOREIGN PATENT DOCUMENTS

| CN | 101591653 A | 12/2009 |
| CN | 102656266 A | 9/2012 |

(Continued)

OTHER PUBLICATIONS

Choudhari et al, Molecular Cancer Therapeutics, 2007; vol. 6, No. 1, pp. 112-121.*
Liu et al, The Journal of Biological Chemistry; 2010; vol. 285, No. 35, pp. 27429-27439.*
Jones et al, The Journal of Clinical Investigations; 2011; vol. 121; No. 9, pp. 3375-3383.*
Abe et al, World J Gastroenterology; Oct. 2017, vol. 23; No. 37, pp. 6833-6844.*
Angulo et al., "Liver Fibrosis, but No Other Histologic Features, Is Associated With Long-term Outcomes of Patients With Nonalcoholic Fatty Liver Disease," *Gastroenterology*, 149:389-397 (2015).

(Continued)

*Primary Examiner* — Bridget E Bunner
*Assistant Examiner* — Fozia M Hamud
(74) *Attorney, Agent, or Firm* — Jones Day

(57) ABSTRACT

Provided are methods of treating a FGF19-mediated cancer or tumor in a subject by administering to the subject an anti-IL-6 antibody or an anti-IL-6 receptor antibody or an inhibitor of STAT3/JAK signaling pathway, and pharmaceutical compositions relating thereto.

11 Claims, 36 Drawing Sheets

Specification includes a Sequence Listing.

(56) References Cited

U.S. PATENT DOCUMENTS

| | | |
|---|---|---|
| 8,535,912 B2 | 9/2013 | Sonoda |
| 8,541,369 B2 | 9/2013 | Dickinson |
| 8,580,936 B2 | 11/2013 | Williams |
| 8,618,053 B2 | 12/2013 | Belouski |
| 8,642,546 B2 | 2/2014 | Belouski |
| 8,673,860 B2 | 3/2014 | Schellenberger |
| 8,741,841 B2 | 6/2014 | Darling |
| 8,795,985 B2 | 8/2014 | Belouski |
| 8,802,697 B2 | 8/2014 | Bifulco |
| 8,809,499 B2 | 8/2014 | Fan |
| 8,835,385 B2 | 9/2014 | Belouski |
| 8,883,726 B2 | 11/2014 | Dickinson |
| 8,889,426 B2 | 11/2014 | Mohammadi |
| 8,889,621 B2 | 11/2014 | Mohammadi |
| 8,927,492 B2 | 1/2015 | Darling |
| 8,932,589 B2 | 1/2015 | Glass |
| 8,951,966 B2 | 2/2015 | Ling |
| 8,962,557 B2 | 2/2015 | Blaber |
| 8,975,223 B2 | 3/2015 | Vignati |
| 8,993,727 B2 | 3/2015 | Walker |
| 8,999,929 B2 | 4/2015 | Mohammadi |
| 9,006,400 B2 | 4/2015 | Boettcher |
| 9,023,791 B2 | 5/2015 | Boettcher et al. |
| 9,085,626 B2 | 7/2015 | Sonoda et al. |
| 9,089,525 B1 | 7/2015 | Ling |
| 9,273,107 B2 | 3/2016 | Ling |
| 9,290,557 B2 | 3/2016 | Ling |
| 9,474,785 B2 | 10/2016 | Mohammadi et al. |
| 9,475,856 B2 | 10/2016 | Mohammadi et al. |
| 9,550,820 B2 | 1/2017 | Mohammadi et al. |
| 9,580,483 B2 | 2/2017 | Ling |
| 9,670,260 B2 | 6/2017 | Ling |
| 9,751,924 B2 | 9/2017 | Ling |
| 9,789,160 B2 | 10/2017 | Wellstein |
| 9,878,008 B2 | 1/2018 | Ling |
| 9,878,009 B2 | 1/2018 | Ling |
| 9,889,177 B2 | 2/2018 | Ling |
| 9,889,178 B2 | 2/2018 | Ling |
| 9,895,416 B2 | 2/2018 | Ling |
| 9,925,242 B2 | 3/2018 | Ling |
| 9,926,356 B2 | 3/2018 | Mohammadi et al. |
| 9,963,494 B2 | 5/2018 | Ling |
| 9,974,833 B2 | 5/2018 | Ling |
| 10,174,090 B2 | 1/2019 | Mohammadi et al. |
| 10,369,199 B2 | 8/2019 | Ling |
| 10,398,758 B2 | 9/2019 | Ling et al. |
| 10,413,590 B2 | 9/2019 | Ling et al. |
| 10,434,144 B2 | 10/2019 | DePaoli et al. |
| 10,456,449 B2 | 10/2019 | Ling et al. |
| 10,517,929 B2 | 12/2019 | Lindhout et al. |
| 10,744,185 B2 | 8/2020 | Ling et al. |
| 2002/0012961 A1 | 1/2002 | Botstein |
| 2002/0042367 A1 | 4/2002 | Stewart |
| 2002/0082205 A1 | 6/2002 | Itoh |
| 2002/0151496 A1 | 10/2002 | Bringmann |
| 2002/0155543 A1 | 10/2002 | Adams |
| 2003/0045489 A1 | 3/2003 | Murphy |
| 2003/0065140 A1 | 4/2003 | Vernet |
| 2003/0105302 A1 | 6/2003 | Itoh |
| 2003/0113718 A1 | 6/2003 | Ashkenazi |
| 2003/0119112 A1 | 6/2003 | Baker |
| 2003/0125521 A1 | 7/2003 | Baker |
| 2003/0166051 A1 | 9/2003 | Desnoyers |
| 2003/0170822 A1 | 9/2003 | Itoh |
| 2003/0180890 A1 | 9/2003 | Conklin |
| 2003/0185846 A1 | 10/2003 | Ashkenazi |
| 2003/0220246 A1 | 11/2003 | Conklin |
| 2004/0014658 A1 | 1/2004 | Bogin |
| 2004/0126852 A1 | 7/2004 | Stewart |
| 2004/0146908 A1 | 7/2004 | Adams |
| 2004/0185494 A1 | 9/2004 | Itoh |
| 2005/0026243 A1 | 2/2005 | Stewart |
| 2005/0026832 A1 | 2/2005 | Adams |
| 2005/0107475 A1 | 5/2005 | Jones |
| 2005/0153305 A1 | 7/2005 | Vernet |
| 2005/0181375 A1 | 8/2005 | Aziz |
| 2005/0196842 A1 | 9/2005 | Botstein |
| 2005/0250684 A1 | 11/2005 | Heuer |
| 2006/0160181 A1 | 7/2006 | Luethy |
| 2006/0172386 A1 | 8/2006 | Itoh |
| 2006/0246540 A1 | 11/2006 | Ashkenazi |
| 2006/0275794 A1 | 12/2006 | Carrino |
| 2006/0281679 A1 | 12/2006 | Itoh |
| 2007/0037165 A1 | 2/2007 | Venter |
| 2007/0042395 A1 | 2/2007 | Botstein |
| 2007/0077626 A1 | 4/2007 | Botstein |
| 2007/0238657 A1 | 10/2007 | Itoh |
| 2007/0253966 A1 | 11/2007 | Glaesner |
| 2008/0057076 A1 | 3/2008 | Bringmann |
| 2008/0124759 A1 | 5/2008 | Conklin |
| 2009/0081658 A1 | 3/2009 | Belouchi |
| 2009/0098603 A1 | 4/2009 | Botstein |
| 2009/0196876 A1 | 8/2009 | Sparks |
| 2009/0226459 A1 | 9/2009 | Powers |
| 2009/0312265 A1 | 12/2009 | Schmidtchen |
| 2010/0055730 A1 | 3/2010 | Usheva-Simidjiyska |
| 2010/0215657 A1 | 8/2010 | Glass |
| 2010/0239554 A1 | 9/2010 | Schellenberger |
| 2010/0240587 A1 | 9/2010 | Schlein |
| 2010/0323954 A1 | 12/2010 | Li |
| 2011/0015345 A1 | 1/2011 | Pinkstaff |
| 2011/0053787 A1 | 3/2011 | Brulliard |
| 2011/0104152 A1 | 5/2011 | Sonoda |
| 2011/0107439 A1 | 5/2011 | De Wit |
| 2011/0135657 A1 | 6/2011 | Hu |
| 2011/0150903 A1 | 6/2011 | Baurin |
| 2011/0195077 A1 | 8/2011 | Glass |
| 2011/0195895 A1 | 8/2011 | Walker |
| 2011/0207912 A1 | 8/2011 | Botstein |
| 2011/0268794 A1 | 11/2011 | Camilleri |
| 2011/0306129 A1 | 12/2011 | Nistor |
| 2011/0312881 A1 | 12/2011 | Silverman |
| 2012/0003216 A1 | 1/2012 | Belouski |
| 2012/0064544 A1 | 3/2012 | Econs |
| 2012/0157397 A1 | 6/2012 | Hazen |
| 2013/0004492 A1 | 1/2013 | Marshall |
| 2013/0023474 A1 | 1/2013 | Ling |
| 2013/0116171 A1 | 5/2013 | Jonker |
| 2013/0122004 A1 | 5/2013 | Glass |
| 2013/0143796 A1 | 6/2013 | Li |
| 2013/0172275 A1 | 7/2013 | Mohammadi |
| 2013/0183294 A1 | 7/2013 | Pai |
| 2013/0183319 A1 | 7/2013 | Bange |
| 2013/0184211 A1 | 7/2013 | Mohammadi |
| 2013/0231277 A1 | 9/2013 | Mohammadi |
| 2013/0324458 A1 | 12/2013 | Glass |
| 2013/0324701 A1 | 12/2013 | Williams |
| 2013/0331317 A1 | 12/2013 | Mohammadi |
| 2013/0331325 A1 | 12/2013 | Mohammadi |
| 2014/0094406 A1 | 4/2014 | Mohammadi |
| 2014/0148388 A1 | 5/2014 | Sonoda |
| 2014/0155316 A1 | 6/2014 | Mohammadi |
| 2014/0189893 A1 | 7/2014 | Li |
| 2014/0194352 A1 | 7/2014 | Ling |
| 2014/0243260 A1 | 8/2014 | Mohammadi |
| 2014/0243266 A1 | 8/2014 | Ling |
| 2014/0294820 A1 | 10/2014 | Faul et al. |
| 2015/0079065 A1 | 3/2015 | Wolf |
| 2015/0111821 A1 | 4/2015 | Suh |
| 2015/0132309 A1 | 5/2015 | Desnoyers |
| 2015/0284442 A1 | 10/2015 | Ling |
| 2015/0291677 A1 | 10/2015 | Ling |
| 2016/0045565 A1 | 2/2016 | Ling |
| 2016/0166642 A1 | 6/2016 | Ling |
| 2016/0168215 A1 | 6/2016 | Ling |
| 2016/0168216 A1 | 6/2016 | Ling |
| 2016/0168217 A1 | 6/2016 | Ling |
| 2016/0168218 A1 | 6/2016 | Ling |
| 2016/0168219 A1 | 6/2016 | Ling |
| 2016/0168220 A1 | 6/2016 | Ling |
| 2016/0168221 A1 | 6/2016 | Ling |
| 2016/0168222 A1 | 6/2016 | Ling |
| 2016/0200788 A1 | 7/2016 | Ling |
| 2016/0223568 A1 | 8/2016 | Genovese et al. |

(56) References Cited

U.S. PATENT DOCUMENTS

| | | |
|---|---|---|
| 2016/0252497 A1 | 9/2016 | Ling |
| 2017/0173114 A1 | 6/2017 | Kahn et al. |
| 2017/0182122 A1 | 6/2017 | Ling |
| 2017/0182123 A1 | 6/2017 | Ling |
| 2017/0232067 A1 | 8/2017 | Lindhout |
| 2017/0327551 A1 | 11/2017 | Ling |
| 2018/0079806 A1 | 3/2018 | Sonoda |
| 2018/0100018 A1 | 4/2018 | Sonoda et al. |
| 2018/0110834 A1 | 4/2018 | DePaoli |
| 2018/0177846 A1 | 6/2018 | Ling |
| 2018/0186850 A1 | 7/2018 | Mohammadi et al. |
| 2018/0208677 A1 | 7/2018 | Desnoyers |
| 2018/0280479 A1 | 10/2018 | Choi et al. |
| 2018/0318390 A1 | 11/2018 | Ling |
| 2018/0340028 A1 | 11/2018 | Rajan |
| 2018/0355007 A1 | 12/2018 | Ling |
| 2018/0362605 A1 | 12/2018 | Ling |
| 2018/0369331 A1 | 12/2018 | Fouillous-Meugnier et al. |
| 2019/0060403 A1 | 2/2019 | Ling |
| 2019/0175692 A1 | 6/2019 | Ling |
| 2019/0175693 A1 | 6/2019 | Ling |
| 2019/0175694 A1 | 6/2019 | Ling |
| 2019/0175695 A1 | 6/2019 | Ling |
| 2019/0175696 A1 | 6/2019 | Ling |
| 2019/0175697 A1 | 6/2019 | Ling |
| 2019/0177384 A1 | 6/2019 | Ling et al. |
| 2019/0194337 A1 | 6/2019 | Ling et al. |
| 2019/0307847 A1 | 10/2019 | Ling |
| 2020/0054714 A1 | 2/2020 | Ling et al. |
| 2020/0164035 A1 | 5/2020 | Ling |
| 2020/0164036 A1 | 5/2020 | DePaoli et al. |
| 2020/0197489 A1 | 6/2020 | Ling et al. |
| 2020/0197490 A1 | 6/2020 | Lindhout et al. |
| 2020/0330555 A1 | 10/2020 | Rossi et al. |
| 2020/0390858 A1 | 12/2020 | DePaoli et al. |
| 2020/0390859 A1 | 12/2020 | Ling et al. |

FOREIGN PATENT DOCUMENTS

| | | |
|---|---|---|
| CN | 103127503 A | 6/2013 |
| DE | 10100588 | 7/2002 |
| DE | 10100587 | 11/2002 |
| EA | 201001204 A1 | 2/2011 |
| EA | 015363 B1 | 6/2011 |
| EP | 2163626 | 3/2010 |
| JP | 2002112772 | 4/2002 |
| JP | 2009039117 | 2/2009 |
| JP | 2012530493 | 12/2012 |
| JP | 2013194049 | 9/2013 |
| KR | 10-2012-0095392 A | 8/2012 |
| NZ | 602702 | 3/2014 |
| WO | WO 2000/060085 | 10/2000 |
| WO | WO 2001/018209 | 3/2001 |
| WO | WO 2001/049740 | 7/2001 |
| WO | WO 2001/049849 | 7/2001 |
| WO | WO 2001/061007 | 8/2001 |
| WO | WO 2002/036732 | 5/2002 |
| WO | WO 2002/041911 | 5/2002 |
| WO | WO 2002/055693 | 7/2002 |
| WO | WO 2003/080803 | 10/2003 |
| WO | WO 2004/026228 | 4/2004 |
| WO | WO 2004/063355 | 7/2004 |
| WO | WO 2006/004076 | 1/2006 |
| WO | WO 2006/048291 | 5/2006 |
| WO | WO 2006/049854 | 5/2006 |
| WO | WO 2008/021196 | 2/2008 |
| WO | WO 2008/030273 | 3/2008 |
| WO | WO 2009/076478 | 6/2009 |
| WO | WO 2009/090553 | 7/2009 |
| WO | WO 2009/095372 | 8/2009 |
| WO | WO 2009/116861 | 9/2009 |
| WO | WO 2009/155381 | 12/2009 |
| WO | WO 2010/004204 | 1/2010 |
| WO | WO 2010/006214 | 1/2010 |
| WO | WO 2010/042747 | 4/2010 |
| WO | WO 2010/065439 | 6/2010 |
| WO | WO 2010/080976 | 7/2010 |
| WO | WO 2010/083051 | 7/2010 |
| WO | WO 2010/129600 | 11/2010 |
| WO | WO 2010/139741 | 12/2010 |
| WO | WO 2010/142665 | 12/2010 |
| WO | WO 2010/148142 | 12/2010 |
| WO | WO 2011/047267 | 4/2011 |
| WO | WO 2011/071783 | 6/2011 |
| WO | WO 2011/084808 | 7/2011 |
| WO | WO 2011/089203 | 7/2011 |
| WO | WO 2011/092234 | 8/2011 |
| WO | WO 2011/130417 | 10/2011 |
| WO | WO 2011/130729 | 10/2011 |
| WO | WO 2011/154349 | 12/2011 |
| WO | WO 2012/010553 | 1/2012 |
| WO | WO 2012/031603 | 3/2012 |
| WO | WO 2012/062078 | 5/2012 |
| WO | WO 2012/066075 | 5/2012 |
| WO | WO 2012/086809 | 6/2012 |
| WO | WO 2012/138919 | 10/2012 |
| WO | WO 2012/140650 | 10/2012 |
| WO | WO 2012/154263 | 11/2012 |
| WO | WO 2012/158704 | 11/2012 |
| WO | WO 2012/170438 | 12/2012 |
| WO | WO 2012/170704 | 12/2012 |
| WO | WO 2012/177481 | 12/2012 |
| WO | WO 2013/006486 | 1/2013 |
| WO | WO 2013/010780 | 1/2013 |
| WO | WO 2013/027191 | 2/2013 |
| WO | WO 2013/033452 | 3/2013 |
| WO | WO 2013/049234 | 4/2013 |
| WO | WO 2013/109856 | 7/2013 |
| WO | WO 2013/131091 | 9/2013 |
| WO | WO 2013/151671 | 10/2013 |
| WO | WO 2013/173158 | 11/2013 |
| WO | WO 2013/18495 8 | 12/2013 |
| WO | WO 2013/184960 | 12/2013 |
| WO | WO 2013/184962 | 12/2013 |
| WO | WO 2013/188182 | 12/2013 |
| WO | WO 2014/031420 | 2/2014 |
| WO | WO 2014/037373 | 3/2014 |
| WO | WO 2014/085365 | 6/2014 |
| WO | WO 2014/105939 | 7/2014 |
| WO | WO 2014/130659 | 8/2014 |
| WO | WO 2014/149699 | 9/2014 |
| WO | WO 2014/152089 | 9/2014 |
| WO | WO 2014/152090 | 9/2014 |
| WO | WO 2015/065897 | 5/2015 |
| WO | WO 2015/112886 | 7/2015 |
| WO | WO 2015/183890 | 12/2015 |
| WO | WO 2015/195509 | 12/2015 |
| WO | WO 2016/048995 | 3/2016 |
| WO | WO 2016/065106 | 4/2016 |
| WO | WO 2016/073855 | 5/2016 |
| WO | WO 2017/083276 | 5/2017 |
| WO | WO 2018/039557 | 3/2018 |
| WO | WO 2018/044778 | 3/2018 |
| WO | WO 2018/171557 | 9/2018 |
| WO | WO 2018/195390 | 10/2018 |
| WO | WO 2019/010314 | 1/2019 |
| WO | WO 2019/195514 A1 | 10/2019 |
| WO | WO 2020/176703 | 9/2020 |
| WO | WO 2020/214753 | 10/2020 |

OTHER PUBLICATIONS

Aranha et al., "Bile acid levels are increased in the liver of patients with steatohepatitis," *Eur. J. Gastroenterol. Hepatol.*, 20(6):519-525 (2008).

Beenken et al., "The FGF family: biology, pathophysiology and therapy," *Nat. Rev. Drug Discov.*, 8:235-253 (2009).

Beuers et al., "Medical treatment of primary sclerosing cholangitis: a role for novel bile acids and other (post-) transcriptional modulators?," *Clin. Rev. Allergy Immunol.*, 36(1):52-61 (2009).

Bromberg et al., "Stat3 as an oncogene," *Cell*, 98:295-303 (1999).

Calvisi et al., "Ubiquitous activation of Ras and Jak/Stat pathways in human HCC," *Gastroenterol.*, 130:1117-1128 (2006).

(56) References Cited

OTHER PUBLICATIONS

Camiileri et al., "Measurement of Serum 7α-hydroxy-4-cholesten-3-one (or 7αC4), a Surrogate Test for Bile Acid Malabsorption in Health, Ileal Disease and Irritable Bowel Syndrome using Liquid Chromatography-Tandom Mass Spectrometry," *Neurogastroenterol Motil.*, 21(7):734-e43 (2009).
Camiileri et al., "Effect of increased bile acid synthesis or fecal excretion in irritable bowel syndrome-diarrhea," *Am. J. Gastroenterol.*, 109:1621-1630 (2014).
Chazouilleres, "Primary sclerosing cholangitis and bile acids," *Clinics and Research in Hepatology and Gastroenterology*, 36:S21-S25 (2012).
Chen et al., "Soluble FGFR4 extracellular domain inhibits FGF19-induced activation of FGFR4 signaling and prevents nonalcoholic fatty liver disease," *Biochem. Biophys. Res. Comm.*, 409:651-656 (2011).
Chen et al., "Sorafenib overcomes TRAIL resistance of hepatocellular carcinoma cells through the inhibition of STAT3," *Clin. Cancer Res.*, 16:5189-5199 (2010).
Claudel et al., "Role of Nuclear Receptors for Ble Acid Metabolism, Bile Secretion, Cholestasis, and Gallstone Disease," *Biochim. Biophys. Acta*, 1812:867-878 (2011).
Depaoli et al., "NGM313, a novel activator of beta-Klotho/FGFR1c: A single dose significantly reduces steatosis (liver fat by MRI-PDFF), inflammation (ALT, AST) and fibrogenic activity (Pro-C3) in NAFLD subjects," Presentation at EASL International Liver Congress, Vienna, Austria, Apr. 12, 2019, 16 pages.
Depaoli et al., "NGM313, a novel activator of beta-Klotho/FGFR1c: A single dose significantly reduces steatosis (liver fat by MRI-PDFF), inflammation (ALT, AST) and fibrogenic activity (Pro-C3) in NAFLD subjects," Abstract 4579, EASL International Liver Congress, Vienna, Austria, Apr. 12, 2019, 3 pages.
Desnoyers et al., "Targeting FGF19 inhibits tumor growth in colon cancer xenograft and FGF19 transgenic hepatocellular carcinoma models," *Oncogene*, 27:85-97 (2008).
Dichenko et al., "Sat-374: Steroid 7 Alpha-Hydroxylases: Neurosteroids Activation and Cholesterol Catabolism," The Endocrine Society's 95th Annual Meeting and Expo, San Francisco, Abstract, Jun. 15-18, 2013.
Ďurovcova et al., "Plasma Concentration of Fibroblast Growth Factors 21 and 19 in Patients with Cushing's Syndrome," *Physiol. Res.*, 59:415-422 (2010).
Foltz et al., "Treating Diabetes and Obesity with an FGF21-Mimetic Antibody Activating the βKlotho/FGFR1c Receptor Complex," *Sci. Transl. Med.*, 4:162ra153, pp. 1-10 (2012).
Foltz et al., "Supplementary Materials For: Treating Diabetes and Obesity with an FGF21-Mimetic Antibody Activating the βKlotho/FGFR1c Receptor Complex," *Sci. Transl. Med.*, 4:162ra153, pp. 1-13 (2012).
Frankel et al., "Characterization of diphtheria fusion proteins targeted to the human interleukin-3 receptor," *Protein Eng.*, 13(8):575-581 (2000).
French et al., "Targeting FGFR4 Inhibits Hepatocellular Carcinoma in Preclinical Mouse Models," *PLoS One*, 7(5):e36713 (2012).
Galman et al., "Monitoring hepatic cholesterol 7α-hydroxylase activity by assay of the stable bile acid intermediate 7α-hydroxy-4-cholesten-3-one in peripheral blood," *J. Lipid Res.*, 44:859-866 (2003).
Ge et al., "Characterization of a FGF19 Variant with Altered Receptor Specificity Revealed a Central Role for FGFR1c in the Regulation of Glucose Metabolism," *PLoS One*, 7(3):e33603 (2012).
Harmer et al., "The Crystal Structure of Fibroblast Growth Factor (FGF) 19 Reveals Novel Features of the FGF Family and Offers a Structural Basis for Its Unusual Receptor Affinity," *Biochemistry*, 43:629-640 (2004).
Harrison et al., "NGM282 Improves Liver Fibrosis and Histology in 12 Weeks in Patients With Nonalcoholic Steatohepatitis," *Hepatology*, 1-15 (2019).
Harrison et al., "NGM282 in NASH: 3 mg vs 6 mg QD (phase 2)," *Lancet*, 391:1174-1185 (2018).
Hasegawa, "The expansion of PROMININ-1-positive epithelial-mesenchymal cells within periportal fibrosis of rotavirusinduced biliary atresia," *Hepatol.*, 58:802A (2013).
He et al., "NF-κB and STAT3—key players in liver inflammation and cancer," *Cell Res.*, 21:159-168 (2011).
He et al., "Hepatocyte IKKbeta/NF-kappaB inhibits tumor promotion and progression by preventing oxidative stress-driven STAT3 activation," *Cancer Cell*, 17:286-297 (2010).
He et al., "Identification of liver cancer progenitors whose malignant progression depends on autocrine IL-6 signaling," *Cell*, 155:384-396 (2013).
Hirschfield et al., "Effect of NGM282, an FGF19 analogue, in primary sclerosing cholangitis: A multicenter, randomized, double-blind, placebo-controlled phase II trial," *J. Hepatology*, European Association for the Study of the Liver, pp. 1-12, 2018.
Hirschfield et al., "Serum Bile Acids Significantly Associate with the Fibrogenesis Biomarker Pro-C3: Analysis of a Randomized, Placebo-Controlled Trial of NGM282 in Patients with Primary Sclerosing Cholangitis (PSC)," NGM Biopharmaceuticals Inc. Poster, European Association for the Study of the Liver (EASL), International Liver Congress, Apr. 11, 2019.
Hofmann et al., "Chronic diarrhea due to excessive bile acid synthesis and not defective ileal transport: A new syndrome of defective FGF19 release," *Clin Gastroenterol Hepatol.*, 7(11):1151-1154 (2009).
Holt et al., "Definition of a novel growth factor-dependent signal cascade for the suppression of bile acid biosynthesis," *Genes Dev.*, 17:1581-1591 (2003).
Ikeda et al., "Leptin receptor somatic mutations are frequent in HCV-infected cirrhotic liver and associated with hepatocellular carcinoma," *Gastroenterol.*, 146:222-232 (2014).
Inagaki et al., "Fibroblast Growth Factor 15 Functions as an Enterohepatic Signal to Regulate Bile Acid Homeostasis," *Cell Metabolism*, 2:217-225 (2005).
Islam et al., "Bile Acids: An Underrecognized and Underappreciated Cause of Chronic Diarrhea," *Pract. Gastroenterol.*, 110:32-44 (2012).
Kakumu et al., "Interleukin 6 production by peripheral blood mononuclear cells in patients with chronic hepatitis B virus infection and primary biliary cirrhosis," *Gastroenterologia Japonica*, 28:18-24 (1993).
Karras et al., "STAT3 regulates the growth and immunoglobulin production of BCL(1) B cell lymphoma through control of cell cycle progression," *Cellular immunol.*, 202:124-135 (2000).
Kaushik et al., "Why is Trehalose an Exceptional Protein Stabilizer?," *J. Biol. Chem.*, 278(29):26458-26465 (2003).
Kenakin et al., "Signalling bias in new drug discovery: detection, quantification and therapeutic impact," *Nat. Rev. Drug Discov.*, 12:205-521 (2013).
Kir et al., "Roles of FGF19 in Liver Metabolism," *Cold Spring Harb. Symp. Quant. Biol.*, 76:139-144 (2011).
Kovar et al., "Regulation of Diurnal Variation of Cholesterol 7α-hydroxylase (CYP7A1) Activity in Healthy Subjects," Physiol. Res., 59:233-238 (2010).
Kurosu et al., "Tissue-specific Expression of βKlotho and Fibroblast Growth Factor (FGF) Receptor Isoforms Determines Metabolic Activity of FGF19 and FGF21," *J. Biol. Chem.*, 282(37):26687-26695 (2007).
Kurosu et al., "Supplemental Data For: Tissue-specific Expression of βKlotho and Fibroblast Growth Factor (FGF) Receptor Isoforms Determines Metabolic Activity of FGF19 and FGF21," *J. Biol. Chem.*, (2007) (available at: http://www.jbc.org/content/suppl/2007/07/11/M704165200.DC1/Kurosu_Suppl_Data.pdf (last visited Jul. 23, 2014).
Le et al., "Management of non-alcoholic fatty liver disease and steatohepatitis," *J. Clin. Exp. Hepatol.*, 2:156-173 (2012).
Lin et al., "The STAT3 inhibitor NSC 74859 is effective in hepatocellular cancers with disrupted TGF-beta signaling," *Oncogene*, 28:961-972 (2009).
Lin et al., "Adiponectin mediates the metabolic effects of FGF21 on glucose homeostasis and insulin sensitivity in mice," *Cell. Metab.*, 17:779-789 (2013).

(56) References Cited

OTHER PUBLICATIONS

Lindor, "Ursodeoxycholic acid for the treatment of primary biliary cirrhosis," *New Engl. J. Med.*, 11(357; 15) 1524-1529 (2007).
Ling et al., "Identification of Gut Factors that Mimic the Metabolic Benefits Seen After Gastric Bypass Surgery," American Diabetes Association, 72nd Scientific Sessions, Jun. 8-12, 2012, Philadelphia, PA, http://www.abstactsonline.com.
Ling et al., NGM Biopharmaceuticals, Identification of Gut Factors that Mimic the Metabolic Benefits of Gastric Bypass Surgery, p. 1, Jun. 8-12, 2012 Abstract.
Ling et al., "NGM282 Promotes HDL Biogenesis and Transhepatic Cholesterol Efflux to Prevent Atherosclerosis in Mice," NGM Biopharmaceuticals Inc. Poster, European Association forthe Study of the Liver (EASL), International Liver Congress, Apr. 11, 2019.
Luo et al., "A nontumorigenic variant of FGF19 treats cholestatic liver diseases," *Sci. Transl. Med.*, 6: 247ra100 (2014).
Mayo et al., "Effect of NGM282, an FGF19 Analogue, on Pruritus in Patients with Primary Sclerosing Cholangitis: Analysis of a Phase 2, Multicenter, Randomized, Double-Blind, Placebo-Controlled Trial," NGM Biopharmaceuticals Inc. Poster, European Association for the Study of the Liver (EASL), International Liver Congress, Apr. 11, 2019.
Micanovic et al., "Different roles of N- and C-termini in the functional activity of FGF21," *J. Cell. Physiol.*, 219:227-234 (2009),.
Miyata et al., "Involvement of Multiple Elements in FXR-mediated Transcriptional Activation of FGF19," *J. Steroid Biochm. Mol. Biol.*, 132:41-47 (2012).
Mudaliar et al., "Efficacy and safety of the farnesoid X receptor agonist obeticholic acid in patients with type 2 diabetes and non-alcoholic fatty liver disease," *Gastroenterology*, 145:574-582 (2013).
"NGM Bio Announces Results From Phase 2 Study Of NGM282 In NASH Patients Demonstrating Clinically Significant Improvements In Liver Histology After 12 Weeks," PipielineReview.com, pp. 1-5 (Apr. 15, 2018). Retrieved from the Internet: https://pipelinereview.com/...NASH-Patients-Demonstrating-Clinically-Significant-Improvements-In-Liver-Histology-After-12-Weeks.html, on Feb. 12, 2019.
Nguyen et al., "Purification of cholesterol 7 alpha-hydroxylase from human and rat liver and production of inhibiting polyclonal antibodies," *J. Biol. Chem.*, 265:4541-4546 (1990).
Nicholes et al., "A Mouse Model of Hepatocellular Carcinoma: Ectopic Expression of Fibroblast Growth Factor in Skeletal Muscle of Transgenic Mice," *Amer. J. Pathol.*, 160:2295-2307 (2002).
Oduyebi et al., "Effects of NGM282, an FGF19 variant, on colonic transit and bowel function in functional constipation: a randomized phase 2 trial," *Am. J. Gastoenterol.*, 113:725-734 (2018).
Ogawa et al., "BetaKlotho is Required for Metabolic Activity of Fibroblast Growth Factor 21," *Proc. Natl. Acad. Sci. USA.*, 104:7432-7437 (2007).
Pai et al., "Antibody-Mediated Inhibition of Fibroblast Growth Factor 19 Results in Increased Bile Acids Synthesis and Ileal Malabsorption of Bile Acids in Cynomolgus Monkeys," *Toxicological Sciences*, 126(2):446-456 (2012).
Paredes et al., "NGM282 Maintains a Durable Off-Treatment Response on Hepatic Steatosis, Inflammation and Fibrogenesis in Patients with Biopsy-Confirmed Nonalcoholic Steatohepatitis: Results of a Multi-Center Phase 2 Dose-Finding Study," AASLD Abstracts, *Hepatology*, 68(1):1459A-1460A (2018).
Paredes et al., "NGM282 Maintains a Durable Off-Treatment Response on Hepatic Steatosis, Inflammation and Fibrogenesis in Patients with Biopsy-Confirmed Nonalcoholic Steatohepatitis: Results of a Multi-Center Phase 2 Dose-Finding Study," NGM Biopharmaceuticals Inc. Poster, American Association for the Study of Liver Diseases (AASLD), Liver Meeting, Nov. 12, 2018.
Pattni et al., "Fibroblast Growth Factor 19 and 7α-Hydroxy-4-Cholesten-3-one in the Diagnosis of Patients With Possible Bile Acid Diarhea," *Clinical and Translational Gastroenterology*, 26:312-324 (2012).
Potthoff et al., "Endocrine Fibroblast Growth Factors 15/19 and 21: From Feast to Famine," *Genes Dev.*, 26:312-324 (2012).
Pusl et al., "Intrahepatic cholestasis of pregnancy," *Orphanet J. Rare Diseases*, 2:26 (2007).
Rose et al., "Molecular Control of Systemic Bile Acid Homeostasis by the Liver Glucocorticoid Receptor," *Cell Metabolism*, 14:123-130 (2011).
Rossi et al., "P1313 Ngm282, a Novel Specific Inhibitor of Cyp7a1-Mediated Bile Acid Synthesis, is Safe and Well Tolerated with Predictable Pharmacokinetics in Healthy Human Subjects," *J. Hepatology*, 60(1):S533 (2014).
Ryan et al., "FXR is a Molecular Target for the Effects of Vertical Sleeve Gastroectomy," *Nature*, 509(7499):183-188 (2014); epub ahead of print Mar. 26, 2014.
Sanyal et al., "Changes in Serum Bile Acids Correlate with 7alpha-Hydroxy-4-Cholesten-One and Fibrogenesis Biomarker Pro-C3 with NGM282 Therapy in Patients with Nonalcoholic Steatohepatitis," NGM Biopharmaceuticals, Inc. Poster, European Association for the Study of the Liver (EASL), International Liver Congress, Apr. 11, 2019.
Sawey et al., "Identification of a Therapeutic Strategy Targeting Amplified FGF19 in Liver Cancer by Oncogenomic Screening," *Cancer Cell*, 19(3):347-358 (2011).
Schaap et al., "High expression of the bile salt-homeostatic hormone fibroblast growth factor 19 in the liver of patients with extrahepatic cholestasis," *Hepatol.*, 49:1228-1235 (2009).
Schaap, "Role of Fibroblast Growth Factor 19 in the Control of Glucose Homeostasis," *Curr. Opin. Clin. Nutr. Metab. Care*, 15(4):386-391 (2012).
"TaqMan SNP Genotyping Assays," Life Technologies Corporation (2012).
Tartaglia et al., "Identification and expression cloning of a leptin receptor, OB-R," *Cell*, 83:1263-1271 (1995).
Tokuriki et al., "Stability effects of mutations and protein evolvability," *Curr. Opin. Struct. Biol.*, 19(5):596-604 (2009).
Tomlinson et al., "Transgenic Mice Expressing Human Fibroblast Growth Factor-19 Display Increased Metabolic Rate and Decreased Adiposity," *Endocrinology*, 143(5):1741-1747 (2002).
United States Securities and Exchange Commission, *Form S-1 Registration Statement: NGM Biopharmaceuticals, Inc.*, Sep. 28, 2018, pp. 1-282.
Vijayvargiya et al., "Diagnostic Methods for Bile Acid Malabsorption in Clinical Practice," *Clin. Gastroenterol. Hepatol.*, 11(10):1232-1239 (2013).
Walters et al., "Managing bile acid diarrhoea," *Ther. Adv. Gastroenterol.*, 3(6):349-357 (2010).
Walters, "Bile acid diarrhoea and FGF19: new views on diagnosis, pathogenesis and therapy," *Nat. Rev. Gastroenterol. Hepatol.*, 11(7):426-434 (2014).
Walters, "A variant of FGF19 for treatment of disorders of cholestasis and bile acid metabolism," *Ann. Transl. Med.*, 3(S1):S7 (2015).
Wang et al., "Leptin in hepatocellular carcinoma," *World J. Gastroenterol.*, 16:5801-5809 (2010).
Wong et al., "Pharmacogenetics of the effects of colesevelam on colonic transit in irritable bowel syndrome with diarrhea," *Dig. Dis. Sci.*, 57(5):1222-1226 (2012).
Wu et al., "C-terminal Tail of FGF19 Determines Its Specificity toward Klotho C-receptors," *J. Biol. Chem.*, 283(48):33304-33309 (2008).
Wu et al., "Role of FGF19 Induced FGFR4 Activation in the Regulation of Glucose Homeostasis," *Aging*, 1(12):1023-1027 (2009).
Wu et al., "Selective Activation of FGFR4 by an FGF19 Variant Does Not Improve Glucose Metabolism in ob/ob Mice," *Proc. Natl. Acad. Sci. USA*, 106(34):14379-14384 (2009).
Wu et al., "FGF19-induced Hepatocyte Proliferation is Mediated Through FGFR4 Activation," *J. Biol. Chem.*, 285(8):5165-5170 (2010).
Wu et al., "Separating Mitogenic and Metabolic Activities of Fibroblast Growth Factor 19 (FGF19)," *Proc. Natl. Acad. Sci. USA*, 107(32):14158-14163 (2010).
Wu et al., "Therapeutic Utilities of Fibroblast Growth Factor 19," *Expert Opin. Ther. Targets*, 15(11):1307-1316 (2011).
Wu et al., "FGF19 Regulates Cell Proliferation, Glucose and Bile Acid Metabolism via FGFR4-Dependent and Independent Pathways," *PLoS One*, 6(3):e17868 (2011).

(56) References Cited

OTHER PUBLICATIONS

Xie et al., "FGF-19, A Novel Fibroblast Growth Factor with Unique Specificity for FGFR4," *Cytokine*, 11(10):729-735 (1999).
Zhang et al., "Adenovirus-adeno-associated virus hybrid for large-scale recombinant adeno-associated virus production," *Hum. Gene Ther.*, 20:922-929 (2009).
Zhou et al., "Serum tumor markers for detection of hepatocellular carcinoma," *World J. Gastroenterol.*, 12(8):1175-1181 (2006).
Zhou et al., "Separating Tumorigenicity from Bile Acid Regulatory Activity for Endocrine Hormone FGF19," *Cancer Res.*, 74(12):3306-3316 (2014).
Zhou et al., "Engineered fibroblast growth factor 19 reduces liver injury and resolves sclerosing cholangitis in Mdr2-deficient mice," *Hepatology*, 63(3):914-929 (2016).
Zhou et al., "Non-cell-autonomous activation of IL-6/STAT3 signaling mediates FGF19-driven hepatocarcinogenesis," *Nat. Commun.* 8:15433 (2017).
Zhou et al., "Therapeutic FGF19 promotes HDL biogenesis and transhepatic cholesterol efflux to prevent atherosclerosis," *J. Lipid Res.*, 60:550-565 (2019).
Anonymous, "Tofacitinib," *Wikipedia: The Free Encyclopedia*, Retrieved from the Internet: https://en.wikioedia.org/w/index.php?title=Tofacitinib&oldid=723710124, retrieved on Feb. 19, 2020.
Bergasa, "Pruritus of Cholestasis," *Itch: Mechanisms and Treatment*, Carstens et al. eds., CRC Press/Taylor & Francis, Boca Raton, FL, Chapter 6, 24 pages (2014).
Bilori et al., "Tofacitinib as novel salvage therapy for refractory T-cell large granular lymphocytic leukemia," *Leukemia*, 29(12):2427-2429 (2015).
Blaskovich et al., "Discovery of JSI-124 (cucurbitacin I), a selective Janus kinase/signal transducer and activator of transcription 3 signaling pathway inhibitor with potent antitumor activity against human and murine cancer cells in mice," *Cancer Res.*, 63(6):1270-1279 (2003).
Hirschfield et al., "A long term safety extension trial of the farnesoid X receptor (FXR) agonist obeticholic acid (OCA) and UDCA in primary biliary cirrhosis (PBC)," *Hepatol.*, 54(4):429A (2011).
Ilchenko, "Bile acids in norm and pathology," *Experimental and Clinical Gastroenterology*, 4:3-13 (2010). (English translation of abstract attached).
Johnston et al., "New insights into bile acid malabsorption," *Curr. Gastroenterol. Rep.*, 13:418-425 (2011).
Kremer et al., "High serum autotaxin activity predisposes to sever pruritus during treatment with obeticholic acid in primary biliary cirrhosis," *J. Hepatol.*, 54:2, 1 page (2011).
Li et al., "Circulating FGF19 closely correlates with bile acid synthesis and cholestasis in patients with primary biliary cirrhosis," *PLOS One*, 12(6):1-11 (2017).
Ling et al., "Activation of IL-6/STAT3 signaling mediates FGF19-driven hepatocarcinogenesis," *J. Hepatol.*, 66(1):S459 (2017).
Mason et al., "Farnesoid-X receptor agonists: A new class of dmgs for the treatment of PBC? An international study evaluating the addition of INT-747 to ursodeoxycholic acid," *J. Hepatol.*, 52:2, 1 page (2010).
Miura et al., "Fibroblast growth factor 19 expression correlates with tumor progression and poorer prognosis of hepatocellular carcinoma," *BMC Cancer*, 12:56, pp. 1-15 (2012).
Molina et al., "Inhibition of experimental tumor models achieved through systematic elevation of FGF19 in vivo," *Proc. Amer. Assoc. Cancer Res.*, 45:1-3 (2004).
Nagamatsu et al., "FGF19 Promotes Progression of Prostate Cancer," *The Prostate*, 75(10):1092-1101 (2015).
Paule et al., "The NF-[kappa]B/IL-6 pathway in metastatic androgen-independent prostate cancer: new therapeutic approaches?," *World J. Urol.*, 25(5):477-489 (2007).
Repana et al., "Targeting FGF19/FGFR4 Pathway: A Novel Therapeutic Strategy for Hepatocellular Carcinoma," *Diseases*, 3(4):294-305 (2015).
Schreuder et al., "The hepatic response to FGF19 is impaired in patients with nonalcoholic fatty liver disease and insulin resistance," *Am. J. Physiol. Gastrointest. Liver Physiol.*, 298:G440-G445 (2010).
Tiong et al., "Fibroblast growth factor receptor 4 (FGFR4) and fibroblast growth factor 19 (FGF19) autocrine enhance breast cancer cells survival," *Oncotarget*, 7(36):57633-57650 (2016).
Walters et al., "The response of patients with bile acid diarrhoea to the farnesoid X receptor agonist obeticholic acid," *Ailment Pharmacol. Ther.*, 41:54-64 (2015).
Wan et al., "Tumor-associated macrophages produce interleukin 6 and signal via STAT3 to promote expansion of human hepatocellular carcinoma stem cells," *Gastrointerology*, 147(6):1393-1404 (2014).
Wang et al., "Inhibition of IL-6 expression in LNCaP prostate cancer cells by a combination of atorvastatin and celecoxib," *Oncology Reports*, 32(2):835-841 (2014).
Yang et al., "Saw Palmetto induces growth arrest and apoptosis of androgen-dependent prostate cancer LNCaP cells via inactivation of STAT 3 and androgen receptor signalizing," *Database BIOSIS*, Accession No. PREV200700539177 (2007).
Yoneda et al., "Noninvasive assessment of liver fibrosis by measurement of stiffness in patients with nonalcoholic fatty liver disease (NAFLD)," *Digestive Liver Disease*, 40:371-378 (2008).
Andersen et al., 2013, "Etiology and therapeutic approach to elevated lactate levels," Mayo Clin Proc., 88(10):1127-1140.
Beyoglu et al., 2013, "The metabolomic window into hepatobiliary disease," J Hepatol., 59(4):842-858.
Bruix et al., 2005, "Management of hepatocellular carcinoma," Hepatology, 42(5):1208-1236.
Czajkowsky et al., "Fc-fusion proteins: new developments and future perspectives," EMBO Mol. Med., 4(10):1015-1028 (2012).
Drolz et al., 2019, "Lactate Improves Prediction of Short-Term Mortality in Critically Ill Patients With Cirrhosis: A Multinational Study," Hepatology, 69(1):258-269 (Epub 2018).
Paumgartner, et al. "Gallstones: pathogenesis," Lancet, 338(8775):1117-1121 (1991).
Penz-Osterreicher et al., 2011, "Fibrosis in autoimmune and cholestatic liver disease," Best Pract Res Clin Gastroenterol., 25(2):245-258.
Zhou et al., "Engineered FGF19 eliminates bile acid toxicity and lipotoxicity leading to resolution of steatohepatitis and fibrosis in mice," Hepatol Commun., 1(10):1024-1042 (2017).

\* cited by examiner

```
                         SEQUENCE LISTING

<160> NUMBER OF SEQ ID NOS: 1

<210> SEQ ID NO 1
<211> LENGTH: 194
<212> TYPE: PRT
<213> ORGANISM: Homo sapiens

<400> SEQUENCE: 1

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys
```

METHODS OF TREATING FIBROBLAST GROWTH FACTOR 19-MEDIATED CANCERS AND TUMORS

CROSS-REFERENCE TO RELATED APPLICATIONS

This application is a 371 U.S. national stage application of international application Serial No. PCT/US2017/048609 filed Aug. 25, 2017, which claims the benefit of priority to U.S. Provisional Application No. 62/380,324, filed Aug. 26, 2016, the content of each of which is hereby incorporated by reference in its entirety.

FIELD

The invention relates to methods of treating fibroblast growth factor 19 (FGF19)-mediated cancers and tumors. Provided are methods of treating FGF19-mediated cancers and tumors by administering to a subject an anti-interleukin-6 (IL-6) antibody or anti-IL-6 receptor antibody, and/or an inhibitor of the signal transducer and activator of transcription 3 (STAT3)/Janus kinase (JAK) signaling pathway.

BACKGROUND

Hepatocellular carcinoma (HCC) is the second most common cause of cancer-related deaths worldwide (Llovet et al., 2016, Nat Rev Dis Primers, 2:16018). The pathogenesis of HCC is frequently linked to inflammatory responses triggered by chronic viral infection, alcohol consumption, toxin ingestion, and metabolic stress (El-Serag, 2011, New England J Med, 365:118-1127; Michelotti et al., 2013, Nature Reviews, 10:656-665; Sun and Karin, 2012, Hepatology, 49:297-305). Despite the considerable efforts that have been made in basic and clinical research, the current state of treatment for HCC lags far behind that for many other solid tumors. Although the approval of sorafenib as the first targeted therapy for HCC heralded a new era in managing advanced HCC, only minimal survival benefit was seen with sorafenib therapy (Llovet et al., 2008, New England J Med, 359:378-390).

Over the past decade, multiple studies have delineated a comprehensive landscape of genetic alterations in HCC (Zucman-Rossi et al., 2015, Gastroenterology, 149:1226-1239). Focal amplification of chromosome 11q13 containing FGF19 is the one of the most frequent amplification events in HCC with the highest amplitude among all genes (Sawey et al., 2011, Cancer Cell, 19:347-358; Zucman-Rossi et al., 2015, Gastroenterology, 149:1226-1239). Amplification of the FGF19 locus is associated with more aggressive tumors, higher risk of recurrence after resection, and lower survival rates (Ahn et al., 2014, Hepatology, 60:1972-1982; Hyeon et al., 2013, Digestive Diseases and Sciences, 58:1916-1922; Miura et al., 2012, BMC Cancer, 12:56; Schulze et al., 2015, Nature Genetics, 47:505-511). These findings have been recapitulated in mouse models, as ectopic expression of FGF19 in transgenic mice or using an adeno-associated viral (AAV) delivery system promote the development of HCC in mice (Nicholes et al., 2002, Amer J Path, 160:2295-2307; Zhou et al., 2016, Hepatology, 63:914-929; Zhou et al., 2014, Cancer Research, 74:3306-3316).

FGF19 is a multifunctional endocrine hormone that is important for bile acid, carbohydrate and energy homeostasis, and liver regeneration (Angelin et al., 2012, Cell Metabolism, 16:693-705; Beenken and Mohammadi, 2009, Nature Reviews Drug Discovery, 8:235-253; Degirolamo et al., 2016, Nature Reviews Drug Discovery, 15:51-69; Kliewer and Mangelsdorf, 2015, Digestive Diseases, 33:327-331; Kong et al., 2014, Amer J Physiology: Gastrointestinal and Liver Physiology, 306, G893-902; Uriarte et al, 2014, Gut, 62:899-910). Physiological levels of FGF19 act on hepatocytes to limit de novo synthesis of bile acids and to protect liver from these molecules (Kliewer and Mangelsdorf, 2015, Digestive Diseases, 33:327-331). These effects of FGF19 are mediated by a receptor complex comprised of fibroblast growth factor receptor 4 (FGFR4) and β-klotho (KLB) (Kliewer and Mangelsdorf, 2015, Digestive Diseases, 33:327-331). The liver-enriched receptor FGFR4 is also thought to mediate the tumorigenic effects of FGF19, since inactivation of FGFR4 via gene knockout or neutralizing antibodies reduce the tumor burden in FGF19 transgenic mice (Desnoyers et al., 2008, Oncogene, 27:85-97; French et al., 2012, PLoS One, 7:e36713; Wu et al., 2011, PLoS One, 6:317868, Wu et al., 2010, JBC, 285:5165-5170).

A neutralizing anti-FGF19 antibody has been developed and was reported to block clonogenicity and tumorigenicity of HCC models harboring FGF19 amplification (Desnoyers et al., 2008, Oncogene, 27:85-97; Sawey et al., 2011, Cancer Cell, 19:437-358). However, targeted inhibition of FGF19 triggered significant safety concerns during preclinical development (Pai et al., 2012, Tox Sciences, 126:446-456). Similar safety concerns are applicable to FGFR4-specific small molecule inhibitors that are in clinical development (Hagel et al., 2015, Cancer Discovery, 5:424-437).

In view of the severity of FGF19-mediated HCC, along with the shortcomings of current treatment options, alternative treatment modalities are needed.

SUMMARY

FGF19 is a major driver in liver carcinogenesis (such as in the development of HCC) but the signaling pathways that drive tumor progression remain elusive. Targeted inhibition of FGF19 presented serious safety concerns as it plays an important physiological role in the regulation of hepatic bile acid synthesis. Thus, selective inhibition of oncogenic signaling without affecting metabolic function is a long-sought-after, but to date unachieved goal, in targeted therapy of the FGF19 signaling pathway.

The inventors have shown that the cytokine IL-6 and its downstream effector STAT3 play an important role in FGF19-mediated tumorigenesis. Without being bound to a particular theory, the inventors suggest an essential mechanism of FGF19-related tumorigenicity contemplating that FGF19 can act in a non-cell autonomous manner by engaging IL-6 secreted from liver-infiltrating innate immune cells, underscoring the complex interactions that occur between different cell types in the liver microenvironment to promote HCC progression.

The present disclosure is based, in part, on a discovery that the liver microenvironment can be modified to limit or erase FGF19-mediated tumorigenesis, i.e., that antibody-mediated neutralization of IL-6, genetic ablation of IL-6, hepatocellular deficiency of STAT3, or pharmacological inhibition of the JAK/STAT3 pathway abrogate the protumorigenic effects of FGF19 without substantially affecting one or more of FGF19's metabolic functions. In certain embodiments, the metabolic function of FGF19 includes the ability to regulate bile acid synthesis, glucose metabolism, and/or energy homeostasis.

In further embodiments, provided herein is a method of treating a FGF19-mediated cancer or tumor, or ameliorating a symptom of the cancer or tumor, in a subject having an FGF19-mediated cancer or tumor by administering to said subject an anti-IL-6 antibody or anti-IL-6 receptor antibody. In further embodiments, provided herein is a method of preventing a FGF19-mediated cancer or tumor in a subject by administering to said subject an anti-IL-6 antibody or anti-IL-6 receptor antibody, wherein one or more of the metabolic functions of FGF19 are not substantially affected. In further embodiments, the above methods treat or prevent the cancer or tumor while not substantially affecting one or more of the metabolic functions of FGF19. Anti-IL-6 antibodies or anti-IL-6 receptor antibodies useful in the methods provided herein include, but are not limited to, siltuximab, tocilizumab, sarilumab, olokizumab, clazakizumab (BMS-945429), elsilimomab, sirukumab, and any combination thereof. In one embodiment, the anti-IL-6 antibody is siltuximab. In one embodiment, the anti-IL-6 receptor antibody is tocilizumab. In one embodiment, the anti-IL-6 antibody or anti-IL-6 receptor antibody is a neutralizing antibody.

In some embodiments, methods provided herein further include determining the expression level of FGF19 in a cancer or tumor sample.

In further embodiments, provided herein is a method of treating a FGF19-mediated cancer or tumor, or ameliorating a symptom of the cancer or tumor, in a subject having a FGF19-mediated cancer or tumor, by administering to said subject an inhibitor of the STAT3/JAK signaling pathway. In further embodiments, provided herein is a method of preventing a FGF19-mediated cancer or tumor in a subject by administering to said subject an inhibitor of the STAT3/JAK signaling pathway. In further embodiments, the above methods treat or prevent the cancer or tumor while not substantially affecting one or more of the metabolic functions of FGF19. Inhibitors of the STAT3/JAK signaling pathway useful in the methods provided herein include, but are not limited to, tofacinitib, ruxolitinib, baricitinib (LY-3009104), filgotinib (G-146034, GLPG-0634), gandotinib (LY-2784544), lestaurtinib (CEP-701), momelotinib (GS-0387, CYT-387), pacritinib (SB1518), upadacitinib (ABT-494), cucurbitacin I (JSI-124), CHZ868, fedratinib (SAR302503), and any combination thereof. In one embodiment, the inhibitor of the STAT3/JAK signaling pathway is tofacinitib.

In some embodiments, methods provided herein further include determining the expression level of a STAT3 target gene in a cancer or tumor sample. In some embodiments, the STAT3 target gene is selected from the group consisting of BIRC5, BCL2, HSPA4, BCL2L1 and MCL1.

In certain embodiments, provided herein is a pharmaceutical composition for treating a FGF19-mediated cancer or tumor, or a symptom thereof, in a subject, wherein the composition comprises an anti-IL-6 antibody or anti-IL-6 receptor antibody and a pharmaceutically acceptable carrier. In one embodiment, the anti-IL-6 antibody or anti-IL-6 receptor antibody is siltuximab, tocilizumab, sarilumab, olokizumab, clazakizumab (BMS-945429), elsilimomab, sirukumab, or any combination thereof. In one embodiment, the pharmaceutical composition for treating a FGF19-mediated cancer or tumor, or a symptom thereof, in a subject comprises siltuximab and a pharmaceutically acceptable carrier. In another embodiment, the pharmaceutical composition for treating a FGF19-mediated cancer or tumor, or a symptom thereof, in a subject comprises tocilizumab and a pharmaceutically acceptable carrier.

The present disclosure also contemplates a pharmaceutical composition for treating a FGF19-mediated cancer or tumor, or a symptom thereof, in a subject, wherein the composition comprises an inhibitor of the STAT3/JAK signaling pathway and a pharmaceutically acceptable carrier. In one embodiment, the inhibitor of the STAT3/JAK signaling pathway is tofacinitib, ruxolitinib, baricitinib (LY-3009104), filgotinib (G-146034, GLPG-0634), gandotinib (LY-2784544), lestaurtinib (CEP-701), momelotinib (GS-0387, CYT-387), pacritinib (SB1518), upadacitinib (ABT-494), cucurbitacin I (JSI-124), CHZ868, fedratinib (SAR302503), or any combination thereof. In certain embodiments, a pharmaceutical composition for treating a FGF19-mediated cancer or tumor, or a symptom thereof, in a subject comprises tofacinitib and a pharmaceutically acceptable carrier.

In further embodiments, the disclosure contemplates an anti-IL-6 antibody or anti-IL-6 receptor antibody for use in the treatment of a FGF19-mediated cancer or tumor. In further embodiments thereof, the anti-IL-6 antibody or anti-IL-6 receptor antibody is selected from the group consisting of siltuximab, tocilizumab, sarilumab, olokizumab, clazakizumab (BMS-945429), elsilimomab, and sirukumab. In one embodiment, the anti-IL-6 antibody is siltuximab. In another embodiment, the anti-IL-6 receptor antibody is tocilizumab.

In additional embodiments, the disclosure contemplates an inhibitor of the STAT3/JAK signaling pathway for use in the treatment of a FGF19-mediated cancer or tumor. In further embodiments, the inhibitor of the STAT3/JAK signaling pathway is selected from the group consisting of tofacinitib, ruxolitinib, baricitinib (LY-3009104), filgotinib (G-146034, GLPG-0634), gandotinib (LY-2784544), lestaurtinib (CEP-701), momelotinib (GS-0387, CYT-387), pacritinib (SB1518), upadacitinib (ABT-494), cucurbitacin I (JSI-124), CHZ868, and fedratinib (SAR302503). In one embodiment, the inhibitor of the STAT3/JAK signaling pathway is tofacinitib.

In certain embodiments of the disclosure, the cancer or tumor is a liver, lung, breast, colon, esophageal, oral, laryngeal, prostate, bladder, renal, uterine, ovarian, testicular, rectal, pancreas, stomach, brain, or thyroid cancer or tumor. In certain embodiments, the cancer or tumor is a liver, lung, breast, colon, or esophageal cancer or tumor. In one embodiment, the cancer or tumor is a liver cancer or tumor. In one embodiment, the liver cancer or tumor is hepatocellular carcinoma (HCC). In certain embodiments, the subject has HCC or is at risk of developing HCC. In one embodiment, the subject is a human.

In further embodiments, provided herein is a kit comprising the anti-IL-6 antibodies or anti-IL-6 receptor antibodies, or the inhibitors of the STAT3/JAK signaling pathway, and pharmaceutical compositions thereof suitable for administration to a subject.

In some embodiments, provided herein is a kit for predicting the responsiveness of a cancer or tumor to an anti-IL-6 antibody or an anti-IL-6 receptor antibody treatment, comprising at least one agent for determining the expression level of FGF19 in the cancer or tumor, and an ancillary agent.

In some embodiments, provided herein is a kit for predicting the responsiveness of a cancer or tumor to a treatment with an inhibitor of the STAT3/JAK signaling pathway, comprising at least one agent for determining the expression level of a STAT3 target gene in the cancer or tumor, and an ancillary agent.

BRIEF DESCRIPTION OF THE DRAWINGS

(FIG. 1A) An immunoblot analysis of pSTAT3$^{Y705}$ in liver lysates of db/db mice treated with recombinant FGF19 protein is shown. Total-STAT3 and β-actin serve as loading controls. pERK and total ERK levels were also determined. Primary hepatocytes were isolated by collagenase digestion followed by low-speed centrifugation and plating onto collagen-coated plates. (FIG. 1B) The panel shows lack of pSTAT3$^{Y705}$ activation in primary mouse hepatocytes by FGF19. Cell lysates were prepared at the indicated time points following FGF19 stimulation and analyzed for phosphorylation of the various proteins. Mouse IL-6 (mIL-6) was included as a positive control. (FIG. 1C) The panel shows lack of pSTAT3$^{Y705}$ activation by FGF19 in primary human hepatocytes. Human IL-6 (hIL-6) is included as a positive control.

(FIG. 2A) Flow cytometry analysis of BrdU-labeled livers is shown. Representative histograms from hepatocytes stained with 7-ADD and anti-BrdU-APC are shown. (FIG. 2B) BrdU-positive hepatocytes as a percentage of total hepatocytes from vehicle (V)-treated (n=5) or FGF19-treated (n=5) mice were quantified by flow cytometry. (FIG. 2C) Shown are circulating FGF19 levels on day 6 post-implant of osmotic pumps. (FIG. 2D) Lack of proliferative effects of FGF19 on primary mouse hepatocytes. Primary cultures of hepatocytes isolated from mouse liver were incubated with recombinant FGF19 protein at the indicated concentrations for 48 hours and BrdU was added during the last 20 hours of incubation. BrdU incorporation was determined using a luminescence method. Mouse hepatocyte growth factor (mHGF) was included as a positive control. RLU, relative luminescence unit. (FIG. 2E) Lack of proliferative effects of FGF19 on primary human hepatocytes. Primary cultures of hepatocytes isolated from human liver were incubated with recombinant FGF19 protein. Human hepatocyte growth factor (hHGF) was included as a positive control. Data are represented as mean+SEM. **P<0.001 versus control group by unpaired, two-tailed t-test.

(FIG. 3A) Schematic representation of generating Stat3$^{ΔHep}$ mice with AAV-mediated delivery of Cre recombinase. The TBG (thyroxine binding globin) promoter drives hepatocyte-specific Cre expression. Exons in Stat3 gene are labeled. (FIG. 3B) Liver tumor multiplicity. Dots in scatterplot represent individual animals. (FIG. 3C) Liver tumor size recorded as maximum tumor diameter in each mouse. (FIG. 3D) Shown is a quantification of glutamine synthetase-positive tumor area as a percentage of total liver area. (FIG. 3E) Shown are liver weights from mice of the indicated genotypes. (FIG. 3F) Shown are circulating levels of FGF19 at the end of the study. Values are mean+SEM. ***P<0.001, *P<0.05 by unpaired, two-tailed t-test of indicated groups.

(FIG. 4A) The panel shows hepatic Cyp7a1 mRNA levels. (FIG. 4B) The panel shows hepatic Cyp8b1 mRNA levels. (FIG. 4C) The panel shows mice body weight. (FIG. 4D) The panel shows plasma glucose. (FIG. 4E) The panel shows body composition. All parameters were determined in live animals prior to euthanasia. Values are mean+SEM. ***P<0.001, *P<0.05 by unpaired, two-tailed t-test of indicated groups.

(FIG. 5A) Hepatic IL-6 mRNA is induced in FGF19-treated db/db mice. (FIG. 5B) Lack of induction of canonical pSTAT3-activating cytokines, such as IL-11, LIF, OSM, CNTF, and CTF-1, in FGF19-treated db/db mice. (FIG. 5C) Lack of induction of additional pSTAT3-activating growth factors and cytokines, such as EGF, IL-10, IL-21, IL-22, and IL-31, in FGF19-treated db/db mice. (FIG. 5D) Suppression of hepatic Cyp7a1 mRNA in FGF19-treated db/db mice. (FIG. 5E) Blocking antibody against mouse IL-6 abolishes pSTAT3-activation by FGF19. (FIG. 5F) Intracellular IL-6 cytokine staining of non-parenchymal cells analyzed by flow cytometry. (FIG. 5G) Co-localization of IL-6 with markers of myeloid cells (CD11b$^+$), Kupffer cells (F4/80$^+$), neutrophils (Ly6G$^+$), NK cells (NK1.1$^+$), but not T cells (CD3$^+$) or B cells (CD19$^+$). Values are mean+SEM. ***P<0.001 by unpaired, two-tailed t-test.

(FIG. 6A) Numbers of macroscopic tumors per liver. Dots in scatterplot represent individual animals. (FIG. 6B) Tumor size. (FIG. 6C) Quantification of tumor area. (FIG. 6D) Ratios of liver-to-body weight. (FIG. 6E) Circulating FGF19 levels at the end of the study. (FIG. 6F) Body weight of the animals. (FIG. 6G) Quantitative RT-PCR of hepatic Cyp7a1 expression. (FIG. 6H) Hepatic Cyp8b1 mRNA levels. Values are mean+SEM. *P<0.001, P<0.01, *P<0.05 versus control group by one-way ANOVA.

(FIG. 7A) An AAV-SOCS3 study was conducted in db/db mice. 11 week old db/db mice were administered (i) AAV-FGF19 by i.v. injection, with or without AAV-SOCS3, or (ii) a control virus. Mice were euthanized 24 weeks later for liver tumor analysis. SOCS3 inhibited FGF19-induced liver tumor formation. (FIG. 7B) FGF19 normalized HbA1c in db/db mice in the absence or presence of SOCS3. (FIG. 7C) A tofacitinib study was conducted in db/db mice. 12 week old db/db mice were i.v. administered with AAV-FGF19 or a control virus. Tofacitinib treatment was initiated 4 weeks later. Mice were euthanized 24 weeks after AAV injection. Tofacitinib inhibited FGF19-induced liver tumor formation. (FIG. 7D) FGF19 normalized blood glucose levels in db/db mice irrespective of tofacitinib treatment. (FIG. 7E) An anti-IL-6 antibody study was conducted in Mdr2$^{-/-}$ mice. Mdr2$^{-/-}$ mice received a single tail vein injection of 1×10$^{11}$ v.g. AAV-FGF19. Starting from week 14 after AAV injection, mice were dosed intraperitoneally (i.p.) with 10 mg/kg anti-mouse IL-6 antibody or an isotype control antibody weekly. Tumors were analyzed 24 weeks after AAV-FGF19 administration. The panel shows tumor multiplicity and tumor size. (FIG. 7F) Serum levels of alkaline phosphatase at the end of the study. (FIG. 7G) Serum levels of total bile acids at the end of the study.

(FIG. 8A) Primary hepatocytes were isolated by collagenase digestion methods from mouse livers. Real-time quantitative RT-PCR was performed to determine mRNA levels of FGFR1, FGFR4, and KLB receptors. Data are normalized to housekeeping gene Gapdh and are relative to the expression in the brain. (FIG. 8B) Primary hepatocytes were isolated by collagenase digestion methods from human livers. Real-time quantitative RT-PCR was performed to determine mRNA levels of FGFR1, FGFR4, and KLB receptors. Data are normalized to housekeeping gene Gapdh and are relative to the expression in the brain.

(FIG. 9A) Survinin, Bcl-X$_L$, Cyclin D1. (FIG. 9B) Cyclin A2, Cyclin B1, Cyclin B2. (FIG. 9C) Ki-67, PCNA, AFP.

(FIG. 10A) Survinin, Bcl-X$_L$, Cyclin D1. (FIG. 10B) Cyclin A2, Cyclin B1, Cyclin B2. (FIG. 10C) Ki-67, PCNA, AFP.

(FIG. 11A) Plasma glucose level. (FIG. 11B) Insulin levels. (FIG. 11C) Body composition.

(FIG. 12A) Reduction of liver tumor area after co-expression of SOCS3. (FIG. 12B) Bile acid-lowering effect when co-expressed with SOCS3. (FIG. 12C) Circulating levels of FGF19 in all groups of db/db mice. (FIG. 12D) Effect of tofacitinib on FGF19's effects on average tumor load. (FIG. 12E) Effect of tofacitinib on FGF19's effects on HbA1c levels. (FIG. 12F) Effect of tofacitinib on FGF19's effects on bile acid levels. (FIG. 12G) Circulating levels of FGF19 in all groups of mice. (FIG. 12H) Levels of alkaline phosphatase (ALP), alanine aminotransferase (ALT), aspartate aminotransferase (AST), and bile acids in Mdr2$^{-/-}$ mice administrated AAV-FGF19. (FIG. 12I) Tumor area in FGF19-expressing Mdr2$^{-/-}$ mice treated with anti-IL-6 antibody. (FIG. 12J) ALT levels in Mdr2$^{-/-}$ mice treated with anti-IL-6 antibody. (FIG. 12K) AST levels in Mdr2$^{-/-}$ mice treated with anti-IL-6 antibody. (FIG. 12L) Circulating FGF19 levels in all groups of mice.

DETAILED DESCRIPTION

Figure 1A:
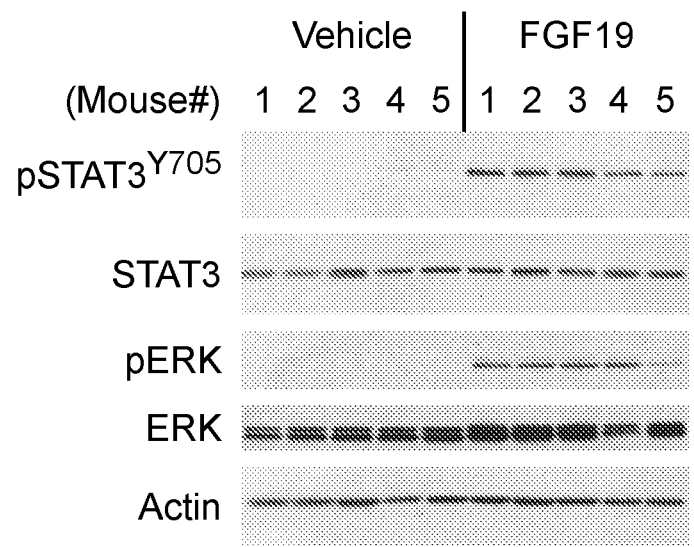
FIGS. 1A-1C depict a non-cell autonomous activation of hepatocellular STAT3 by FGF19. 11-week old db/db mice received a single intraperitoneal injection of 1 mg/kg FGF19 or vehicle (saline), and livers were harvested 2 hours post-dose (n=5 per group).

Before the present disclosure is further described, it is to be understood that the disclosure is not limited to the particular embodiments set forth herein, and it is also to be understood that the terminology used herein is for the purpose of describing particular embodiments only, and is not intended to be limiting.

Overview

The present disclosure contemplates the identification of agents, and compositions thereof, using the methods described herein. The methods provide an accurate, efficient methodology for the identification of agents that do not induce cancerous conditions (e.g., a FGF19-mediated cancer or tumor, or a symptom thereof).

In certain embodiments, the methods provided herein are useful in identifying agents that antagonize the oncogenic activity of FGF19. In certain embodiments, such agents have therapeutic utility in the treatment and/or prevention of various diseases, disorders and conditions, and/or the symptoms thereof, pertaining to, for example, a FGF19-mediated cancer or tumor, or a symptom thereof. By way of example, but not limitation, the agents, and compositions thereof, can be used for the treatment and/or prevention of a FGF19-mediated cancer or tumor, or a symptom thereof.

Also provided are methods of antagonizing the oncogenic activity of FGF19 in a subject and, in certain embodiments, methods of treating a FGF19-mediated cancer or tumor, or a symptom thereof. In certain embodiments of the disclosure, the cancer or tumor is a liver, lung, breast, colon, esophageal, oral, laryngeal, prostate, bladder, renal, uterine, ovarian, testicular, rectal, pancreas, stomach, brain, or thyroid cancer or tumor. In certain embodiments, the FGF19-mediated cancer or tumor is liver cancer or tumor. In one embodiment, the liver cancer or tumor is hepatocellular carcinoma (HCC). In one embodiment, the subject is a human.

Definitions

The terms "patient" or "subject" are used interchangeably to refer to a human or a non-human animal (e.g., a mammal).

The terms "treat," "treatment" and "treating" as used herein, refer to the reduction or amelioration of the progression, severity, and/or duration (such as reduced rate of growth of a cancer or tumor, stop the growth of a cancer or tumor, or cause the regression of a cancer or tumor) of a FGF19-mediated cancer or tumor resulting from the administration of one or more therapies (including, but not limited to the administration of anti-IL-6 antibodies, anti-IL-6 receptor antibodies, or/or inhibitors of the STAT3/JAK signaling pathway provided herein).

The term "in need of treatment" as used herein refers to a judgment made by a physician or other medical professional that a subject requires or will benefit from treatment.

The terms "prevent", "preventing", "prevention" and the like refer to a course of action (such as administering an anti-IL-6 antibody, an anti-IL-6 receptor antibody, and/or an inhibitor of the STAT3/JAK signaling pathway or a pharmaceutical composition comprising an anti-IL-6 antibody, an anti-IL-6 receptor antibody, and/or an inhibitor of the STAT3/JAK signaling pathway) initiated in a manner (e.g., prior to the onset of a FGF19-mediated cancer or tumor) so as to prevent, suppress, inhibit or reduce, either temporarily or permanently, a subject's risk of developing the FGF19-mediated cancer or tumor or the like (as determined by, for example, the absence of clinical symptoms) or delaying the onset thereof, generally in the context of a subject predisposed to having the FGF19-mediated cancer or tumor. In certain instances, the terms also refer to slowing the progression of the FGF19-mediated cancer or tumor or inhibiting progression thereof to a harmful or otherwise undesired state.

The term "in need of prevention" as used herein refers to a judgment made by a physician or other medical professional that a subject requires or will benefit from preventative care.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects.

The phrase "in a sufficient amount to effect a change" means that there is a detectable difference between a level of an indicator measured before (e.g., a baseline level) and after administration of a particular therapy. Indicators include any objective parameter (e.g., cancer-free state) or subjective parameter (e.g., a subject's feeling of well-being).

The term "inhibitor" as used herein, is a substance that slows down or prevents a particular chemical reaction or process, or reduces or stops the activity of a particular enzyme or a cascade of inner cellular events.

The terms "assaying" and "measuring" and grammatical variations thereof are used interchangeably herein and refer to either qualitative or quantitative determinations, or both qualitative and quantitative determinations. When the terms are used in reference to detection, any means of assessing the relative amount is contemplated, including the various methods set forth herein and known in the art. For example, gene expression and protein expression can be assayed or measured by a Northern blot, Western blot, immunoprecipitation assay, or by measuring activity, function or amount of the expressed protein.

The term "interleukin-6 (IL-6)" as used herein refers to an interleukin that acts as both a pro-inflammatory cytokine and an anti-inflammatory myokine. IL-6 is secreted by T cells and macrophages to stimulate immune response, e.g. during infection and after trauma leading to inflammation.

The term "interleukin-6 (IL-6) receptor" as used herein refers to cluster of differentiation 126 (CD126), which is a type I cytokine receptor.

The term "signal transducer and activator of transcription 3 (STAT3)" as used herein refers to a latent transcription factor located in the cytoplasm of cells. Activation of STAT3 depends on the phosphorylation of a conserved tyrosine residue Y705 by upstream kinases, which leads to dimerization, nuclear translocation, DNA binding and gene activation. The term "STAT3 target gene," as used herein, refers to the genes that are downstream in the STAT3 signaling pathway and regulated by STAT3 activation. (Carpenter and Lo, Cancers (Basel,) 2014, June; 6(2):897-925) The STAT3 target genes include, for example, BIRC5, BCL2, HSPA4, BCL2L1 and MCL1. In some embodiments, the expression level of a STAT3 target gene is amplified when STAT3 is activated.

The term "Janus kinase (JAK)" as used herein refers to a family of intracellular, nonreceptor tyrosine kinases that transduce cytokine-mediated signals via the JAK-STAT pathway.

The term "FGF19-mediated" and similar terms, as used in the context of a cancer or tumor, refers to a cancer or tumor that is caused all, or in part, by the expression of FGF19. In certain embodiments, the expression of FGF19 is amplified as compared to a control. In some embodiments, the expression of FGF19 is amplified 5%, 10%, 15%, 20%, 25%, 30%, 35%, 40%, 45%, 50%, 55%, 60%, 65%, 70%, 75%, 80%, 85%, 90%, 95% or more, or any numerical range thereof. In some embodiments, the amplified expression of FGF19 directly results in cancer or tumor, or a symptom thereof. In other embodiments, the amplified expression of FGF19 indirectly results in cancer or tumor, or a symptom thereof.

The term "expression level" as used herein in connection with a gene refers to the amount or accumulation of the expression product of the gene, such as, for example, the amount of a transcription product of the gene (the mRNA level of the gene) or the amount of a translation product of the gene (the protein level of the gene).

The term "control" as used herein refers to a standard level that one can use as a reference to determine the significance of the expression level of a gene in a sample. A control for the expression level of a gene can be the expression level of the gene in a sample from a healthy individual, or the average expression level of the gene in samples from a population of healthy individuals. A control expression level of a gene can also be a cut-off value determined by a person of ordinary skill in the art through statistical analysis of the expression levels of the gene in a sample population.

The term "metabolic function" as used herein, refers to processes necessary for the maintenance of a living organism.

The term "metabolic function of the liver" as used herein, refers to processes in hepatocytes involved in maintaining homeostasis and regulating energy balances in a living organism. As used herein, the term "metabolic function mediated by FGF19" refers to the metabolic function of the liver that is affected directly or indirectly by the FGF19 signaling pathway, and which can include one or more of the ability to regulate bile acid synthesis, regulate glucose levels, regulate insulin sensitivity, regulate insulin resistance, regulate glucose tolerance, regulate glucose metabolism, regulate energy homeostasis, regulate pancreatic function, regulate triglyceride levels, regulate cholesterol levels, regulate blood pressure, and/or regulate weight levels. In one embodiment, the metabolic function mediated by FGF19 can include one or more of the ability to regulate bile acid synthesis, glucose metabolism, and/or energy homeostasis.

The term "antibody" and "immunoglobulin" or "Ig" are used interchangeably herein, and is used in the broadest sense and specifically covers, for example, individual anti-IL-6 or anti-IL-6 receptor monoclonal antibodies (including agonist, antagonist, neutralizing antibodies, full length or intact monoclonal antibodies), anti-IL-6 antibody or anti-IL-6 receptor antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-IL-6 or anti-IL-6 receptor antibodies, and fragments of anti-IL-6 or anti-IL-6 receptor antibodies, as described below. An antibody can be human, humanized, chimeric and/or affinity matured as well as an antibody from other species, for example mouse, rabbit etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See, Borrebaeck (ed.), 1995, *Antibody Engineering, Second Ed.*, Oxford University Press; Kuby, 1997, *Immunology, Third Ed.*, W.H. Freeman and Company, New York). In specific embodiments, the specific molecular antigen that can be bound by an antibody provided herein includes an IL-6 or IL-6 receptor polypeptide, an IL-6 or IL-6 receptor fragment, or an IL-6 or IL-6 receptor epitope. Antibodies also include, but are not limited to, synthetic antibodies, monoclonal antibodies, recombinantly produced antibodies, multispecific antibodies (including bispecific antibodies), human antibodies, humanized antibodies, camelized antibodies, chimeric antibodies, intrabodies, anti-idiotypic (anti-Id) antibodies, and functional fragments (e.g., antigen-binding fragments such as IL-6 or IL-6 receptor binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments such as IL-6 or IL-6 receptor binding fragments) include single-chain Fvs (scFv) (e.g., including monospecific, bispecific, etc.), Fab fragments, F(ab') fragments, F(ab)2 fragments, F(ab')2 fragments, disulfide-linked Fvs (sdFv), Fd fragments, Fv fragments, diabody, triabody, tetrabody and minibody. In particular, antibodies provided herein include immunoglobulin molecules and immunologically active portions of immunoglobulin molecules, for example, antigen-binding domains or molecules that contain an antigen-binding site that binds to IL-6 or an IL-6 receptor antigen (e.g., one or more complementarity determining regions (CDRs) of an anti IL-6 or anti-IL-6 receptor antibody). Such antibody fragments can be found described in, for example, Harlow and Lane, 1989, *Antibodies: A Laboratory Manual*, Cold Spring Harbor Laboratory, New York; Myers (ed.), 1993, *Molec. Biology and Biotechnology: A Comprehensive Desk Reference*, New York: VCH Publisher, Inc.; Huston et al., 1993, *Cell Biophysics*, 22:189-224; Plückthun and Skerra, 1989, *Meth. Enzymol.*, 178:497-515; and in Day, ed., 1990, *Advanced Immunochemistry, Second Ed.*, Wiley-Liss, Inc., New York, N.Y. The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule.

The term "neutralizing" antibody, as used herein, refers to an antibody that binds to an antigen and negates its downstream cellular effects by inhibiting or reducing one or more of its biological activities.

The term "HbA1c" as used herein, refers to a form of hemoglobin that is bound to glucose, and is a risk factor for diabetes if elevated.

The term "responsiveness" or "responsive" as used herein in connection with a treatment refers to the effectiveness of the treatment in lessening or decreasing the symptoms of the disease being treated. For example, a cancer patient is responsive to a treatment if the treatment effectively inhibits the cancer growth, or arrests development of the cancer, causes regression of the cancer, or delays or minimizes one or more symptoms associated with the presence of the cancer in the patient. The responsiveness to a particular treatment of a cancer patient can be characterized as a complete or partial response. "Complete response," or "CR" refers to an absence of clinically detectable disease. "Partial response," or "PR," refers to at least about a 10%, 20%, 30%, 40%, 50%, 60%, 70%, 80%, or 90% decrease in all measurable tumor burden (e.g., the number of malignant cells present in the subject, or the measured bulk of tumor masses) in the absence of new lesions. A person of ordinary skill in the art would understand that clinical standards used to define CR, PR, or other level of patient responsiveness to treatments can vary for different types of cancer.

The term "likelihood" or "likely" as used herein refers to the probability of an event. A subject is "likely" to be responsive to a particular treatment when a condition is met means that the probability of the subject to be responsive to a particular treatment is higher when the condition is met than when the condition is not met. The probability to be responsive to a particular treatment can be higher by, for example, 5%, 10%, 25%, 50%, 100%, 200%, or more in a subject who meets a particular condition compared to a subject who does not meet the condition. For example, a HCC patient is "likely" to be responsive to an anti-IL-6 antibody treatment when the FGF19 expression is amplified means that the probability of a HCC patient to be responsive to an anti-IL-6 antibody treatment is 5%, 10%, 25%, 50%, 100%, 200%, or more higher in a HCC patient having amplified FGF19 expression compared to a HCC patient having normal FGF19 expression.

Fibroblast Growth Factor 19 (FGF19)

Fibroblast growth factors (FGFs) are a family of growth factors that play key roles in cellular proliferation and differentiation. Twenty-two members of the FGF family have been identified in humans, all of which are structurally-related signaling molecules. The FGF19 subfamily of FGFs consists of human FGF21, FGF23, and FGF19 and mouse FGF15.

The physiological effects of FGF family members are the result of heparin-dependent binding to one or more members of the FGF receptor tyrosine kinase (FGFR) family, which includes four members (FGFR1, FGFR2, FGFR3 and FGFR4), each having a tyrosine kinase domain. In addition, each of FGFR1, FGFR2 and FGFR3 also has two splice variants designated as "b" and "c" variants (i.e., FGFR1b, FGFR2b, FGFR3b, FGFR1c, FGFR2c and FGFR3c).

FGF19 targets and has effects on both adipocytes and hepatocytes. Mice treated with recombinant human FGF19, despite being on a high-fat diet, show increased metabolic rates, increased lipid oxidation, a lower respiratory quotient, and weight loss. The metabolic effects of FGF19 occur via its binding to the FGFR1c, FGFR2c and FGFR3c receptors, of which the binding to FGFR1c and FGFR2c are the most significant. FGF19 binding to these receptors requires the co-receptor Klotho-β (KLB).

FGF19 has also been shown to regulate bile production by the liver. Thus, FGF19-like agents can play an important role in bile acid homeostasis.

FGF19 is expressed as a 216 amino acid polypeptide comprising a 22 residue signal peptide (GenBank: AAQ88669.1). Mature human FGF19 (wild-type) is a 194 amino acid polypeptide comprising the following amino acid sequence:

(SEQ ID NO: 1)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK.

A person of ordinary skill in the art would readily be able to identify non-human analogs of FGF19.

FGF19 and Hepatocellular Carcinoma

As described herein, FGF19 is associated with the induction of cancer, particularly HCC, the most common type of liver cancer. Methods of detecting cancers are known in the art.

Various methodologies can be used in the screening and diagnosis of HCC and are well known to the skilled artisan. Indicators for HCC include, but are not limited to, detection of a tumor marker, such as elevated alpha-fetoprotein (AFP) or des-gamma carboxyprothrombin (DCP). A number of different scanning and imaging techniques are also available, including ultrasound, CT scans and MRI. Macroscopically, HCC can be nodular, whereas the tumor nodules (which are frequently round-to-oval, grey or green, well circumscribed but not encapsulated) appear as either one large mass or multiple smaller masses. Alternatively, HCC can be present as an infiltrative tumor which is diffuse and poorly circumscribed and frequently infiltrates the portal veins. Risk factors for HCC include type 2 diabetes (often exacerbated by obesity). The risk of HCC in type 2 diabetics is greater (from ~2.5 to ~7 times the non-diabetic risk) depending on the duration of diabetes and treatment protocol.

Pathological assessment of hepatic tissue samples is generally performed after the results of one or more of the aforementioned methodologies indicate the likely presence of HCC. Thus, certain embodiments of the methods provided herein further include assessing a hepatic tissue sample from an in vivo animal model useful in HCC studies in order to determine whether a polypeptide sequence exhibits evidence of inducing HCC. In certain embodiments, the in vivo animal model is a db/db mouse model. By microscopic assessment, a pathologist can determine whether one of the four general architectural and cytological types (patterns) of HCC are present (i.e., fibrolamellar, pseudoglandular (adenoid), pleomorphic (giant cell), and clear cell).

Therapeutic and Prophylactic Uses

Provided herein are methods for treating or preventing a FGF19-mediated cancer or tumor, or a symptom thereof. Such methods can also have an advantageous effect on one or more symptoms associated with a cancer or tumor, for example, decreasing the severity or the frequency of a symptom. In certain embodiments, the method is a method for treating a FGF19-mediated cancer or tumor. In one embodiment, the method treats the cancer or tumor without substantially affecting the metabolic function of FGF19. As used herein, "substantially" refers to at least about 50%, at least about 60%, at least about 65%, at least about 70%, at least about 75%, at least about 80%, at least about 85%, at least about 90%, at least about 95%, at least about 98%, at least about 99%, or about 100% of the corresponding value. The metabolic function mediated by FGF19 includes one or more of the ability to regulate bile acid synthesis, regulate glucose levels, regulate insulin sensitivity, regulate insulin resistance, regulate glucose tolerance, regulate glucose metabolism, regulate energy homeostasis, regulate pancreatic function, regulate triglyceride levels, regulate cholesterol levels, regulate blood pressure, and/or regulate body weight. In other embodiments, the method is a method for preventing a FGF19-mediated cancer or tumor, or a symptom thereof.

In certain embodiments, the present disclosure contemplates methods of treating a subject having an FGF19-mediated cancer or tumor, or a symptom thereof, the method comprising administering to the subject a therapeutically effective amount of an anti-IL-6 antibody or anti-IL-6 receptor antibody, wherein the FGF19-mediated cancer or tumor, or a symptom thereof, is treated in the subject. In certain embodiments, the administration results in an improvement in the cancer, tumor, or symptom thereof in the subject. In some embodiments, the method results in a reduction in tumor number, tumor size, or tumor weight.

In certain embodiments, the present disclosure contemplates methods of preventing a subject being at risk of developing a FGF19-mediated cancer or tumor, or a symptom thereof, the method comprising administering to the subject a therapeutically effective amount of an anti-IL-6 antibody or anti-IL-6 receptor antibody, wherein the FGF19-mediated cancer or tumor, or a symptom thereof is prevented in the subject. In some embodiments, the administration results in prevention of the cancer, tumor, or symptom thereof in the subject.

In certain embodiments, provided herein is a method of antagonizing the oncogenic activity of FGF19 in a subject, comprising administering to the subject a therapeutically effective amount of an anti-IL-6 antibody or anti-IL-6 receptor antibody, thereby antagonizing the oncogenic activity of FGF19 in the subject.

In certain embodiments, anti-IL-6 antibodies or anti-IL-6 receptor antibodies useful in the methods provided herein include, but are not limited to, siltuximab, tocilizumab, sarilumab, olokizumab, clazakizumab (BMS-945429), elsilimomab, sirukumab, and any combination thereof. In one embodiment, the anti-IL-6 antibody is siltuximab. In one embodiment, the anti-IL-6 receptor antibody is tocilizumab. In another embodiment, the anti-IL-6 antibody or the anti-IL-6 receptor antibody is a neutralizing antibody.

In certain embodiments, the present disclosure contemplates methods of treating a subject having a FGF19-mediated cancer or tumor, or a symptom thereof, the method comprising administering to the subject a therapeutically effective amount of an inhibitor of the STAT3/JAK signaling pathway, wherein the FGF19-mediated cancer or tumor, or a symptom thereof is treated in the subject. In certain embodiments, the administration results in an improvement in the cancer, tumor, or symptom thereof in the subject. In some embodiments, the method results in a reduction in tumor number, tumor size, or tumor weight.

In certain embodiments, the present disclosure contemplates methods of preventing a subject being at risk of developing a FGF19-mediated cancer or tumor, or a symptom thereof, the method comprising administering to the subject a therapeutically effective amount of an inhibitor of the STAT3/JAK signaling pathway, wherein the FGF19-mediated cancer or tumor, or a symptom thereof is prevented in the subject. In some embodiments, the administration results in prevention of the cancer, tumor, or symptom thereof in the subject. In some embodiments, the method results in a reduction in tumor number, tumor size, or tumor weight.

In certain embodiments, provided herein is a method of antagonizing the oncogenic activity of FGF19 in a subject, comprising administering to the subject a therapeutically effective amount of an inhibitor of the STAT3/JAK signaling pathway, thereby antagonizing the oncogenic activity of FGF19 in the subject. In one embodiment, the inhibitors of the STAT3/JAK signaling pathway include, but are not limited to, tofacitinib, ruxolitinib, baricitinib (LY-3009104), filgotinib (G-146034, GLPG-0634), gandotinib (LY-2784544), lestaurtinib (CEP-701), momelotinib (GS-0387, CYT-387), pacritinib (SB1518), upadacitinib (ABT-494), cucurbitacin I (JSI-124), CHZ868, fedratinib (SAR302503), and any combination thereof. In one embodiment, the inhibitor of STAT3/JAK signaling pathway is tofacinitib.

In further embodiments, the disclosure contemplates an anti-IL-6 antibody or anti-IL-6 receptor antibody for use in the treatment of a FGF19-mediated cancer or tumor. In further embodiments thereof, the anti-IL-6 antibody or anti-IL-6 receptor antibody is selected from the group consisting of siltuximab, tocilizumab, sarilumab, olokizumab, clazakizumab (BMS-945429), elsilimomab, sirukumab, and any combination thereof. In one embodiment, the anti-IL-6 antibody is siltuximab. In another embodiment, the anti-IL-6 receptor antibody is tocilizumab.

In additional embodiments, the disclosure contemplates an inhibitor of the STAT3/JAK signaling pathway for use in the treatment of an FGF19-mediated cancer or tumor. In further embodiments, the inhibitor of the STAT3/JAK signaling pathway is selected from the group consisting of tofacinitib, ruxolitinib, baricitinib (LY-3009104), filgotinib (G-146034, GLPG-0634), gandotinib (LY-2784544), lestaurtinib (CEP-701), momelotinib (GS-0387, CYT-387), pacritinib (SB1518), upadacitinib (ABT-494), cucurbitacin 1 (JSI-124), CHZ868, fedratinib (SAR302503) and any combination thereof. In one embodiment, the inhibitor of the STAT3/JAK signaling pathway is tofacinitib.

In further embodiments, the disclosure contemplates the use of an anti-IL-6 antibody or anti-IL-6 receptor antibody in combination with an inhibitor of the STAT3/JAK signaling pathway. In certain embodiments, an anti-IL-6 antibody or anti-IL-6 receptor antibody for use in the treatment of a FGF19-mediated cancer or tumor is selected from the group consisting of siltuximab, tocilizumab, sarilumab, olokizumab, clazakizumab (BMS-9454290), elsilimomab, sirukumab, and any combination thereof. In certain embodiments, an inhibitor of the STAT3/JAK signaling pathway for use in the treatment of a FGF19-mediated cancer or tumor is selected from the group consisting of tofacinitib, ruxolitinib, baricitinib (LY-3009104), filgotinib (G-146034, GLPG-0634), gandotinib (LY-2784544), lestaurtinib (CEP-701), momelotinib (GS-0387, CYT-387), pacritinib (SB1518), upadacitinib (ABT-494), cucurbitacin I (JSI-124), CHZ868, fedratinib (SAR302503) and any combination thereof.

In additional embodiments, the anti-IL-6 antibody or anti-IL-6 receptor antibody and/or the inhibitor of the STAT3/JAK signaling pathway can be co-administered with an anti-tumor agent. In certain embodiments, the anti-tumor agents suitable to be co-administered with the anti-IL-6 antibody or anti-IL-6 receptor antibody or the inhibitor of the STAT3/JAK signaling pathway provided herein include, but are not limited to, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, AR1NOL®); beta-lapachone; lapachol; colchicines; betulinic acid; a camptothecin (including the synthetic analogue topotecan HYCAMTIN®, CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma I and calicheamicin omega II (see, e.g., Agnew, 1994, *Chem Intl. Ed. Engl.*, 33:183-186); dynemicin, including dynemicin A; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN®, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside (Ara-C); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylomithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin, cytotoxic agents useful as antibody drug conjugates, such as maytansinoids (DM1 and DM4, for example) and auristatins (MMAE and MMAF, for example).

In certain embodiments, the anti-IL-6 antibody or anti-IL-6 receptor antibody or the inhibitor of the STAT3/JAK signaling pathway can be used with any cancer treatment known to those skilled in the art.

In certain embodiments, the subject has or is at risk of developing a FGF19-mediated cancer or tumor, or a symptom thereof. In certain embodiments of the disclosure, the cancer or tumor is a liver, lung, breast, colon, esophageal, oral, laryngeal, prostate, bladder, renal, uterine, ovarian, testicular, rectal, pancreas, stomach, brain, or thyroid cancer or tumor. In certain embodiments, the cancer or tumor is a liver, lung, breast, colon, or esophageal cancer or tumor. In one embodiment, the cancer or tumor is a liver cancer or tumor. In some embodiments, the FGF19-mediated cancer or tumor is HCC.

In some embodiments, FGF19 is expressed in a primary or metastatic cancer or tumor cell.

In certain embodiments, the subject is a subject in need of prevention or treatment thereof. In certain embodiments of the methods provided herein, the subject is an animal. In other embodiments, the subject is a human.

In some embodiments, methods provided herein further include determining the expression level of FGF19 or a STAT3 target gene in a cancer sample or tumor sample. In some embodiments, the methods provided herein further include obtaining a cancer sample or tumor sample from a subject. In some embodiments, the treatment described herein is administered if the expression of FGF19 or a STAT3 target gene is determined to be amplified as compared to a control in the cancer or tumor. In some embodiments, the treatment described herein is administered if the expression of FGF19 is determined to be amplified as compared to a control in the cancer or tumor of the subject. In some embodiments, the treatment includes administering to the subject a therapeutically effective amount of an anti-IL-6 antibody or an anti-IL-6 receptor antibody. In some embodiments, the treatment is administered if a STAT3 target gene is determined to be amplified as compared to a control in the cancer or tumor of the subject. In some embodiments, the treatment includes administering to the subject a therapeutically effective amount of an inhibitor of STAT3/JAK signaling pathway.

In some embodiments, provided herein are methods of patient selection for a treatment of an anti-IL-6 antibody or an anti-IL-6 receptor antibody. In some embodiments, provided herein are methods of patient selection for a treatment of an inhibitor of STAT3/JAK signaling pathway. In some embodiments, the methods of patient selection can include determining the expression level of FGF19 or a STAT3 target gene in a cancer sample or tumor sample. The methods can further include obtaining a cancer sample or tumor sample from a subject. In some embodiments, the methods provided herein include selecting a subject for treatment if the expression of FGF19 or a STAT3 target gene is determined to be amplified as compared to a control in the cancer or tumor from the subject. In some embodiments, methods of patient selection provided herein include determining the expression level of FGF19 in a cancer sample or tumor sample from a subject, and selecting the subject for an anti-IL-6 antibody or an anti-IL-6 receptor antibody treatment if the FGF19 expression is determined to be amplified as compared to a control. In some embodiments, methods of patient selection provided herein include determining the expression level of a STAT3 target gene in a cancer sample or tumor sample from a subject, and selecting the subject for an inhibitor of STAT3/JAK signaling pathway treatment if the expression of the STAT3 target gene is determined to be amplified as compared to a control.

In some embodiments, provided herein are methods of predicting responsiveness of a cancer or tumor patient to the treatment with an anti-IL-6 antibody or an anti-IL-6 receptor antibody. In some embodiments, provided herein are methods of predicting responsiveness of a cancer or tumor patient to the treatment with an inhibitor of STAT3/JAK signaling pathway. In some embodiments, the methods of predicting responsiveness in a subject include determining the expression level of FGF19 or a STAT3 target gene in a cancer sample or tumor sample from the subject. The methods can further include obtaining a cancer sample or tumor sample from a subject. In some embodiments, provided herein are methods of predicting responsiveness of a subject to an anti-IL-6 antibody or an anti-IL-6 receptor antibody, including determining the expression level of FGF19 in a cancer sample or tumor sample from the subject, and predicting the subject to be likely responsive to the treatment if the FGF19 expression is determined to be amplified as compared to a control. In some embodiments, provided herein are methods of predicting responsiveness of a subject to an inhibitor of STAT3/JAK signaling pathway, including determining the expression level of a STAT3 target gene in a cancer sample or tumor sample from the subject, and predicting the subject to be likely responsive to the treatment if the expression of STAT3 target gene is determined to be amplified as compared to a control.

In some embodiments, the FGF19 expression is amplified in the FGF19-mediated cancer or tumor as compared to a control. In some embodiments, the expression of FGF19 is amplified at least 5%, 10%, 15%, 20%, 25%, 30%, 35%, 40%, 45%, 50%, 55%, 60%, 65%, 70%, 75%, 80%, 85%, 90%, 95%, or more, or any numerical range thereof, as compared to a control. In some embodiments, the expression of FGF19 is amplified at least 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, or any numerical range thereof, as compared to a control. In some embodiments, the expression of FGF19 is amplified at least 50% as compared to a control. In some embodiments, the expression of FGF19 is amplified at least 75% as compared to a control. In some embodiments, the expression of FGF19 is amplified at least 2 fold as compared to a control. In some embodiments, the expression of FGF19 is amplified at least 5 fold as compared to a control. In some embodiments, the expression of FGF19 is amplified at least 10 fold as compared to a control.

In some embodiments, the expression of at least one STAT3 target gene is amplified in the FGF19-mediated cancer or tumor as compared to a control in said cancer or tumor. In some embodiments, the expression of the STAT3 target gene is amplified at least 5%, 10%, 15%, 20%, 25%, 30%, 35%, 40%, 45%, 50%, 55%, 60%, 65%, 70%, 75%, 80%, 85%, 90%, 95% or more, or any numerical range thereof, as compared to a control. In some embodiments, the expression of the STAT3 target gene is amplified at least 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, or any numerical range thereof, as compared to a control. In some embodiments, the expression of the STAT3 target gene is amplified at least 50% as compared to a control. In some embodiments, the expression of the STAT3 target gene is amplified at least 75% as compared to a control. In some embodiments, the expression of the STAT3 target gene is amplified at least 2 fold as compared to a control. In some embodiments, the expression of the STAT3 target gene is amplified at least 5 fold as compared to a control. In some embodiments, the expression of the STAT3 target gene is amplified at least 10 fold as compared to a control.

In some embodiments, the STAT3 target gene can be BIRC5, BCL2, HSPA4, BCL2L1, MCL1, or any combination thereof. In some embodiments, the STAT3 target gene can be BIRC5. In some embodiments, the STAT3 target gene can be BCL2. In some embodiments, the STAT3 target gene can be HSPA4. In some embodiments, the STAT3 target gene can be BCL2L1. In some embodiments, the STAT3 target gene can be MCL1. In some embodiments, methods provided herein include determining the expression levels of at least one STAT3 target gene. In some embodiments, methods provided herein include determining the expression levels of at least two STAT3 target genes. In some embodiments, methods provided herein include determining the expression levels of at least three STAT3 target genes. In some embodiments, methods provided herein include determining the expression levels of at least four STAT3 target genes. In some embodiments, methods provided herein include determining the expression levels of at least five STAT3 target genes. In some embodiments, method provided herein include determining the expression levels of BIRC5, BCL2, and HSPA4.

In some embodiments, methods of determining the expression level of FGF19 or a STAT3 target gene in a sample includes determining the mRNA level of FGF19 or the STAT3 target gene. Methods of determining the mRNA level can be Quantitative Polymerase Chain Reaction (qPCR), Real-Time Polymerase Chain Reaction (RT-PCR), RNA-seq, Microarray, Serial Analysis of Gene Expression (SAGE), MassARRAY technique, or Fluorescence In Situ Hybridization (FISH). In some embodiments, the mRNA level is determined by Quantitative Real-Time PCR (qRT-PCR).

mRNA may be isolated from the starting tissue sample. General methods for mRNA extraction are well known in the art and are disclosed in standard textbooks of molecular biology, including Ausubel et al., 1997, *Current Protocols of Molecular Biology*, John Wiley and Sons. In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTER-PURE® Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

A sensitive and flexible quantitative method is PCR. Examples of PCR methods can be found in the literature. Examples of PCR assays can be found in U.S. Pat. No. 6,927,024. Examples of RT-PCR methods can be found in U.S. Pat. No. 7,122,799. A method of fluorescent in situ PCR is described in U.S. Pat. No. 7,186,50.

In some embodiments, the first step in gene expression profiling by PCR is the reverse transcription of the RNA template into cDNA, followed by its exponential amplification in a PCR reaction. In other embodiments, a combined reverse-transcription-polymerase chain reaction (RT-PCR) reaction may be used, e.g., as described in U.S. Pat. Nos. 5,310,652; 5,322,770; 5,561,058; 5,641,864; and 5,693,517. The two commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP™ RNA PCR kit (Perkin Elmer, Calif., USA), following the manufacturer's instructions. The derived cDNA can then be used as a template in the subsequent PCR reaction.

In some embodiments, Real-Time Reverse Transcription-PCR (qRT-PCR) can be used for both the detection and quantification of RNA targets (Bustin, et al., 2005, *Clin. Sci.*, 109:365-379). Examples of qRT-PCR-based methods can be found, for example, in U.S. Pat. No. 7,101,663. Instruments for real-time PCR, such as the Applied Biosystems 7500, are available commercially, as are the reagents, such as TaqMan Sequence Detection chemistry.

Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, describe alternative methods for detecting the degradation of probe which occurs concomitant with amplification. 5'-Nuclease assay data may be initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and P-actin.

PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W., 2002, *Genome Res.* 12(4): 656-64, or by the BLAST software including its variations. Subsequent steps follow well established methods of PCR primer and probe design.

It is noted, however, that other nucleic acid amplification protocols (i.e., other than PCR) may also be used in the nucleic acid analytical methods described herein. For example, suitable amplification methods include ligase chain reaction (see, e.g., Wu & Wallace, 1988, *Genomics*, 4:560-569; strand displacement assay (see, e.g., Walker et al., 1992, *Proc. Natl. Acad. Sci. USA*, 89:392-396; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., 1989, *Proc. Natl. Acad. Sci. USA*, 86: 1173-1177); and self-sustained sequence replication (3SR) (Guatelli et al., 1990, Proc. Natl. Acad. Sci. USA, 87: 1874-1878; International Publication No. WO 92/08800). Alternatively, methods that amplify the probe to detectable levels can be used, such as Q-replicase amplification (Kramer & Lizardi, 1989, *Nature*, 339:401-402; Lomeli et al., 1989, *Clin. Chem.* 35: 1826-1831). A review of known amplification methods is provided, for example, by Abramson and Myers, 1993, *Current Opinion in Biotechnology*, 4:41-47.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes.

RNA-Seq, also called Whole Transcriptome Shotgun Sequencing (WTSS) refers to the use of high-throughput sequencing technologies to sequence cDNA in order to get information about a sample's RNA content. Publications describing RNA-Seq include: Wang et al., 2009, *Nature Reviews Genetics*, 10(1):57-63; Ryan et al., 2008, *BioTechniques*, 45(1):81-94; and Maher et al., 2009, *Nature*, 458 (7234):97-101.

Differential gene expression can also be identified, or confirmed using the microarray technique. In this method, polynucleotide sequences of interest (including cDNAs and oligonucleotides) are plated, or arrayed, on a microchip substrate. The arrayed sequences are then hybridized with specific DNA probes from cells or tissues of interest.

In an embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., 1996, *Proc. Natl. Acad. Sci. USA*, 93(2): 106-149). Microarray analysis can be performed by commercially available equipment, following manufacturer's protocols, such as by using the Affymetrix GENCHIP™ technology, or Incyte's microarray technology.

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al. 1995, *Science*, 270:484-487; and Velculescu et al, 1997, *Cell*, 88:243-51.

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dispensed on a chip array that is pre-loaded with the components needed for MALTI-TOF MS sample preparation. The various cDNAs present in the reaction are quantitated by analyzing the peak areas in the mass spectrum obtained.

mRNA level can also be measured by an assay based on hybridization. A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Any suitable assay platform can be used to determine the mRNA level in a sample. For example, an assay can be in the form of a dipstick, a membrane, a chip, a disk, a test strip, a filter, a microsphere, a slide, a multiwell plate, or an optical fiber. An assay system can have a solid support on which a nucleic acid corresponding to the mRNA is attached. The solid support can have, for example, a plastic, silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

In some embodiments, methods of determining the expression level of FGF19 or a STAT3 target gene in a sample includes determining the protein level of FGF19 or the STAT3 target gene. Methods of determining the protein level can be an immunohistochemistry (IHC) approach, an immunoblotting (IB) assay, flow cytometry (FACS), or Enzyme-Linked Immunosorbent Assay (ELISA). In some embodiments, the protein level is measured by an immunoblotting assay.

IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody.

Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Ten, eds., 7th ed. 1991).

Commonly used assays to detect protein level of a gene include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum or bone marrow.

A wide range of immunoassay techniques using such an assay format are available, see, e.g., U.S. Pat. Nos. 4,016, 043, 4,424,279, and 4,018,653. These include both single-site and two-site or "sandwich" assays of the non-competitive types, as well as in the traditional competitive binding assays. These assays also include direct binding of a labeled antibody to a target protein. Sandwich assays are commonly used assays. A number of variations of the sandwich assay technique exist. For example, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample.

In some embodiments, flow cytometry (FACS) can be used to detect the protein level of a gene. Surface proteins (such as IL-6 receptor) can be detected using antibodies against them. The flow cytometer detects and reports the intensity of the fluorochrome-tagged antibody, which indicates the expression level of the gene. Non-fluorescent cytoplasmic proteins can also be observed by staining permeabalized cells. The stain can either be a fluorescence compound able to bind to certain molecules, or a fluorichrome-tagged antibody to bind the molecule of choice.

An alternative method involves immobilizing the target gene in the sample and then exposing the immobilized target to specific antibody, which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by a labeled reporter molecule.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of the gene product present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art and are discussed herein.

It is understood that any of the therapeutic or prophylactic methods provided herein can be used in conjunction with any other methods provided herein.

Pharmaceutical Compositions

The pharmaceutical compositions of the present disclosure can be in the form of compositions suitable for administration to a subject. Such compositions are "pharmaceutical compositions" for treating a FGF19-mediated cancer or tumor, or a symptom thereof, comprising one or more anti-IL-6 antibodies or anti-IL-6 receptor antibodies, or STAT3/JAK signaling pathway inhibitors and one or more pharmaceutically acceptable or physiologically acceptable diluents, carriers or excipients. In certain embodiments, the inhibitors are present in a therapeutically acceptable amount. The pharmaceutical compositions can be used in the methods of the present disclosure; thus, for example, the pharmaceutical compositions can be administered ex vivo or in vivo to a subject in order to practice the therapeutic and prophylactic methods described herein.

The pharmaceutical compositions for treating a FGF19-mediated cancer or tumor, or a symptom thereof, typically comprise a therapeutically effective amount of at least one of anti-IL-6 antibodies or anti-IL-6 receptor antibodies, or STAT3/JAK signaling pathway inhibitors and one or more pharmaceutically and physiologically acceptable formulation diluents, carriers or excipients. The pharmaceutical compositions can comprise one or more anti-IL-6 antibodies or anti-IL-6 receptor antibodies and one or more STAT3/JAK signaling pathway inhibitors in combination with one or more pharmaceutically and physiologically acceptable formulation diluents, carriers or excipients. The pharmaceutical composition may comprise a therapeutically effective amount of at least one of anti-IL-6 antibodies or anti-IL-6 receptor antibodies, or STAT3/JAK signaling pathway inhibitors in combination with an anti-tumor agent, further in combination with one or more pharmaceutically and physiologically acceptable formulation diluents, carriers or excipients.

In certain embodiments, anti-tumor agents suitable to be co-administered with the anti-IL-6 antibody or anti-IL-6 receptor antibody or the inhibitor of the STAT3/JAK signaling pathway provided herein include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, AR1NOL®); beta-lapachone; lapachol; colchicines; betulinic acid; a camptothecin (including the synthetic analogue topotecan HYCAMTIN®, CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma I and calicheamicin omega II (see, e.g., Agnew, 1994, *Chem Intl. Ed. Engl.*, 33:183-186); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN®, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2', 2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside (Ara-C); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin, cytotoxic agents useful as antibody drug conjugates, such as maytansinoids (DM1 and DM4, for example) and auristatins (MMAE and MMAF, for example).

Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-hydroxyethyl)piperazine-N'-(2-ethanesulfonic acid) (HEPES), 2-(N-morpholino)ethanesulfonic acid (MES), 2-(N-morpholino) ethanesulfonic acid sodium salt (MES), 3-(N-morpholino) propanesulfonic acid (MOPS), and N-tris[hydroxymethyl] methyl-3-aminopropanesulfonic acid (TAPS).

After a pharmaceutical composition has been formulated, it can be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus can be used to deliver the pharmaceutical compositions disclosed in the instant disclosure. Depot injections, which are generally administered subcutaneously or intramuscularly, can also be utilized to release the pharmaceutical compositions disclosed herein over a defined period of time.

The pharmaceutical compositions can be in the form of a sterile injectable aqueous or oleaginous suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent, for example, as a solution in 1,3-butanediol. Acceptable diluents, solvents and dispersion media that can be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose, any bland fixed oil can be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient can be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use can be prepared according to any method known to the art for the manufacture of pharmaceutical compositions, and such compositions can contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients can be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration can be uncoated or coated by known techniques to delay disintegration and absorption in the gastrointestinal tract and thereby provide a sustained action. For example, a time-delay material such as glyceryl monostearate or glyceryl distearate can be employed. They can also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrylate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501,728, and 4,837,028. Methods for the preparation of the above-mentioned formulations will be apparent to those skilled in the art.

Formulations for oral use can also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions can also contain one or more preservatives.

Oily suspensions can be formulated by suspending the active ingredient in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure can also be in the form of oil-in-water emulsions. The oily phase can be a vegetable oil, for example olive oil or arachis oil, or a mineral oil, for example, liquid paraffin, or mixtures of these. Suitable emulsifying agents can be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs, and microencapsulated delivery systems. For example, a time delay material such as glyceryl monostearate or glyceryl stearate alone, or in combination with a wax, can be employed.

The concentration of IL-6 inhibitors, IL-6 receptor inhibitors, or STAT3/JAK inhibitors in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of the IL-6 antibodies or IL-6 receptor antibodies, or STAT3/JAK pathway inhibitors, and compositions thereof, in any appropriate manner. Suitable routes of administration include parenteral (e.g., intramuscular, intravenous, subcutaneous (e.g., injection or implant), intraperitoneal, intracisternal, intraarticular, intracerebral (intraparenchymal and intracerebroventricular), oral, nasal, vaginal, sublingual, intraocular, rectal, topical (e.g., transdermal), sublingual and inhalation. In certain embodiments, the antibodies or the inhibitors can be administered parenterally, for example, by infusion, subcutaneously, intramuscularly, intravenously, intradermally, intrathecally and epidurally. The dose will vary, including depending on the nature and/or severity of the disease or disorder as well as the condition of the subject.

In certain embodiments, the antibodies or the inhibitors can be administered parenterally or orally.

Dosing

In certain embodiments, the anti-IL-6 antibodies or anti-IL-6 receptor antibodies, or STAT3/JAK pathway inhibitors useful in the methods disclosed herein, can be administered to a subject in an amount that is dependent upon, for example, the goal of the administration (e.g., the degree of resolution desired); the age, weight, sex, health, and physical condition of the subject to be treated; the nature of the formulation being administered; the route of administration; and the nature of the disease, disorder, condition or symptom thereof (e.g., the severity of the hepatocellular carcinoma). The dosing regimen can also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with "absorption, distribution, metabolism, and excretion" (ADME), taking into consideration the route of administration and other factors.

An "effective dose" (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

An appropriate dosage level of antibody administered intravenously is generally about 0.1 to 100 mg/kg of patient body weight per day, which can be administered in single or multiple doses. In some embodiments, the dosage level is about 1 to about 50 mg/kg per day, and in other embodiments about 5 to about 25 mg/kg per day. Suitable particular dosages can be about 1 mg/kg per day, about 5 mg/kg per day, about 10 mg/kg per day, about 15 mg/kg per day, about 20 mg/kg per day, about 25 mg/kg per day, or about 50 mg/kg per day. The dosage can be repeated as a 1-hour IV infusion from every 1 week to every 5 weeks. In one embodiment, the dosage can be repeated every 3 weeks.

An appropriate dosage level of siltuximab administered intravenously is generally about 0.1 to 100 mg/kg of patient body weight per day, which can be administered in single or multiple doses. In some embodiments, the dosage level is about 1 to about 50 mg/kg per day, and in other embodiments about 5 to about 25 mg/kg per day. Suitable particular dosages can be about 1 mg/kg per day, about 5 mg/kg per day, about 10 mg/kg per day, about 11 mg/kg per day, about 15 mg/kg per day, about 20 mg/kg per day, about 25 mg/kg per day, or about 50 mg/kg per day. The dosage can be repeated as a 1-hour IV infusion from every 1 week to every 5 weeks. In one embodiment, the dosage can be repeated every 3 weeks.

An appropriate dosage level of tocilizumab administered intravenously is generally about 0.1 to 100 mg/kg of patient body weight per day, which can be administered in single or multiple doses. In some embodiments, the dosage level is about 1 to about 50 mg/kg per day, in other embodiments about 4 to about 30 mg/kg per day, and in other embodiments about 8 to about 25 mg/kg per day. Suitable particular dosages can be about 1 mg/kg per day, about 4 mg/kg per day, about 8 mg/kg per day, about 10 mg/kg per day, about 12 mg/kg per day, about 15 mg/kg per day, about 20 mg/kg per day, about 25 mg/kg per day, or about 50 mg/kg per day. The dosage can be repeated from every 2 weeks to every 6 weeks. In one embodiment, the dosage can be repeated every 4 weeks.

An appropriate dosage level of inhibitors of STAT3/JAK signaling pathway administered orally in the form of tablets, capsules and the like contains from 0.1 to 1000 mg per day, particularly 0.1, 0.25, 0.5, 0.75, 1.0, 1.25, 2.5, 5.0, 7.5, 10.0, 11.0, 15.0, 20.0, 25.0, 50.0, 75.0, 100.0 mg per day. Tofacitinib can be administered on a regimen of, for example, twice per day, once per day, once every other day, or once a week.

An appropriate dosage level of tofacitinib administered orally in the form of tablets, capsules and the like contains from 0.1 to 1000 mg per day, particularly 0.1, 0.25, 0.5, 0.75, 1.0, 1.25, 2.5, 5.0, 7.5, 10.0, 11.0, 15.0, 20.0, 25.0, 50.0, 75.0, 100.0 mg per day. Tofacitinib can be administered on a regimen of, for example, twice per day, once per day, once every other day, or once a week.

In certain embodiments, the dosage of the anti-IL-6 antibodies or anti-IL-6 receptor antibodies, or the STAT3/JAK inhibitors are contained in a "unit dosage form." The phrase "unit dosage form" refers to physically discrete units, each unit containing a predetermined amount of an active ingredient of the present disclosure sufficient to produce the desired effect. It will be appreciated that the parameters of a unit dosage form depend on the particular agent and the effect to be achieved. Exemplary unit doses can range from about 25-250; 250-500; 500-1,000; 1,000-2,500; 2,500-5,000; 5,000-25,000; or 25,000-50,000 ng; or from about 25-250; 250-500; 500-1,000; 1,000-2,500; 2,500-5,000; 5,000-25,000; 25,000-50,000 µg; or from about 25-250; 250-500; 500-1,000; 1000-2,500; 2,500-5,000; 5,000-25,000; or 25,000-50,000 mg.

Single or multiple doses can be administered, for example, multiple times per day, on consecutive days, alternating days, weekly or intermittently (e.g., twice per week, once every 1, 2, 3, 4, 5, 6, 7 or 8 weeks, or once every 2, 3, 4, 5 or 6 months).

Kits

Provided herein are kits comprising the anti-IL-6 antibodies or anti-IL-6 receptor antibodies, or the inhibitors of STAT3/JAK signaling pathway, and pharmaceutical compositions comprising thereof that are suitable for administration to a subject. The kits are generally in the form of a physical structure housing various components, as described below, and can be utilized, for example, in practicing the methods described above.

Kits provided herein can further include devices that are used to administer the anti-IL-6 antibodies or anti-IL-6 receptor antibodies, or the inhibitors of STAT3/JAK signaling pathway. Examples of such devices include, but are not limited to, syringes, drip bags, patches, and inhalers. Kits can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

A kit can contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert can be, e.g., integrated into the physical structure housing the components, contained separately within the physical structure, or affixed to a component of the kit (e.g., an ampoule, tube or vial). Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

Provided herein are also kits for predicting the responsiveness of a cancer or tumor to an anti-IL-6 antibody or anti-IL-6 receptor antibody treatment, or an inhibitor of the STAT3/JAK signaling pathway, including at least one agent for determining the expression level of FGF19 or of a STAT3 target gene. The kits can also include an ancillary agent. In some embodiments, provided herein are kits for predicting the responsiveness of a cancer or tumor to an anti-IL-6 antibody or anti-IL-6 receptor antibody treatment, including at least one agent for determining the expression level of FGF19, and an ancillary agent. In some embodiments, provided herein are kits for predicting the responsiveness of a cancer or tumor to an inhibitor of the STAT3/JAK signaling pathway, including at least one agent for determining the expression level of a STAT3 target gene, and an ancillary agent.

In certain embodiments, the cancer or tumor is a liver, lung, breast, colon, esophageal, oral, laryngeal, prostate, bladder, renal, uterine, ovarian, testicular, rectal, pancreas, stomach, brain, or thyroid cancer or tumor. In certain embodiments, the cancer or tumor is a liver, lung, breast, colon, or esophageal cancer or tumor. In one embodiment, the cancer or tumor is a liver cancer or tumor. In some embodiments, the FGF19-mediated cancer or tumor is HCC.

In some embodiments, the kits further include reagents for mRNA isolation or purification means, detection means, as well as positive and negative controls. In certain embodiments, the kits further include instructions for users. In some embodiments, the kits further include a pharmaceutical composition described herein. The kits can be tailored for in-home use, clinical use, or research use. In some embodiments, the kits further include a label describing its use as a companion diagnostic for predicting the responsiveness of a cancer or tumor to an anti-IL-6 antibody or anti-IL-6 receptor antibody treatment, or an inhibitor of the STAT3/JAK signaling pathway.

The kits provided herein can employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide.

In some embodiments, the kits can include, a computer program product embedded on computer readable media for predicting the responsiveness of a cancer or tumor to anti-an IL-6 antibody or anti-IL-6 receptor antibody treatment, or an inhibitor of the STAT3/JAK signaling pathway. In some embodiments, the kits can include a computer program product embedded on a computer readable media along with instructions.

In certain embodiments of the methods and kits provided herein, solid phase supports are used for purifying gDNA, labeling samples or carrying out the solid phase assays. Examples of solid phases suitable for carrying out the methods disclosed herein include beads, particles, colloids, single surfaces, tubes, multiwell plates, microtiter plates, slides, membranes, gels and electrodes. When the solid phase is a particulate material (e.g., beads), it is, in one embodiment, distributed in the wells of multi-well plates to allow for parallel processing of the solid phase supports.

The kit of this disclosure can include an ancillary reagent. In some embodiments, the ancillary reagent can be a detection reagent, a detection buffer, an immobilization buffer, a dilution buffer, a washing buffer, or any combination thereof.

Any detection reagent known in the art can be included in a kit of this disclosure. In some embodiments, the detection reagent is a colorimetric detection reagent, a fluorescent detection reagent, or a chemiluminescent detection reagent. In some embodiments, the colorimetric detection reagent includes PNPP (p-nitrophenyl phosphate), ABTS (2,2'-azino-bis(3-ethylbenzothiazoline-6-sulphonic acid)) or OPD (o-phenylenediamine). In some embodiments, the fluorescent detection reagent includes QuantaBlu™ or QuantaRed™ (Thermo Scientific, Waltham, Mass.). In some embodiments, the luminescent detection reagent includes luminol or luciferin. In some embodiments, the detection reagent includes a trigger (e.g., H2O2) and a tracer (e.g., isoluminol-conjugate).

Any detection buffer known in the art can be included in a kit of this disclosure. In some embodiments, the detection buffer is a citrate-phosphate buffer (e.g., about pH 4.2).

Any stop solution known in the art can be included in a kit of this disclosure. The stop solutions of this disclosure terminate or delay the further development of the detection reagent and corresponding assay signals. Stop solutions can include, for example, low-pH buffers (e.g., glycine-buffer, pH 2.0), chaotrophic agents (e.g., guanidinium chloride, sodium-dodecylsulfate (SDS)) or reducing agents (e.g., dithiothreitol, mecaptoethanol), or the like.

In some embodiments, the ancillary reagent is an immobilization reagent, which can be any immobilization reagent known in the art, including covalent and non-covalent immobilization reagents. Covalent immobilization reagents can include any chemical or biological reagent that can be used to covalently immobilize a peptide or a nucleic acid on a surface. Covalent immobilization reagents can include, for example, a carboxyl-to-amine reactive group (e.g., carbodiimides such as EDC or DCC), an amine reactive group (e.g., N-hydroxysuccinimide (NHS) esters, imidoesters), a sulfhydryl-reactive crosslinker (e.g., maleimides, haloacetyls, pyridyl disulfides), a carbonyl-reactive crosslinker groups (e.g., hydrazides, alkoxyamines), a photoreactive crosslinker (e.g., aryl azides, dizirines), or a chemoselective ligation group (e.g., a Staudinger reaction pair). Non-covalent immobilization reagents include any chemical or biological reagent that can be used to immobilize a peptide or a nucleic acid non-covalently on a surface, such as affinity tags (e.g., biotin) or capture ragents (e.g., streptavidin or anti-tag antibodies, such as anti-His6 or anti-Myc antibodies).

The kits of this disclosure can include combinations of immobilization reagents. Such combinations include, for example, EDC and NHS, which can be used, for example, to immobilize a protein of this disclosure on a surface, such as a carboxylated dextrane matrix (e.g., on a BIAcore™ CM5 chip or a dextrane-based bead). Combinations of immobilization reagents can be stored as premixed reagent combinations or with one or more immobilization reagents of the combination being stored separately from other immobilization reagents.

A large selection of washing buffers are known in the art, such as tris(hydroxymethyl)aminomethane (Tris)-based buffers (e.g., Tris-buffered saline, TBS) or phosphate buffers (e.g., phosphate-buffered saline, PBS). Washing buffers can include detergents, such as ionic or non-ionic detergents. In some embodiments, the washing buffer is a PBS buffer (e.g., about pH 7.4) including Tween®20 (e.g., about 0.05% Tween®20).

Any dilution buffer known in the art can be included in a kit of this disclosure. Dilution buffers can include a carrier protein (e.g., bovine serum albumin, BSA) and a detergent (e.g., Tween®20). In some embodiments, the dilution buffer is PBS (e.g., about pH 7.4) including BSA (e.g., about 1% BSA) and Tween®20 (e.g., about 0.05% Tween®20).

In some embodiments, the kit of this disclosure includes a cleaning reagent for an automated assay system. An automated assay system can include systems by any manufacturer. In some embodiments, the automated assay systems include, for example, the BIO-FLASH™, the BEST 2000™, the DS2™, the ELx50 WASHER, the ELx800 WASHER, and the ELx800 READER. A cleaning reagent can include any cleaning reagent known in the art.

In a particular embodiment, provided herein is a kit for predicting the responsiveness of a HCC patient to siltuximab or tofacitinib, including an agent to determine the expression level of FGF19, and an ancillary agent in a sample from the patient.

Screening Methods

The present disclosure also contemplates a method for determining whether an anti-IL-6 antibody or anti-IL-6 receptor antibody is a candidate for treating a subject having a FGF19-mediated cancer or tumor, or a symptom thereof, the method comprising: (a) administering an anti-IL-6 antibody or anti-IL-6 receptor antibody to a test subject, wherein the amount of the anti-IL-6 antibody or anti-IL-6 receptor antibody administered to the subject is sufficient to reduce the number of macroscopically detectable tumors in the subject, and (b) determining whether the reduction of the number of macroscopically detectable tumors is observed in the subject; wherein the reduced number of macroscopically detectable tumors indicates that the anti-IL-6 antibody or anti-IL-6 receptor antibody is a candidate for treatment of the subject.

The present disclosure also contemplates a method for determining whether an anti-IL-6 antibody or anti-IL-6 receptor antibody is a candidate for treating a subject having a FGF19-mediated cancer or tumor, or a symptom thereof, the method comprising: (a) administering an anti-IL-6 antibody or anti-IL-6 receptor antibody to a test subject, wherein the amount of the anti-IL-6 antibody or anti-IL-6 receptor antibody administered to the subject is sufficient to reduce an average tumor load in the subject, and (b) determining whether the reduction of the average tumor load is observed in the subject; wherein the reduced tumor load indicates that the anti-IL-6 antibody or anti-IL-6 receptor antibody is a candidate for treatment of the subject.

The present disclosure also contemplates a method for determining whether an inhibitor of the STAT3/JAK signaling pathway is a candidate for treating a subject having a FGF19-mediated cancer or tumor, or a symptom thereof, the method comprising: (a) administering an inhibitor of the STAT3/JAK signaling pathway to a test subject, wherein the amount of the inhibitor of the STAT3/JAK signaling pathway administered to the subject is sufficient to reduce the number of macroscopically detectable tumors in the subject, and (b) determining whether the reduction of the number of macroscopically detectable tumors is observed in the subject; wherein the reduced number of macroscopically detectable tumors indicates that the inhibitor of the STAT3/JAK signaling pathway is a candidate for treatment of the subject.

The present disclosure also contemplates a method for determining whether an inhibitor of the STAT3/JAK signaling pathway is a candidate for treating a subject having a FGF19-mediated cancer or tumor, or a symptom thereof, the method comprising: (a) administering an inhibitor of the STAT3/JAK signaling pathway to a test subject, wherein the amount of the inhibitor of the STAT3/JAK signaling pathway administered to the subject is sufficient to reduce an average tumor load in the subject, and (b) determining whether the reduction of the average tumor load is observed in the subject; wherein the reduced tumor load indicates that the inhibitor of the STAT3/JAK signaling pathway is a candidate for treatment of the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

In case of conflict, the specification, including definitions, will control. As used herein and in the appended claims, the singular forms "a," "an," and "the" include plural referents unless the context clearly dictates otherwise. Thus, for example, reference to a "treatment," includes a plurality of such treatments, and so forth. It is further noted that the claims can be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges, unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1000, 1000-2500, 2500-5000, 5000-25,000, or 5000-50,000 includes any numerical value or range within or encompassing such values, e.g., 25, 26, 27, 28, 29 . . . 250, 251, 252, 253, 254 . . . 500, 501, 502, 503, 504 . . . , etc. The use of a series of ranges includes combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

Selected Embodiments

In embodiment 1, provided is a method of treating or preventing a fibroblast growth factor 19 (FGF19)-mediated cancer or tumor in a subject in need thereof, comprising administering to the subject a therapeutically effective amount of an anti-interleukin-6 (anti-IL-6) antibody or an anti-IL-6 receptor antibody.

In embodiment 2, provided is the method of embodiment 1, wherein the anti-IL-6 antibody or anti-IL-6 receptor antibody is a neutralizing antibody.

In embodiment 3, provided is the method of embodiment 1, wherein the anti-IL-6 antibody or anti-IL-6 receptor antibody is selected from the group consisting of siltuximab, tocilizumab, sarilumab, olokizumab, clazakizumab (BMS-945429), elsilimomab, and sirukumab.

In embodiment 4, provided is the method of embodiment 3, wherein the anti-IL-6 antibody is siltuximab.

In embodiment 5, provided is the method of embodiment 3, wherein the anti-IL-6 receptor antibody is tocilizumab.

In embodiment 6, provided is the method of any one of embodiments 1 to 5, wherein the dose of siltuximab or tocilizumab is in the range of about 0.1 to 100 mg/kg/day.

In embodiment 7, provided is the method of embodiment 6, wherein the dose of siltuximab is in the range of about 5 to about 25 mg/kg/day.

In embodiment 8, provided is the method of embodiment 7, wherein the dose of siltuximab is about 5 mg/kg per day, about 10 mg/kg per day, about 11 mg/kg per day, about 15 mg/kg per day.

In embodiment 9, provided is the method of embodiment 6, wherein the dose of tocilizumab is in the range of about 4 to about 30 mg/kg/day.

In embodiment 10, provided is the method of embodiment 9, wherein the dose of tocilizumab is about 4 mg/kg per day, about 8 mg/kg per day, about 10 mg/kg per day, about 12 mg/kg per day.

In embodiment 11, provided is the method of any one of embodiments 1 to 10, wherein siltuximab or tocilizumab is administered by intravenous infusion.

In embodiment 12, provided is the method of embodiment 11, wherein siltuximab or tocilizumab is administered once every 3 or 4 weeks.

In embodiment 13, provided is the method of any of embodiments 1 to 12, wherein the administration treats the cancer or tumor without substantially affecting a metabolic function mediated by FGF19.

In embodiment 14, provided is the method of embodiment 13, wherein the metabolic function is one or more of the ability to regulate bile acid synthesis, glucose metabolism, and/or energy homeostasis.

In embodiment 15, provided is the method of any one of embodiments 1 to 14, wherein the FGF19-mediated cancer or tumor is a liver, lung, breast, colon, or esophageal cancer or tumor.

In embodiment 16, provided is the method of any one of embodiments 1 to 14, wherein the FGF19-mediated cancer or tumor is a liver cancer or tumor.

In embodiment 17, provided is the method of embodiment 16, wherein the liver cancer or tumor is hepatocellular carcinoma (HCC).

In embodiment 18, provided is the method of any one of embodiments 1 to 17, wherein the subject is a human.

In embodiment 19, provided is the method of any one of embodiments 1 to 18, wherein the FGF19 expression is amplified as compared to a control in said cancer or tumor.

In embodiment 20, provided is a method of claim 19, comprising determining the expression level of FGF19 in said cancer or tumor.

In embodiment 21, provided is a method of claim 20, wherein the expression level of FGF19 in said cancer or tumor is determined by qPCR, RT-PCR, RNA-seq, microarray analysis, SAGE, MassARRAY technique, FISH, an immunohistochemistry (IHC) assay, an immunoblotting assay, flow cytometry (FACS), or ELISA.

In embodiment 22, provided is a method of treating or preventing a FGF19-mediated cancer or tumor in a subject in need thereof comprising administering to the subject a therapeutically effective amount of an inhibitor of signal transducer and activator of transcription 3 (STAT3)/Janus kinase (JAK) signaling pathway.

In embodiment 23, provided is the method of embodiment 22, wherein the inhibitor of STAT3/JAK signaling pathway is selected from the group consisting of tofacitinib, ruxolitinib, baricitinib (LY-3009104), filgotinib (G-146034, GLPG-0634), gandotinib (LY-2784544), lestaurtinib (CEP-701), momelotinib (GS-0387, CYT-387), pacritinib (SB1518), upadacitinib (ABT-494), cucurbitacin I (JSI-124), CHZ868, and fedratinib (SAR302503).

In embodiment 24, provided is the method of embodiment 23, wherein the inhibitor of STAT3/JAK signaling pathway is tofacitinib.

In embodiment 25, provided is the method of embodiment 24, where the dose of tofacitinib is in the range of 0.1 to 1000 mg per day.

In embodiment 26, provided is the method of embodiment 25, wherein the dose of tofacitinib is about 1.0, 2.5, 5.0, 7.5, 10.0, 11.0, or 15.0 mg per day.

In embodiment 27, provided is the method of any one of embodiments 23 to 26, wherein tofacitinib is administered orally.

In embodiment 28, provided is the method of embodiment 27, wherein tofacitinib is administered once or twice daily.

In embodiment 29, provided is the method of any one of embodiments 22 to 28, wherein the administration treats the cancer or tumor without substantially affecting the metabolic function mediated by FGF19.

In embodiment 30, provided is the method of embodiment 29, wherein the metabolic function is one or more of the ability to regulate bile acid synthesis, glucose metabolism, and/or energy homeostasis.

In embodiment 31, provided is the method of any one of embodiments 22 to 30, wherein the FGF19-mediated cancer or tumor is a liver, lung, breast, colon or esophageal cancer or tumor.

In embodiment 32, provided is the method of any one of embodiments 22 to 30, wherein the FGF19-mediated cancer or tumor is a liver cancer or tumor.

In embodiment 33, provided is the method of embodiment 32, wherein the liver cancer or tumor is hepatocellular carcinoma (HCC).

In embodiment 34, provided is the method of any one of embodiments 22 to 33, wherein the subject is a human.

In embodiment 35, provided is the method of any one of embodiments 22 to 34, wherein the expression of at least one STAT3 target gene is amplified as compared to a control in said cancer or tumor.

In embodiment 36, provided is the method of embodiment 35, wherein said STAT3 target gene is selected from the group consisting of BIRC5, BCL2, HSPA4, BCL2L1 and MCL1.

In embodiment 37, provided is the method of embodiment 35 or 36, wherein the expression level of FGF19 in said cancer or tumor is determined by qPCR, RT-PCR, RNA-seq, microarray analysis, SAGE, MassARRAY technique, FISH, an immunohistochemistry (IHC) assay, an immunoblotting assay, flow cytometry (FACS), or ELISA.

In embodiment 38, provided is a method of modulating FGF19 signaling in a liver cell, the method comprising contacting the cell with an anti-IL-6 antibody or an anti-IL-6 receptor antibody.

In embodiment 39, provided is a method of modulating FGF19 signaling in a liver cell, the method comprising contacting the cell with an inhibitor of the STAT3/JAK signaling pathway.

In embodiment 40, provided is an anti-IL-6 antibody or anti-IL-6 receptor antibody for use in the treatment of a FGF19-mediated cancer or tumor.

In embodiment 41, provided is an inhibitor of signal transducer and activator of transcription 3 (STAT3)/Janus kinase (JAK) signaling pathway for use in the treatment of a FGF19-mediated cancer or tumor.

In embodiment 42, provided is a kit for predicting the responsiveness of a cancer or tumor to an anti-IL-6 antibody or an anti-IL-6 receptor antibody treatment, comprising at least one agent for determining the expression level of FGF19 in said cancer or tumor, and an ancillary agent.

In embodiment 43, provided is a kit for predicting the responsiveness of a cancer or tumor to a treatment with an inhibitor of the STAT3/JAK signaling pathway, comprising at least one agent for determining the expression level of a STAT3 target gene in said cancer or tumor, and an ancillary agent.

In embodiment 44, provided is the kit of embodiment 43, wherein said STAT3 target gene is selected from the group consisting of BIRC5, BCL2, HSPA4, BCL2L1 and MCL1.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the descriptions in the Experimental section are intended to illustrate but not limit the scope of invention described in the claims.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; BW=body weight; U=unit; ns=not statistically significant; AAV=adeno-associated virus; FGF19CF=FGF19 with FLAG-tag at the C-terminus; GFP=green fluorescent protein; ELISA=enzyme-linked immunosorbance assay; ANOVA=analysis of variance; SEM=standard error of the mean.

Materials and Methods

The following methods and materials were used in the Examples.

Animals. All experimental procedures were approved by the Institutional Animal Care and Use Committee at NGM. Mice were housed in a pathogen-free animal facility at 22° C. under controlled 12-hour light and 12-hour dark cycles. All mice were maintained in filter-topped cages on standard chow diet (Teklad 2918) or diets containing inhibitors when indicated, and autoclaved water ad libitum. Male mice were used unless otherwise specified. Sample sizes were determined on the basis of homogeneity and consistency of characteristics in the selected models and were sufficient to detect statistically significant differences in tumorigenicity and metabolic parameters between groups. Mice were randomized into the treatment groups based on body weight and blood glucose. All injections and tests were performed during the light cycle. db/db mice, Stat3$^{f/f}$, Il6$^{-/-}$, Mdr2$^{-/-}$ mice, and wild type control C57BL6/J mice were obtained from Jackson Laboratory.

DNA constructs. Human FGF19 cDNA (NM_005117) was subcloned into a pAAV-EF1α vector using SpeI and NotI sites. cDNAs for TBG promoter and Cre recombinase were synthesized (DNA2.1), and subcloned into pAAV vector.

Cell culture. All cells were cultured in a humidified incubator with 5% CO2 and 95% air at 37° C. Cell lines used were confirmed to be *mycoplasma* free. Cells were authenticated by short tandem repeat DNA profiling.

AAV production. AAV293 cells (Agilent Technologies) were cultured in Dulbeco's Modification of Eagle's Medium (DMEM; Mediatech) supplemented with 10% fetal bovine serum and 1× antibiotic-antimycotic solution (Mediatech). The cells were transfected with 3 plasmids (AAV transgene, pHelper (Agilent Technologies) and AAV2/9) for viral production. Viral particles were purified using a discontinuous iodixanal (Sigma) gradient and re-suspended in phosphate-buffered saline (PBS) with 10% glycerol and stored at −80° C. Viral titer or vector genome number was determined by quantitative PCR using custom Taqman assays specific for WPRE sequences. Standard curves for WPRE were obtained from serial dilutions over a 6 log range of the corresponding plasmids. AAV-mediated gene delivery provides a means to achieve long-lasting transgene expression without the inflammatory responses that are commonly associated with other viral vectors. When introduced into adult mice, sustained expression of up to one year has been observed. The primary tissue of transgene expression using this method is liver.

In vivo pSTAT3 activation. Production of recombinant FGF19 protein has been described previously (Zhou et al., 2014, *Cancer Research,* 74:3306-3316). Saline (0.9% NaCl) was used as vehicle for dosing in mice. 11 week old db/db mice were injected intraperitoneally with 1 mg/kg FGF19 protein. Mice were euthanized 2 hours later for serum and liver collection. Liver samples were homogenized in Extraction Buffer I (ThermoFisher) supplemented with Complete Mini protease inhibitor cocktail (Roche) and phosphatase inhibitor cocktail (Sigma). For IL-6 inhibition, mice were intraperitoneally injected with 10 mg/kg anti-mouse IL6 blocking antibody (Bio-X-Cell) or isotype control IgG (Bio-X-Cell). 10 minutes later, mice were dosed with 1 mg/kg FGF19 protein. Livers were collected 2 hours after FGF19 injection for pSTAT3 analysis by western blotting.

In vitro pSTAT3 activation. Primary human hepatocytes were isolated from consenting donors using a modified collagenase/pronase method (BioReclamation/IVT). Cells were diluted in attachment media (DMEM supplemented with 2 mM glutamine, 100 unit/ml penicillin, 100 unit/ml streptomycin, and 10% FBS), and cells were plated on collagen-coated 6-well plate (Becton Dickinson). Four hours later, cells were changed into William's E media containing dexamethasone/T3/insulin and cultured for 16 hours at 37° C. When indicated, 50 ng/ml FGF19 protein or 50 ng/ml human IL-6 (Peprotech) were added.

Primary mouse hepatocytes were isolated from 8-10 week old wild type mice (BioReclamation/IVT). Cells were diluted in attachment media, and cells were plated on collagen-coated 6-well plate (Becton Dickinson). Four hours later, cells were changed into M199 media supplemented with 10% FBS, 2 mM glutamine, 100 unit/ml penicillin, 100 unit/ml streptomycin, and cultured for 16 hours at 37° C. When indicated, 50 ng/ml FGF19 protein or 50 ng/ml mouse IL-6 (Peprotech) were added.

Cell extracts were prepared in 50 mM Tris-Cl, PH 7.2, 150 mM NaCl, 1% NP-40, 0.1% SDS, 0.5% sodium deoxycholate supplemented with a protease inhibitor cocktail (Roche) and phosphatase inhibitors (Sigma, phosphatase inhibitor cocktail set 2 and set 3), and protein concentrations were determined by BCA protein assay (Thermo Scientific).

Immunoblotting. Cell or tissue lysates were mixed with 4×SDS sample loading buffer (50 mM Tris-Cl, pH6.8, 2.5% SDS, urea, 4% β-mercaptoethanol), heated for 10 minutes at 95° C., and separated on 4-20% SDS-polyacrylamide gels (Life Technologies) in 1×MOPS running buffer. Proteins were transferred onto PVDF membranes (GE Healthcare). Membranes were blocked in TBST buffer (20 mM Tris-Cl, pH 7.6, 137 mM NaCl, 0.1% Tween-20) containing 5% non-fat dry milk for 1 hour at room temperature, and incubated with anti-pSTAT3$^{Y705}$, anti-total STAT3, anti-pERK, anti-total ERK, or anti-β-actin antibodies in blocking buffer at 4° C. overnight. Membranes were washed in TBST extensively, and bound proteins were detected with horse-radish peroxidase-conjugated goat-anti-mouse IgG or goat-anti-rabbit IgG antibodies (GE Healthcare) for 1 hour at room temperature. Signals were developed with SuperSignal West Dura extended duration substrate (Thermo Scientific), and captured with a ChemiDoc XrS+ imaging system (Bio-Rad).

In vivo BrdU incorporation. For surgical implant, mice were anesthetized with isoflurane, and osmotic pumps (#1002, Alzet) releasing 8.5 mg/kg/day 5-bromo-2-deoxyuridine (BrdU, Sigma) and 0.4 mg/kg/day FGF19 protein were implanted subcutaneously on the back on day 1. Incisions were closed with surgical clippers and 3-0 silk suture. Mice were euthanized on day 6, and serum and livers were collected for exposure and BrdU incorporation analysis.

In vitro BrdU incorporation. Primary cultures of human or mouse hepatocytes (BioReclamation) were cultured on collagen-coated 96-well plates. $1 \times 10^6$ cells in suspension were plated in attachment media (DMEM+10% FBS+penicillin/streptomycin) for 4 hrs and changed into William's E media with Dex/T3/Ins and cultured for 16 hours at 37° C. When indicated, recombinant hepatocyte growth factor (Peprotech) were added.

Hepatocyte-specific Stat3 deletion. For studies in $Stat3^{f/f}$ mice (#016923, on C57BL6/J background, Jackson Laboratory), 14-18 week old mice received a single intravenous dose of $1 \times 10^{11}$ v.g. of AAV-FGF19 in combination with $3 \times 10^{11}$ v.g. of AAV-Cre recombinase or AAV-GFP through the tail vein. $Stat3^{f/f}$ mice injected with AAV-TBG-Cre alone served as $Stat3^{\Delta Hep}$ controls. $Stat3^{f/f}$ mice were used as wild type controls. AAV-TBG-Cre drives Cre recombinase expression under TBG promoter, which allows hepatocyte-specific expression.

52 weeks after AAV injection, mice were euthanized and examined for liver tumor formation. The maximum diameter of liver tumor nodules in each mouse was measured with a caliper and total numbers of tumor nodules per liver were recorded. Livers were weighed and collected for histological examination or gene expression analysis.

Glucose and body composition. Blood concentrations of ad libitum fed glucose were measured in conscious animals from a hand-held glucometer (Accu-check, Roche Diagnostics) using tail vein blood. Body weight and body composition (EcoMRI whole body composition analyzer) were measured at designated times. Mice were euthanized 52 weeks post-AAV administration. Macroscopic liver tumors were counted and the maximal diameter of the tumors recorded.

Gene expression analysis. Tissues were snap-frozen in liquid nitrogen upon euthanization of animals. Total RNA was extracted using RNeasy Mini kit (Qiagen) and treated with DNase I (Thermo Fisher Scientific). Real-time quantitative PCR assays were performed using 10 ng of total RNA from each sample, QuantiTect multiplex qRT-PCR master mix (Qiagen) and premade Taqman gene expression assays in a total volume of 10 µl. Samples were loaded into an optical 384-well plate and qRT-PCR were performed in triplicates on 7900HT Sequence Detection System (Applied Biosystems). Target gene expression was determined using the comparative threshold cycle method with GAPDH as the internal standard.

Blood parameters. Blood was collected from tail vein in un-anesthetized animals using microvette serum gel tubes (Sarstedt) for measurements of glucose, insulin, ALT, AST, ALP, bile acids, and FGF19 concentrations. Serum samples were prepared by centrifugation at 4° C. for 10 minutes at 6000 g after clotting at room temperature for 30 minutes. For HbA1c measurements, whole blood was collected after euthanasia by cardiac puncture into EDTA-tubes and quickly inverted multiple times. HbA1c (from whole blood samples) and liver enzyme (from serum samples) levels were measured on Cobas Integra 400 Clinical Analyzer (Roche Diagnostics). Serum FGF19 level was determined by FGF19 enzyme-linked immunosorbent assays (ELISA) (Biovendor). Serum insulin was assessed with ELISA kits from ALPCO. Concentrations of total bile acids in serum were determined using a 3β-hydroxysteroid dehydrogenase method (Diazyme). All assays were performed according to the manufacturers' instructions.

Histology and immunohistochemistry. Livers were fixed in 10% neutral-buffered formalin and embedded in paraffin. 5 µm sections were deparaffinized in xylenes, rehydrated sequentially in graded ethanol (100%, 95%, 80%, 70%, 50%, 2 minutes each). Hematoxylin and eosin staining was performed using standard methods. For immunohistochemical studies, liver sections were subjected to antigen retrieval in a citrate-based Antigen Unmasking Solution (Vector Laboratories), and incubated for 30 minutes with 3% $H_2O_2$ at room temperature to block endogenous peroxidase activity. Sections were stained with primary antibodies against glutamine synthetase (Thermo Fisher), BrdU, PCNA, or STAT3 in PBS containing 10% goat serum. Biotinylated secondary antibodies, ABC-HRP reagent (Vectastain ABC kit, #PK-6100, Vector Laboratories) and di-amine-benzidine (DAB) colorimetric peroxidase substrate (#SK-4100, Vector Laboratories) were used for detection. When indicated, sections were counterstained with hematoxylin. Digital imaging microscopy was performed using a Leica DM4000 microscope equipped with DFC500 camera and a scanning platform (Leica). Images for the entire liver section were acquired by stitching 70-96 fields together using Surveyor program for morphometric analysis. Glutamine synthetase-positive tumor areas were quantified using Measure/Count/Area tool from ImagePro software.

Isolation of liver non-parenchymal cells. Livers were minced in RPMI media containing 0.1% collagenase for 30 minutes at 37° C. and passed through a 70 µm cell strainer. Hepatocytes were removed by centrifugation at 50 g for 15 minutes. Non-parenchymal cells were collected by centrifugation at 500 g for 10 minutes.

Flow cytometry. For quantification of BrdU incorporation by flow cytometry, livers were minced in RPMI media containing 0.1% collagenase for 30 minutes at 37° C. and passed through 70 µm filter. BD BrdU kit 7-AAD. Cells were analyzed on a BD Caliper flow cytometer and data were collected using CellQuest software and analyzed using Flowjo program.

For intracellular IL-6 staining, isolated hepatic non-parenchymal cells were incubated in DMEM+GolgiPlug and cultured at 37° C. overnight. Cells were washed and resuspended in FACS buffer (PBS containing 2% fetal calf serum and 0.1% azide). Non-specific binding was blocked by Mouse Fc Blocker (2.4G2, eBioscience, 1:100) for 30 minutes on ice. Cells were subsequently stained with fluorophore-labeled antibodies (CD45, clone 30F-11; CD3, clone 17A2; CD19, clone 6D5, CD11b, clone M1/70, Ly6-G, clone 1A8; NK1.1, clone PK136; F4/80, clone BM8), or isotype-control antibodies for 30 minutes at 4° C. in the dark. Live/Dead Dapi kit was used to gate out dead cells. Surface-stained cells were fixed and permeabilized using Fix/Perm Buffer set (eBioscience) and incubated with anti-IL-6 in 1×Perm buffer or isotype control antibody for 60 minutes at 4° C. in the dark. Cells were analyzed on a BD FACS Fortessa flow cytometer configured with five lasers and data were collected using FACSDiva software and analyzed using Flowjo programs.

Tumorigenicity study in IL-6-deficient mice. $Il6^{-/-}$ mice were backcrossed to C57BL/6 mice for at least nine generations. Age and gender-matched wild type C57BL6 mice were used as $Il6^{+/+}$ controls. $1 \times 10^{11}$ v.g. of AAV-FGF19 or AAV-GFP were injected intravenously in a volume of 200 µl saline. Body weight, body composition, and blood glucose were measured at designated times. Mice were euthanized 52 weeks post-AAV administration for liver tumor assessment.

Tumorigenicity study in db/db mice. 11 to 12 week old db/db mice received a single intravenous dose of AAV containing either FGF19 or a control gene (green fluorescent protein). Body weight and blood glucose were monitored. For AAV-SOCS3 inhibition, mice were co-injected with AAV-FGF19 (5×10$^9$ v.g.) and AAV-SOCS3 (5×10$^{19}$ v.g.). For tofacitinib treatment, chow diet containing 0.01% tofacitinib was started 4 weeks post AAV-FGF19 (1×10$^{11}$ v.g.) injection and continued ad libitum for 20 additional weeks. Mice were euthanized 24 weeks post-AAV administration and examined for liver tumor formation by gross appearance and histology.

Anti-IL-6 treatment in Mdr2$^{-/-}$ mice. Four month-old female Mdr2$^{-/-}$ mice received a single intravenous dose of 1×10$^{11}$ v.g. of AAV-FGF19. Anti-IL-6 treatment started 14 weeks after AAV injection. Mice were dosed with anti-mouse IL-6 antibody (Bio-X-Cell) or an isotype control antibody (Bio-X-Cell) once weekly i.p. at 10 mg/kg for a total of 10 doses. Mice were euthanized 24 weeks post-AAV administration for liver tumor assessment. When indicated, Mdr2$^{-/-}$ mice injected with AAV-GFP serve as controls for evaluating serum levels of liver enzymes.

Statistical Analysis. All results are expressed as mean+SEM. One-way ANOVA followed by Dunnett's post-test was used to compare data from multiple groups (GraphPad Prism). When indicated, unpaired two-tailed Student's t-test was used to compare two treatment groups. A P-value of 0.05 or less was considered statistically significant.

Example 1

Non-Cell Autonomous Activation of Hepatic STAT3 by FGF19

To examine STAT3 activation following FGF19 treatment in vivo, 11 week old diabetic db/db mice (on BKS background) were administered with 1 mg/kg of recombinant FGF19 protein i.p., and livers were harvested after 2 hours. Phosphorylation of STAT3 at tyrosine residue 705 (pSTAT3$^{Y705}$) was evident by immunoblotting of liver lysates (FIG. 1A). Total STAT3 and β-actin served as loading controls. FGF19 also induced phosphorylation at threonine-202 and tyrosine-204 of extracellular signal-regulated kinases ERK1 and ERK2 in the liver.

Figure 1B:
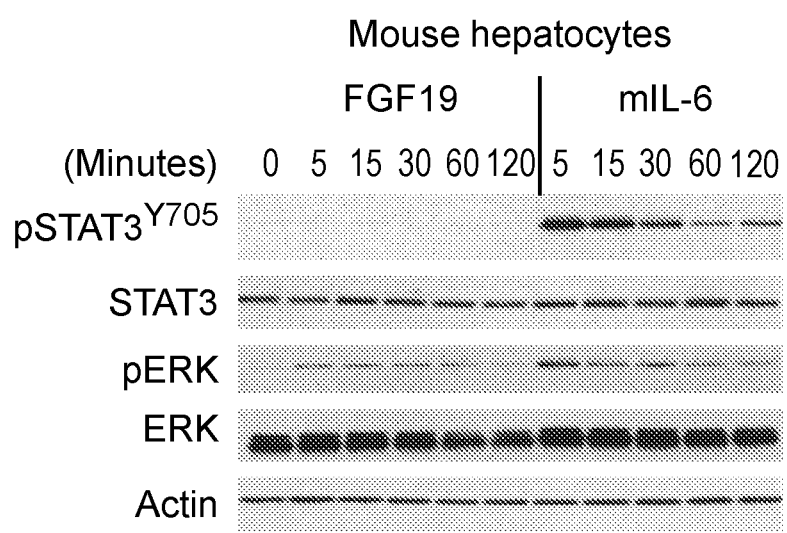
Figure 1C:
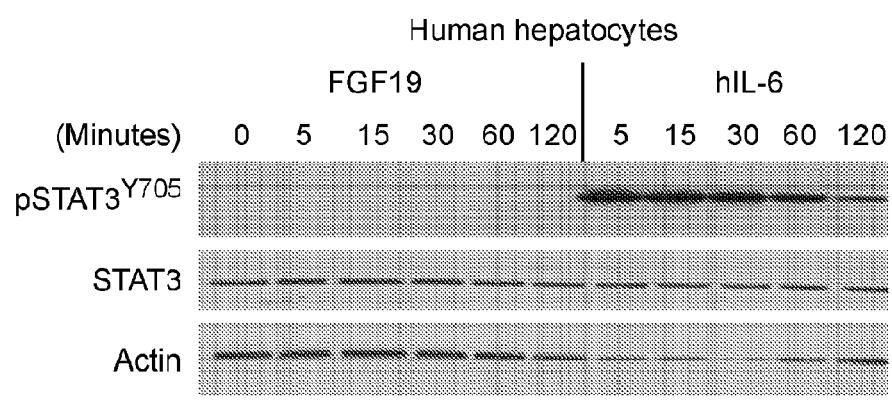
Figure 8A:
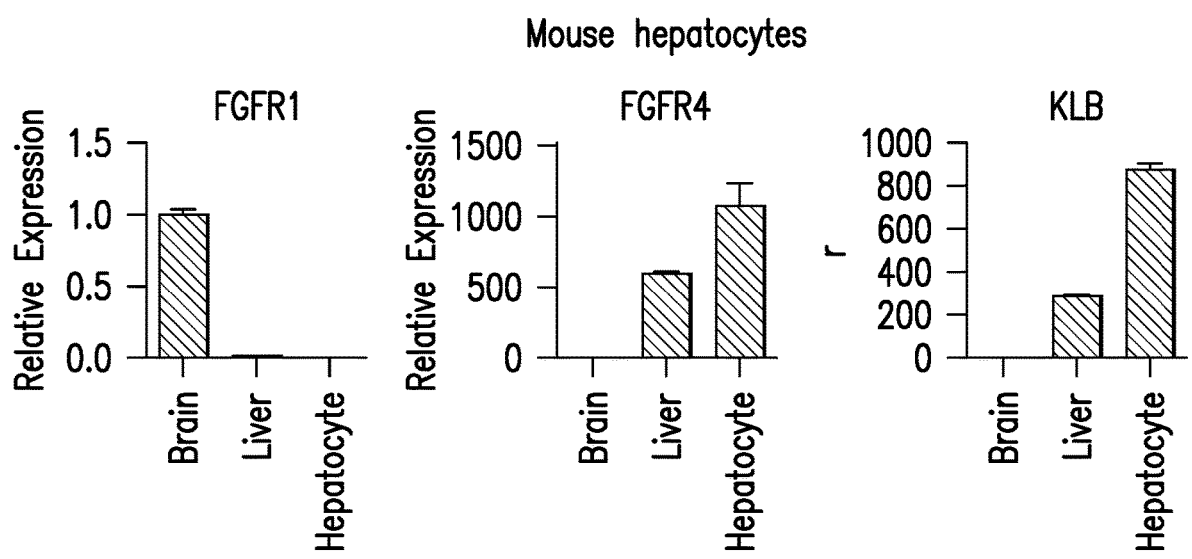
FIGS. 8A-8B depict the expression of FGFR1, FGFR4 and KLB on hepatocytes.
Figure 8B:
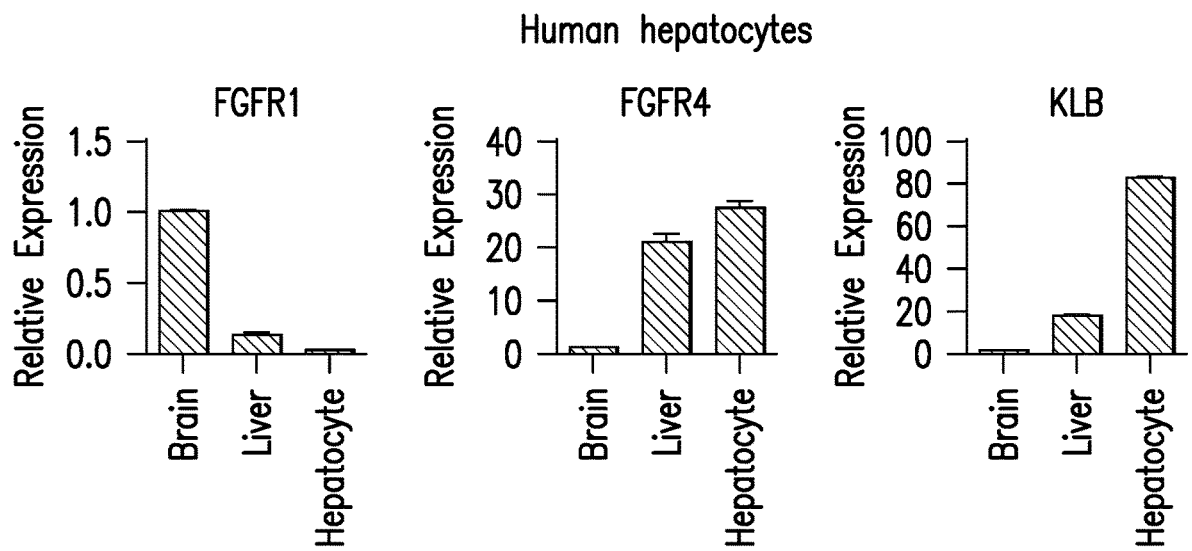

To investigate an in vitro direct effect of FGF19 on STAT3 activation in isolated hepatocytes, pSTAT3$^{Y705}$ levels in primary cultures of hepatocytes upon FGF19 stimulation were analyzed by western blotting. Hepatocytes were purified from adult mice by collagenase treatment followed by gradient centrifugation and confirmed to express FGF19 receptors FGFR4 and KLB (FIGS. 1B and 8A). Cell lysates were prepared at the indicated time points following FGF19 stimulation and analyzed for phosphorylation of the various proteins. In marked contrast to the observations in vivo, treatment with recombinant FGF19 protein did not enhance STAT3 phosphorylation in isolated mouse hepatocytes. As a positive control, robust elevated phosphorylation of pSTAT3$^{Y705}$ were observed following IL-6 treatment in these cells. The lack of STAT3 activation by FGF19 was also confirmed in purified primary human hepatocytes (FIGS. 1C and 8B).

Phosphorylation of ERK1 and ERK2 was apparent in primary cultures of mouse hepatocytes treated with FGF19 (FIG. 1B), similar to observations in vivo (FIG. 1A), indicating that ERK activation by FGF19 is likely a cell autonomous event.

These contradicting in vivo and in vitro observations are consistent with non-cell autonomous activation of STAT3 by FGF19, pointing to the possibility that FGF19-triggered STAT3 phosphorylation depends on the microenvironment in the liver.

Example 2

Non-Cell Autonomous Induction of Hepatocellular Proliferation by FGF19

Figure 2A:
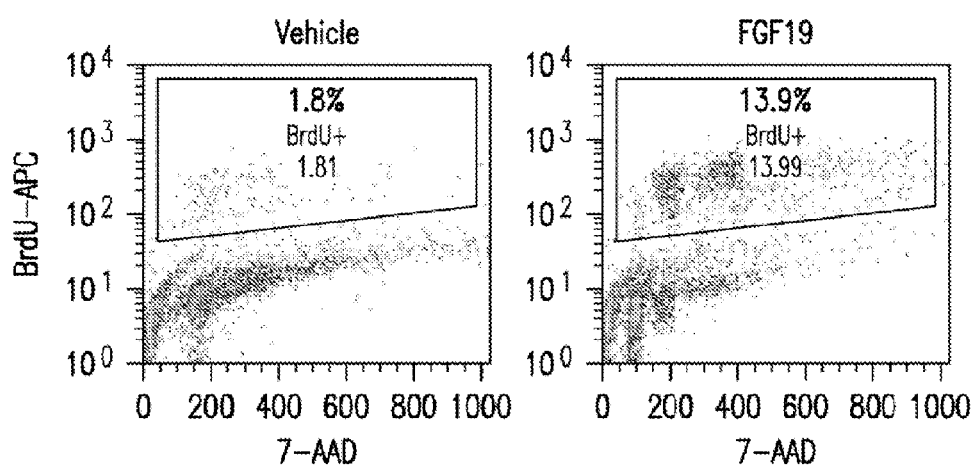
FIGS. 2A-2E depict non-cell autonomous promotion of hepatocellular proliferation by FGF19. 11 week old mice (n=5 per group) were implanted with osmotic pumps releasing BrdU (8.5 mg/kg/day) and FGF19 protein (0.4 mg/kg/day). Livers were harvested 6 days post-implant.
Figure 2B:
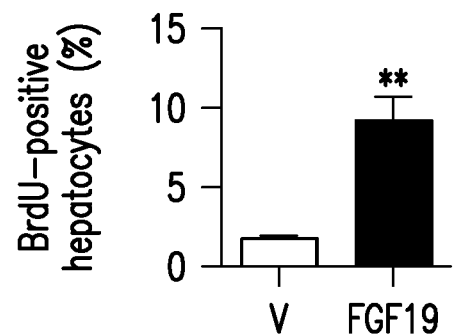
Figure 2C:
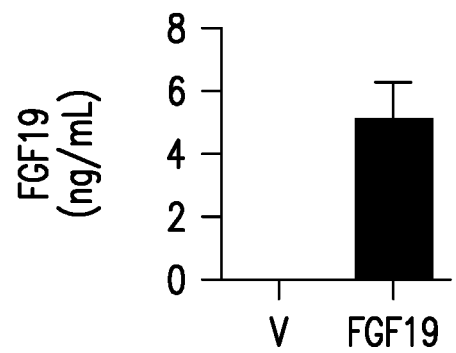

To determine the direct effect of FGF19 on hepatocyte proliferation in a cell autonomous manner, the proliferative effects of FGF19 in vivo and in isolated hepatocytes were compared by assessing the incorporation of 5-bromo-2-deoxyuridine (BrdU) into newly synthesized DNA. FGF19 was administered at a concentration of 0.4 mg/kg/day and BrdU was administered at 8.5 mg/kg/day. After being administered to mice for six days through an osmotic pump, recombinant FGF19 protein induced incorporation of BrdU into hepatocytes as evidenced by immunohistochemical staining (with hematoxylin) and by flow cytometry analysis (hepatocytes were stained with 7-AAD and anti-BrdU-APC) (FIGS. 2A and 2B). At a dose of 20 μg per mouse per day, FGF19-treated livers contain significantly more BrdU-positive cells (9.2+1.5%) than control livers (1.7+0.2%) (FIG. 2B). Consistent with this result, proliferating cell nuclear antigen (PCNA) and Ki-67 expression were higher in FGF19-treated mice. Plasma concentrations of FGF19 were 5.2±1.2 ng/mL at the end of the study (FIG. 2C).

Figure 2D:
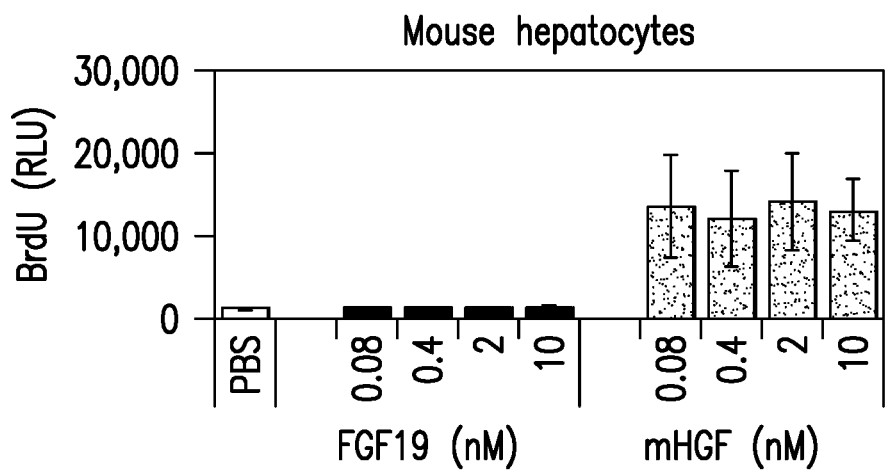
Figure 2E:
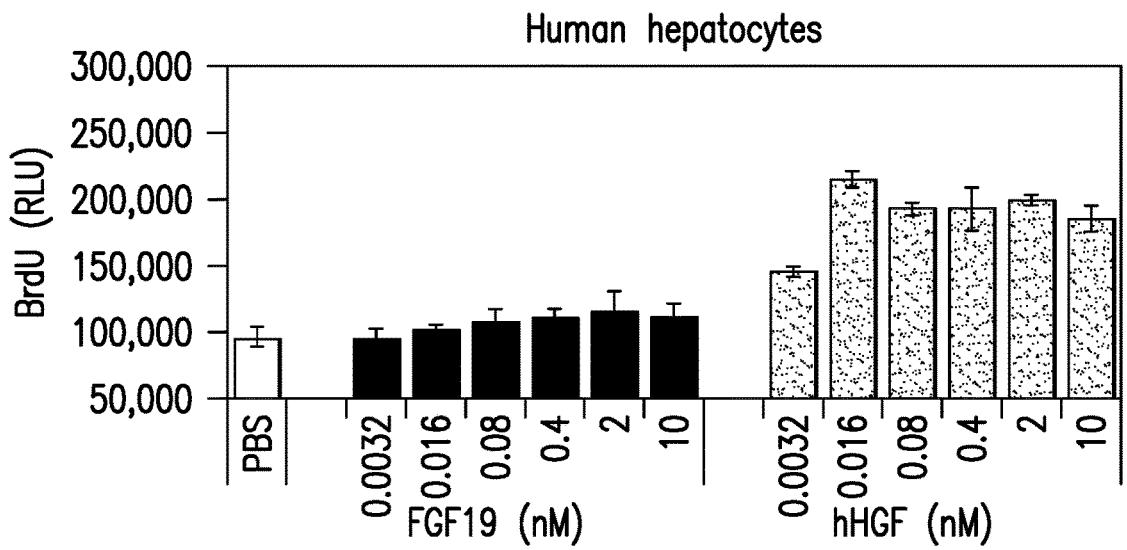

Incubation of the primary cultures of hepatocytes isolated from mouse livers with increasing concentrations of FGF19 resulted in no increase in BrdU signal (FIG. 2D). In contrast, stimulation with hepatocyte growth factor (HGF) elicited strong BrdU signals. The lack of direct proliferative effect by FGF19 was confirmed in purified primary human hepatocytes (FIG. 2E).

These observations suggest that FGF19-induced hepatocyte proliferation in vivo involves non-cell autonomous collaboration between hepatocytes and non-parenchymal microenvironment of the liver.

Example 3

Hepatocellular STAT3 is Essential for the Initiation and Progression of Hepatocellular Carcinomas Mediated by FGF19

Figure 3A:
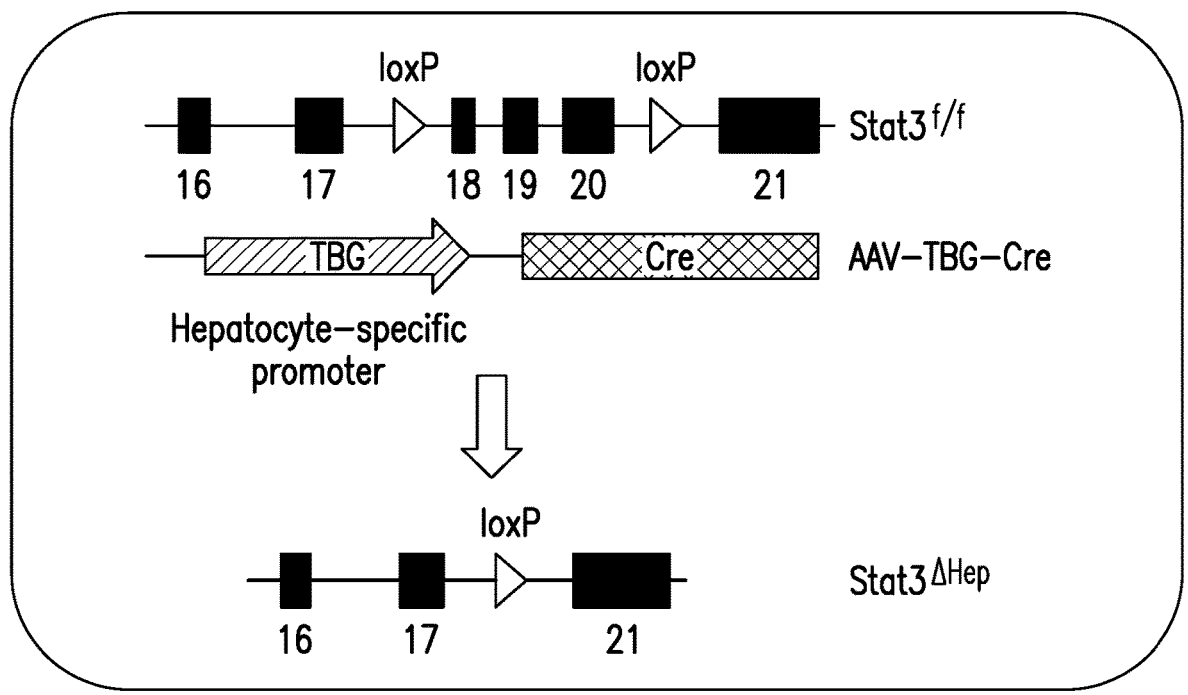
FIGS. 3A-3F depict hepatocyte-specific ablation of STAT3 eliminates FGF19-associated tumorigenicity.

To evaluate the impact of STAT3 in FGF19-mediated tumorigenesis, STAT3 expression was deleted in hepatocytes. Recombinant AAV carrying Cre recombinase under the control of a hepatocyte-specific, thyroxine-binding globin (TBG) promoter (Carrillo-Carrasco et al., 2010, Human Gene Therapy, 21:1147-1154) was injected intravenously into mice harboring LoxP sites flanking exon 18, 19, and 20 of the Stat3 gene (Stat3$^{f/f}$ mice) (Moh et al., 2007, Laboratory Investigation: J Tech Methods and Path, 87:1018-1028) (FIG. 3A). The ablation of Stat3 in the resulting hepatocyte-specific Stat3-deficient mice (Stat3$^{\Delta Hep}$) was confirmed by immunohistochemical analysis (immunohistochemical staining with anti-STAT3 followed by DAB substrates).

Figure 3B:
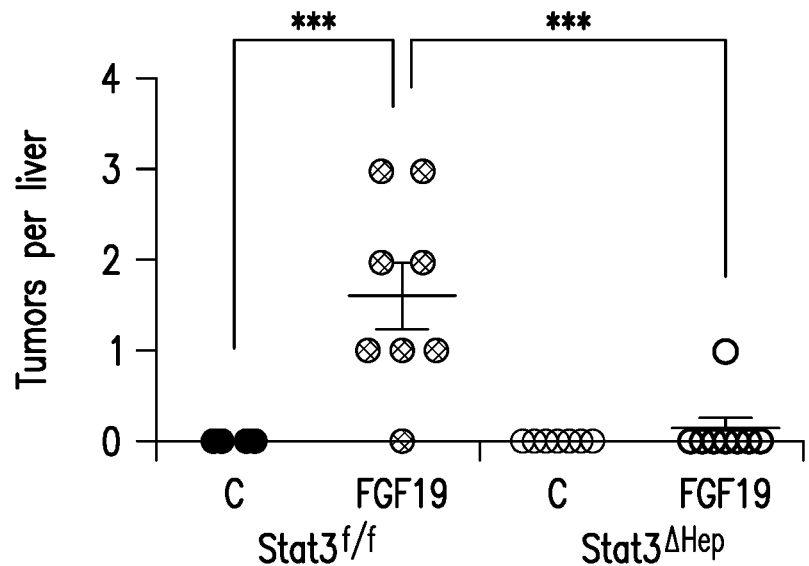
Figure 3C:
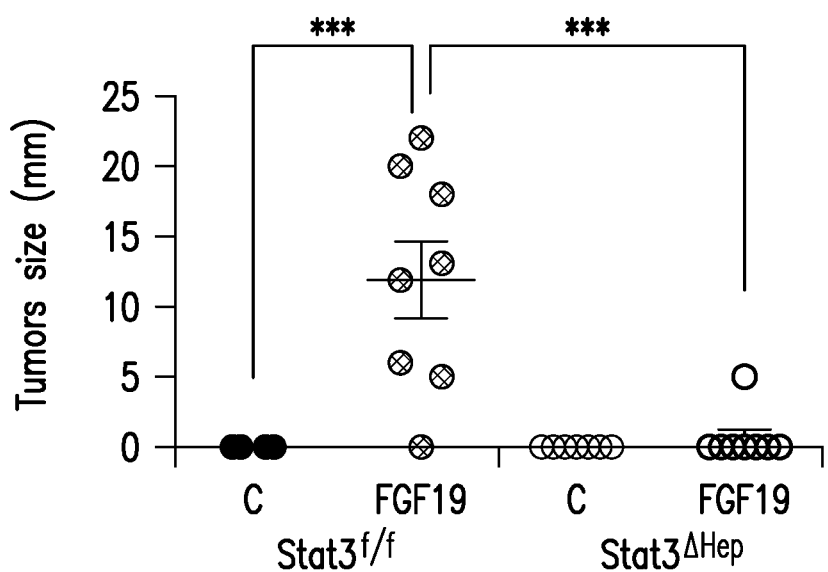
Figure 3D:
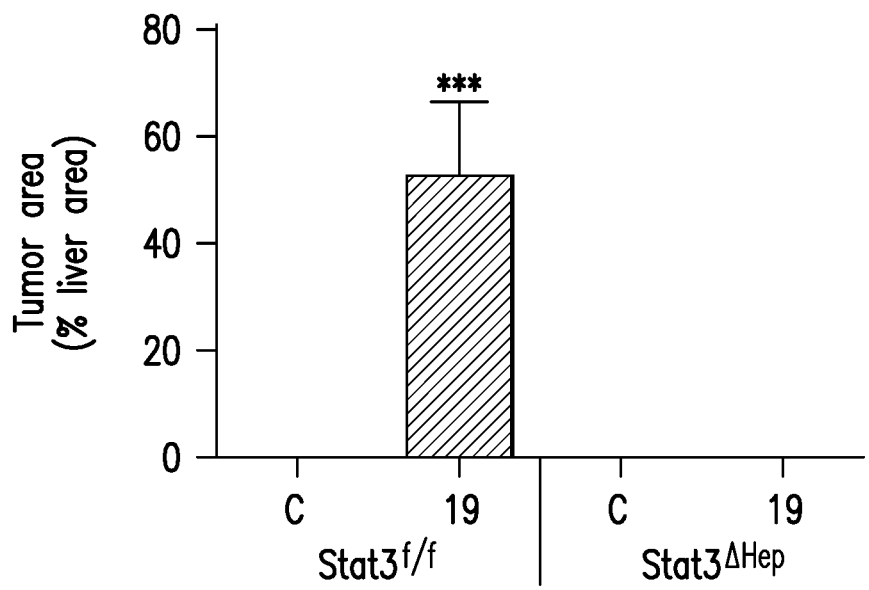
Figure 3E:
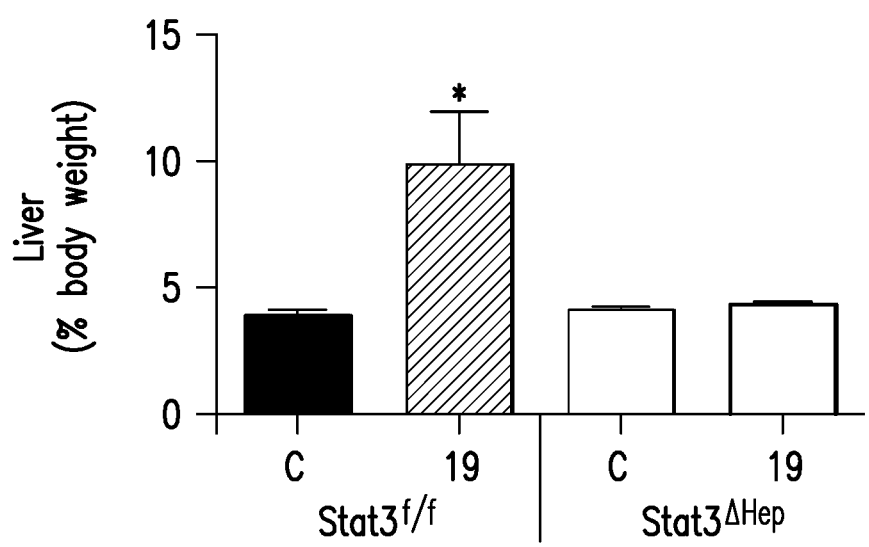
Figure 3F:
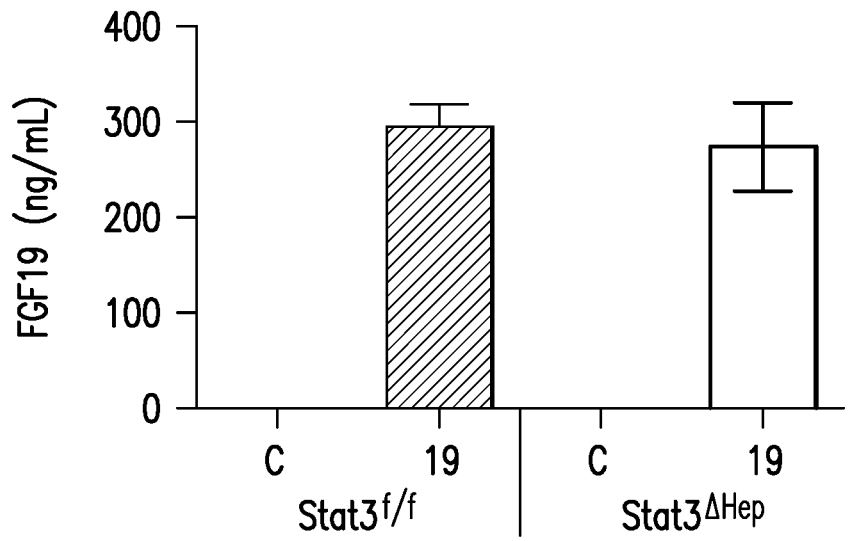

Following a single tail vein injection of 1×10$^{11}$ genome copies of viral particles, ~90% of Stat3$^{f/f}$ mice developed hepatocellular carcinomas 12 months after intravenous injection of AAV-FGF19 (FIGS. 3B and 3C). In contrast, tumor incidence, tumor multiplicity, and tumor size were all markedly reduced in age-matched Stat3$^{\Delta Hep}$ mice even after 12 months of continuous exposure to AAV-expressed FGF19 (FIGS. 3B and 3C). Histological analysis revealed that glutamine synthetase-positive HCC tumors developed exclusively in FGF19-expressing Stat3$^{f/f}$ mice, but were not observed in Stat3$^{\Delta Hep}$ mice expressing FGF19 (FIG. 3D), suggesting that Stat3 deficiency in hepatocytes prevents HCC initiation and progression in response to FGF19. FGF19 expression increased liver-to-body weight ratios in Stat3$^{f/f}$ mice, but not in Stat3$^{\Delta He}$p mice (FIG. 3E). Concentrations of FGF19 in the sera of these mice were measured by ELISA at the end of the study, and found to be 292±29 ng/mL and 275±47 ng/mL in Stat3$^{f/f}$ and Stat3$^{\Delta Hep}$ genotypes, respectively (FIG. 3F).

Figure 9A:
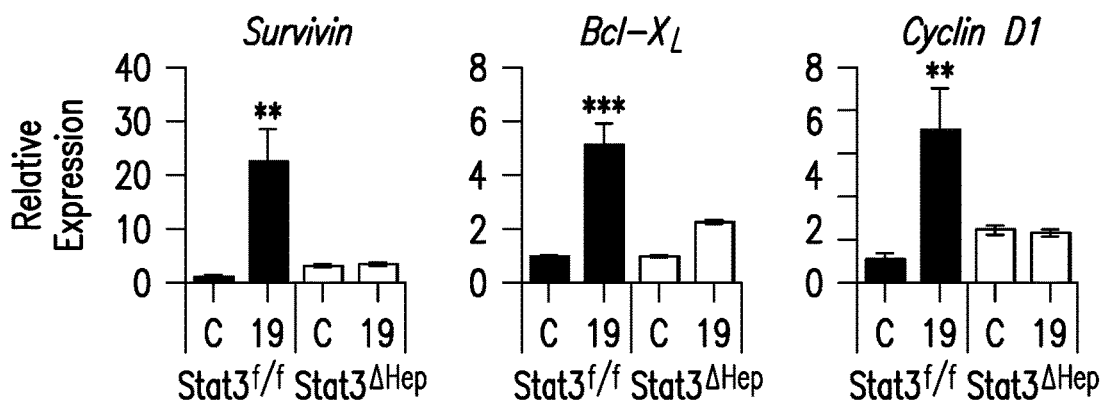
FIGS. 9A-9C depict the effect of FGF19 on relative expression of anti-apoptotic and cell proliferation genes in Stat3$^{f/f}$ and Stat3$^{\Delta Hep}$ mice.
Figure 9B:
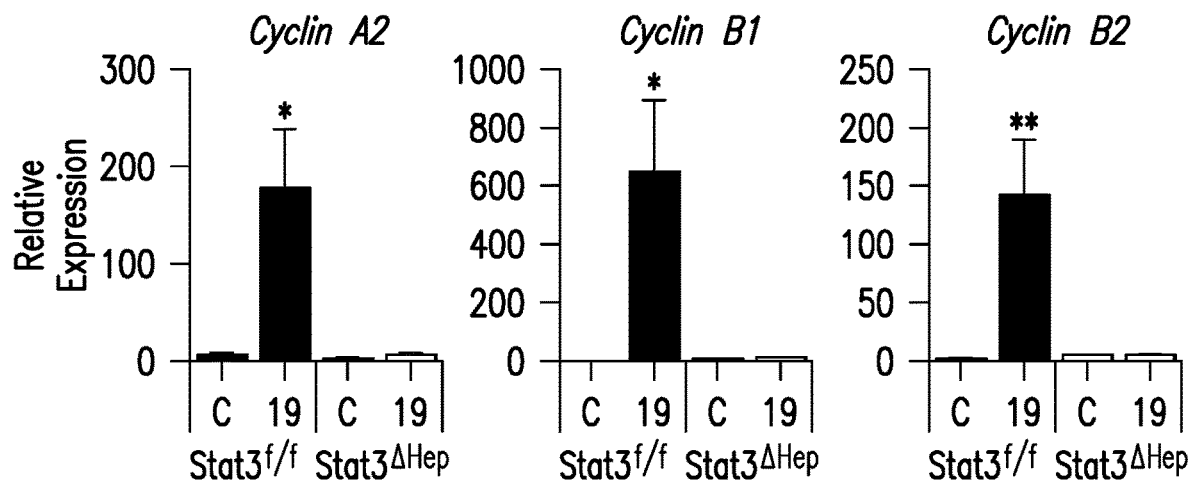
Figure 9C:
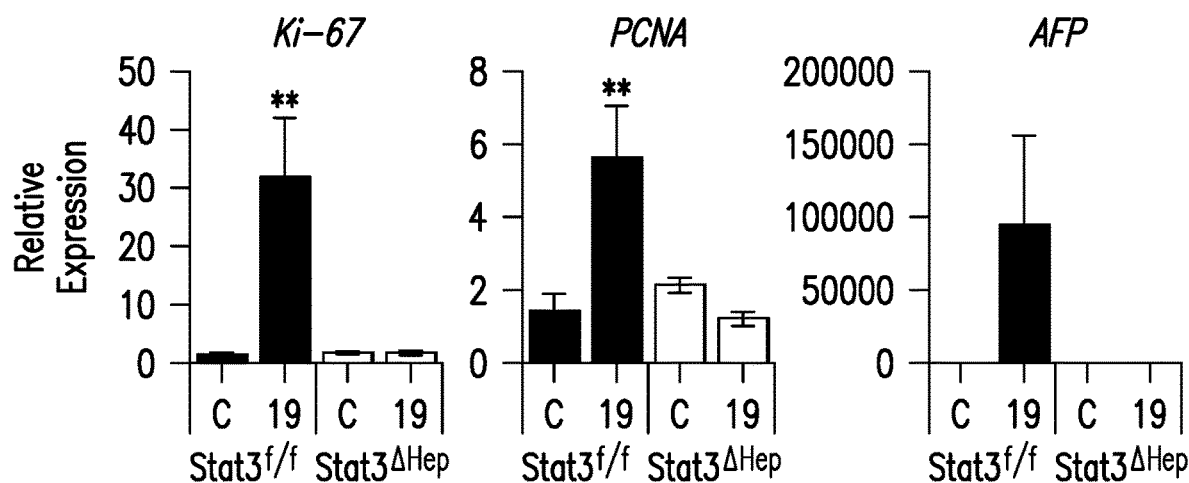

Marked elevation of apoptosis suppressing genes, such as Survivin, Bcl-xL, and Cyclin D1 was observed in livers derived from FGF19-expressing Stat3$^{f/f}$ mice (FIG. 9A). In contrast, mRNA levels of these anti-apoptotic genes were significantly downregulated in livers derived from FGF19-expressing Stat3$^{\Delta Hep}$ mice. In addition, markers of cell cycle progression (Cyclin a2, Cyclin b1, Cyclin b2), cell proliferation (Ki-67, PCNA), and HCC (α-fetoprotein or AFP) (European Association For The Study Of The Liver, 2012), were profoundly induced in livers from FGF19-expressing Stat3$^{f/f}$ mice, but not FGF19-expressing Stat3$^{\Delta Hep}$ mice (FIGS. 9B and 9C).

These data confirm that hepatocellular inactivation of STAT3 blocks the initiation and progression of FGF19-dependent HCC formation.

Example 4

The Effect of the Hepatocellular STAT3 on the Regulation of Bile Acid and Energy Metabolism by FGF19

Figure 4A:
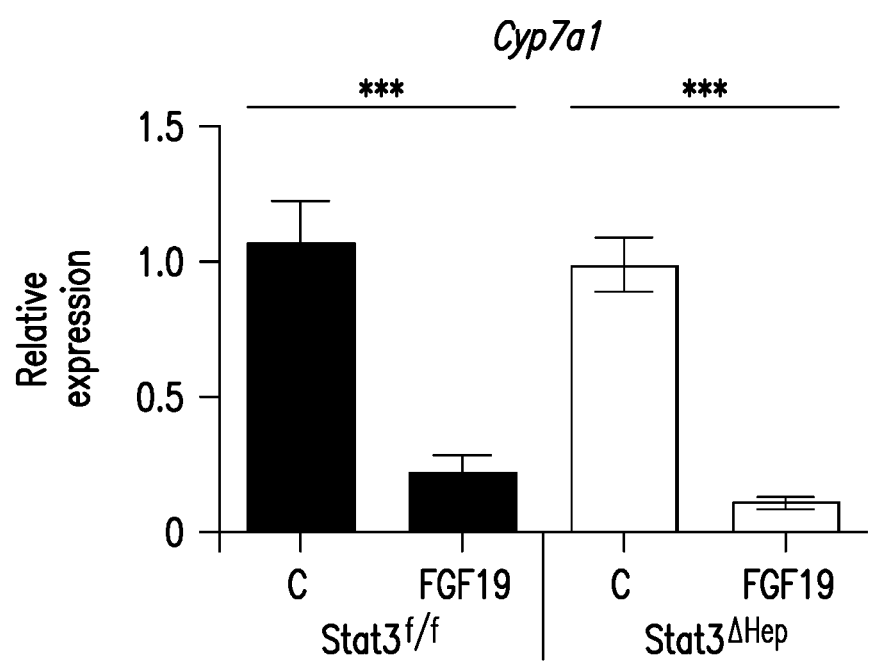
FIGS. 4A-4E depict that loss of STAT3 in hepatocytes does not impair FGF19-dependent metabolic improvements. 14 to 18 week-old Stat3$^{f/f}$ mice received a single tail vein injection of AAV-FGF19 or a combination of AAV-FGF19 and AAV-TBG-Cre. Mice were sacrificed 12 months after AAV administration to determine expression of Cyp7a1 and Cyp8b1 in the liver. Body weight, blood glucose, and body composition were measured one month prior to euthanasia. Data are normalized to housekeeping gene Gapdh and are relative to the expression in control mice.
Figure 4B:
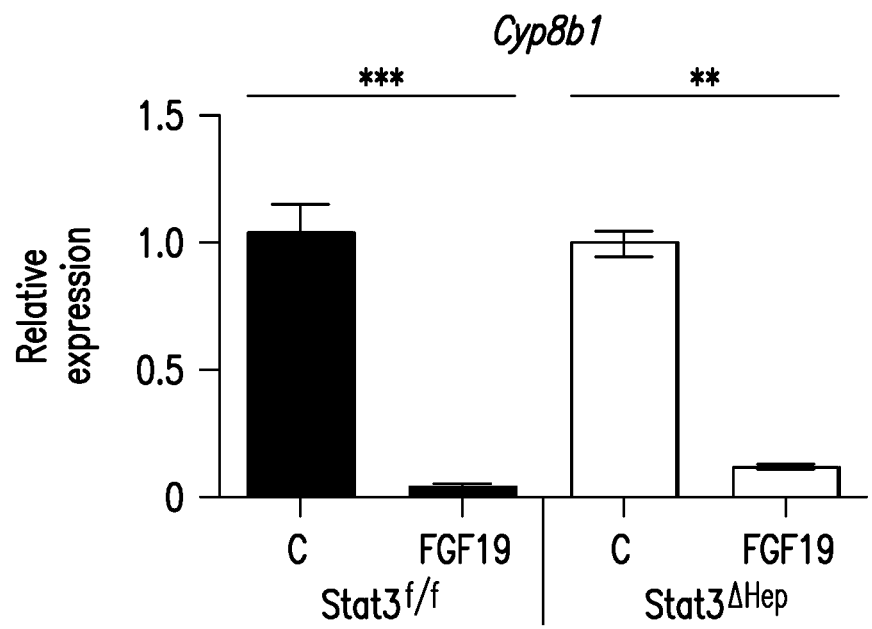

The effects of FGF19 expression on bile acid synthetic enzymes, body weight, glucose, and body composition in the presence or absence of hepatocellular STAT3 were analyzed. FGF19 expression resulted in reduction in mRNA levels of Cyp7a1 in Stat3$^{f/f}$ and Stat3$^{\Delta Hep}$ mice (77% and 87% reduction, respectively; FIG. 4A). Similar effects were observed in Stat3$^{f/f}$ and Stat3$^{\Delta Hep}$ mice (95% and 88% reduction, respectively) for mRNA levels of Cyp8b (FIG. 4B).

Figure 4C:
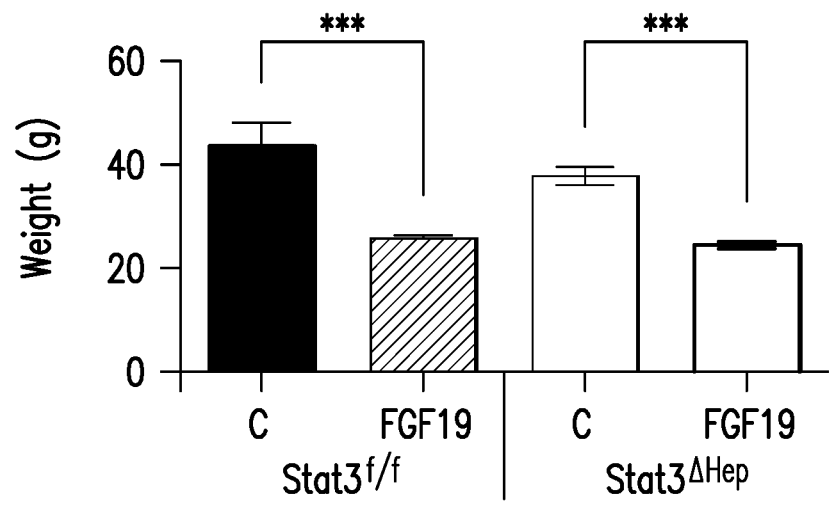
Figure 4D:
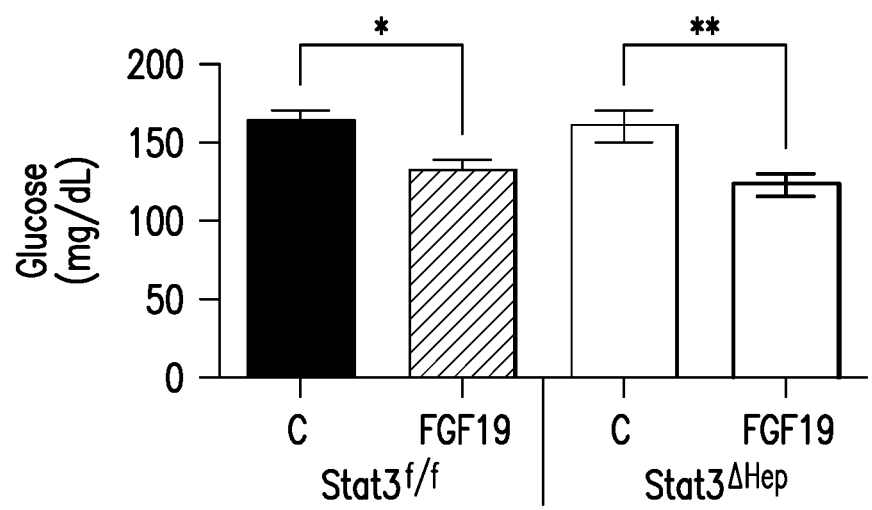
Figure 4E:
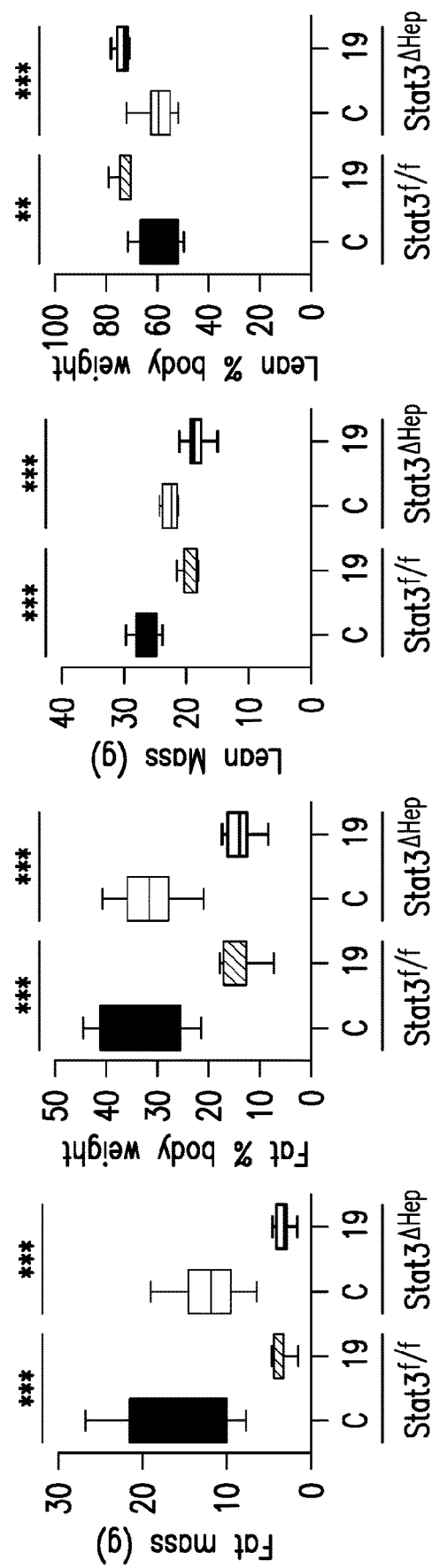

FGF19 demonstrated weight-lowering and glucose-lowering effects in Stat3$^{f/f}$ mice (FIGS. 4C and 4D). Similar results were obtained in Stat3$^{\Delta Hep}$ mice. Hepatocyte-specific STAT3 deficiency had no effect on FGF19-mediated changes in body composition, as fat and lean mass were indistinguishable between Stat3$^{f/f}$ and Stat3$^{\Delta Hep}$ mice expressing FGF19 (FIG. 4E). Similarly, liver steatosis was improved by FGF19 treatment to a similar degree in Stat3$^{f/f}$ and Stat3$^{\Delta Hep}$ mice (data not shown).

These results indicate that FGF19 functions in a STAT3-independent manner in regulating bile acid biosynthesis and metabolic improvements.

Example 5

The Effect of Interleukin-6 on Cell-Autonomous Activation of STAT3 by FGF19

Figure 5A:
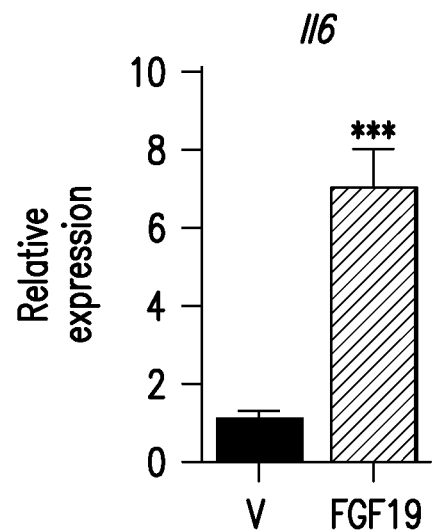
FIGS. 5A-5G depict the process of identification of secreted factor(s) mediating non-cell autonomous activation of STAT3 by FGF19.
Figure 5B:
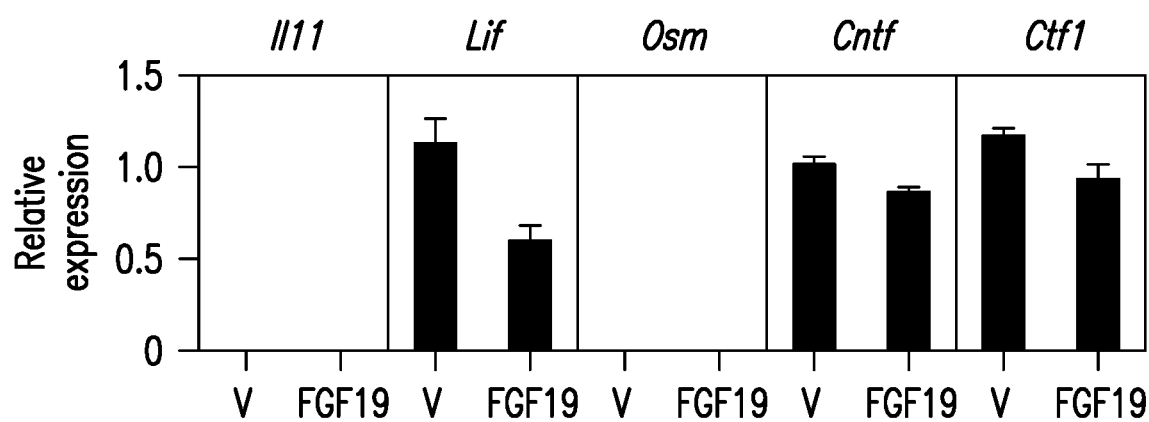
Figure 5C:
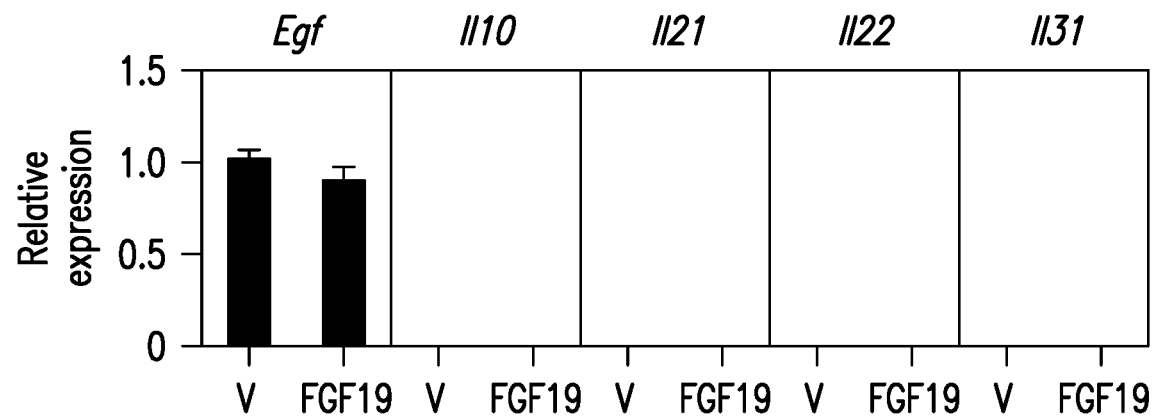
Figure 5D:
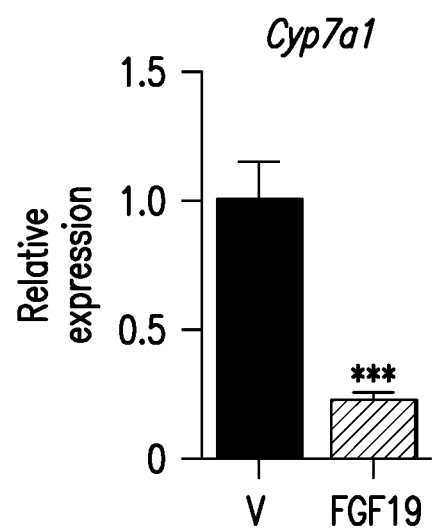

To identify the secreted factor(s) mediating FGF19-induced STAT3 activation in vivo, the hepatic expression of cytokines activating gp130 receptors, such as IL-6, IL-11, leukemia inhibitory factor (LIF), oncostatin M (OSM), ciliary neurotrophic factor (CNTF), and cardiotrophin-1 (CTF1) were measured in FGF19-treated mice. Hepatic mRNA levels of IL-6 increased significantly following administration of FGF19 in db/db mice, correlating with STAT3 activation in these mice (FIG. 5A). The RNA levels of IL-11, LIF, OSM, CNTF and CTF1 remained unchanged or undetectable (FIG. 5B). In addition, levels of growth factors and cytokines known to be associated with increased pSTAT3 signals, including epidermal growth factor (EGF) (Zhong et al., 1994, *Science*, 264:95-98), IL-10 (Weber-Nordt et al., 1996, *JBC*, 271:27954-27961), IL-21 (Brenne et al., 2002, *Blood*, 99:3756-3762), IL-22 (Radaeva et al., 2004, *Hepatology*, 39:1332-1342), and IL-31 (Chattopadhyay et al., 2007, *JBC*, 282:3014-3026), were either not elevated or undetectable in FGF19-treated livers (FIG. 5C). Hepatic Cyp7a1 mRNAs were efficiently suppressed by acute FGF19 treatment in these mice (FIG. 5D).

Figure 5E:
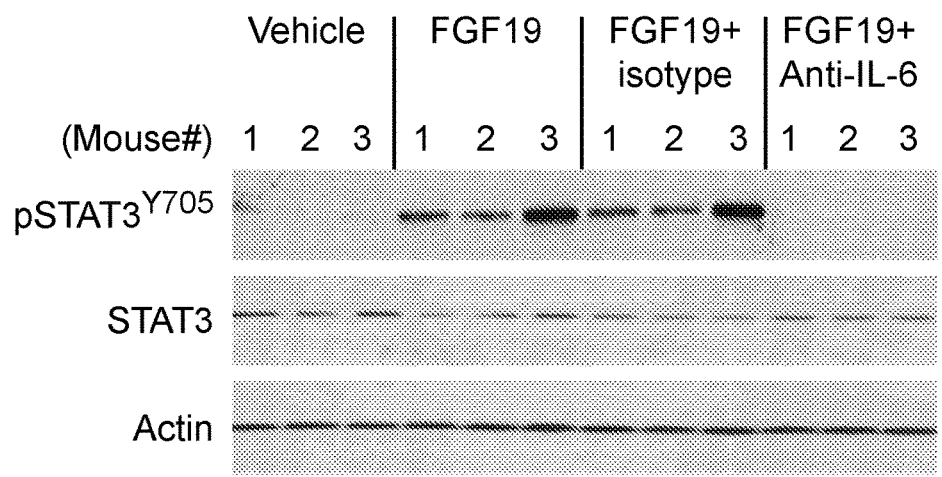

Intraperitoneal injection of db/db mice with a neutralizing antibody against mouse IL-6 prior to FGF19 administration resulted in marked reduction of FGF19-triggered STAT3 phosphorylation as demonstrated by immunoblot analysis of total liver lysates (FIG. 5E). No effects were observed when mice were pretreated with an isotype control antibody.

Figure 5F:
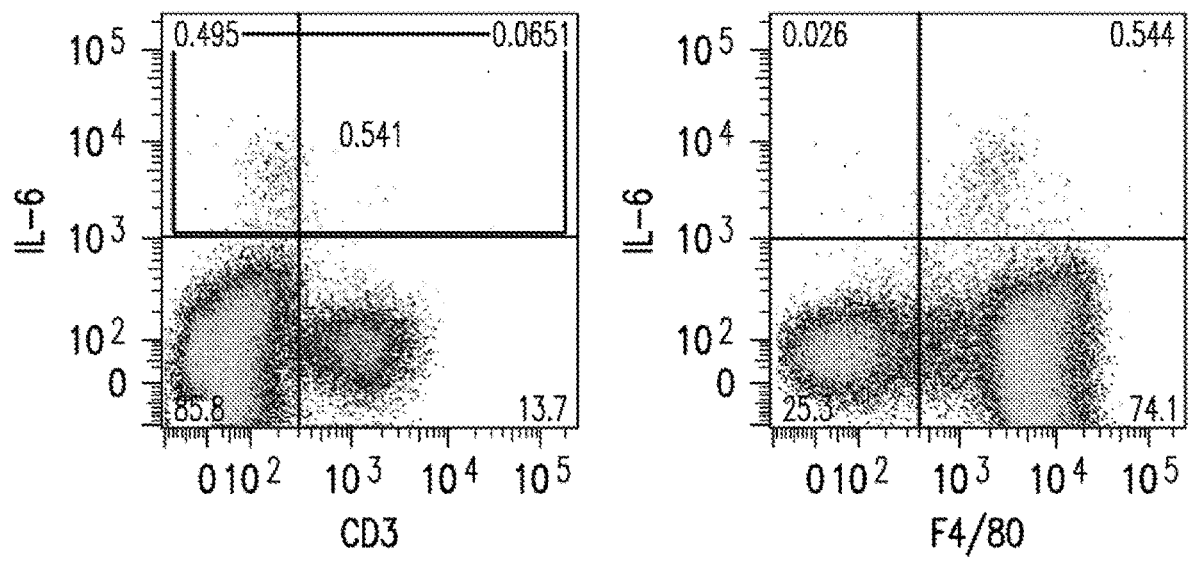
Figure 5G:
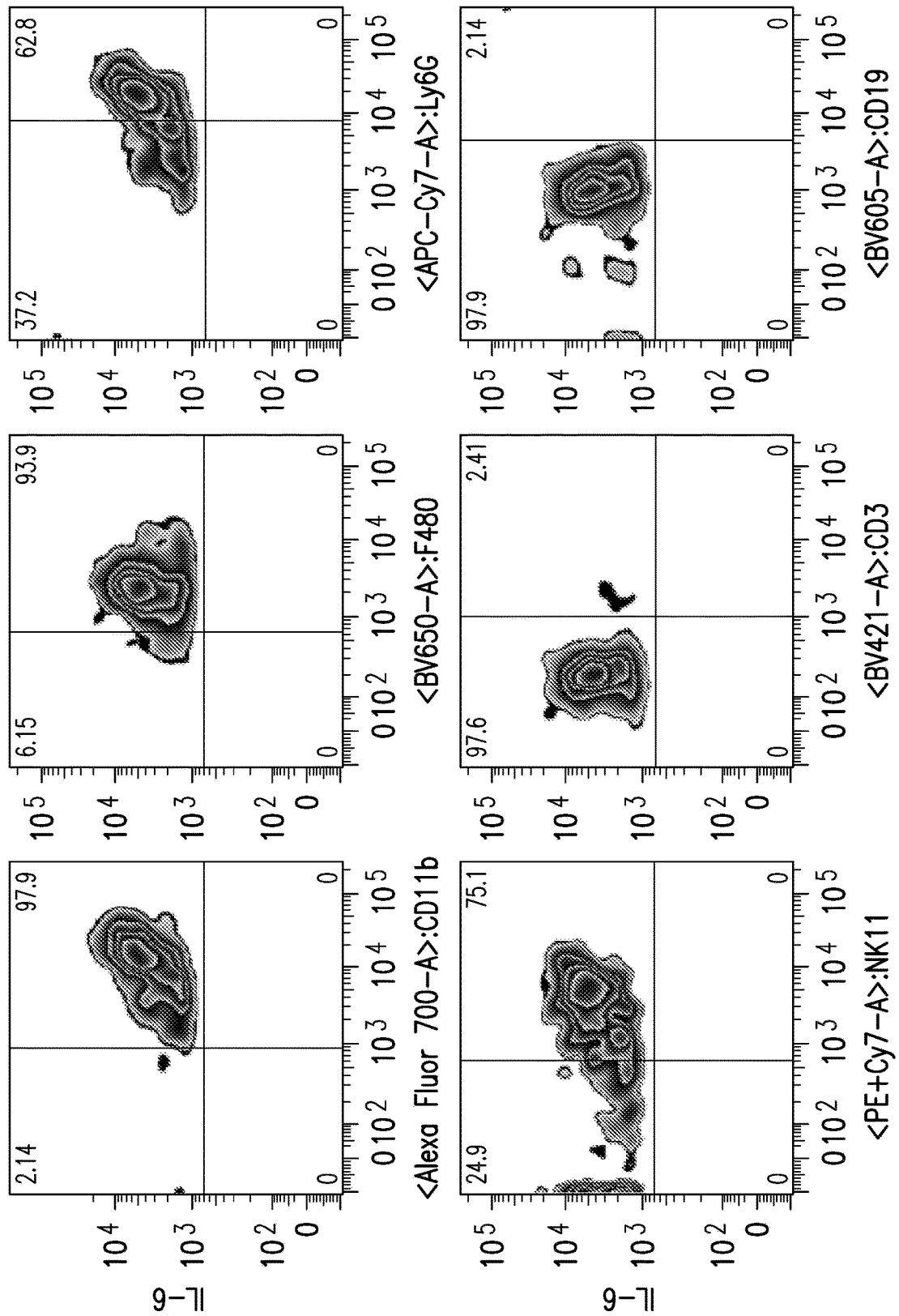

Intracellular cytokine staining and flow cytometry revealed strong IL-6 expression in liver infiltrating immune cells but undetectable in CD45-negative cells after FGF19 stimulation (FIG. 5F). Specifically, myeloid cells including Kupffer cells (CD45+CD11b+F4/80+), neutrophils (CD45+CD11b+Ly6G+), and NK cells (CD45+NK1.1+) were the major IL-6 producers, while little or no IL-6 was detected in T (CD45+CD3+) or B cells (CD45+CD19+) (FIG. 5G).

These data suggest that innate immune cell-derived IL-6 is a major component of FGF19-dependent STAT3 activation in hepatocytes.

Example 6

The Effect of Homozygous Deletion of IL-6 on FGF19-Mediated HCC Development

Figure 6A:
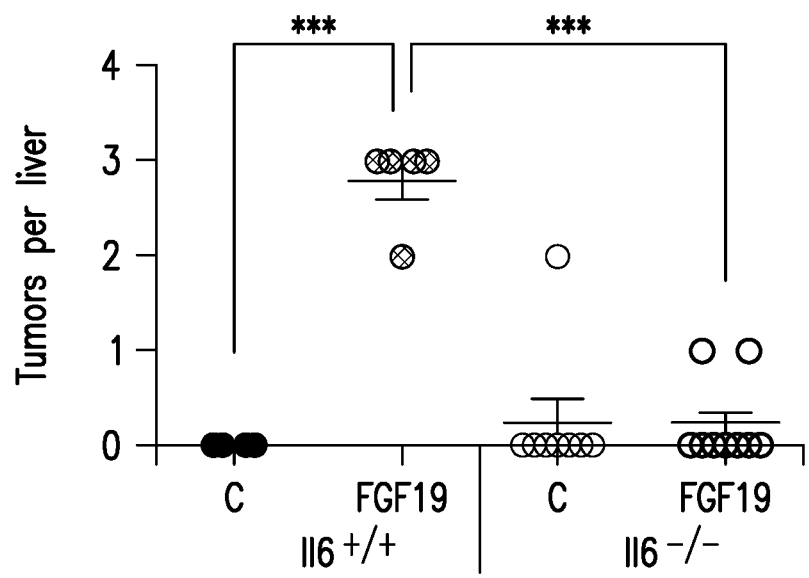
FIGS. 6A-6H depict the effect of homozygous deletion of IL-6 on FGF19-induced HCC development. Il6$^{+/+}$ or Il6$^{-/-}$ mice received a single tail vein injection of AAV-FGF19 or a control virus. Mice were sacrificed after prolonged exposure to FGF19 for 12 months.
Figure 6B:
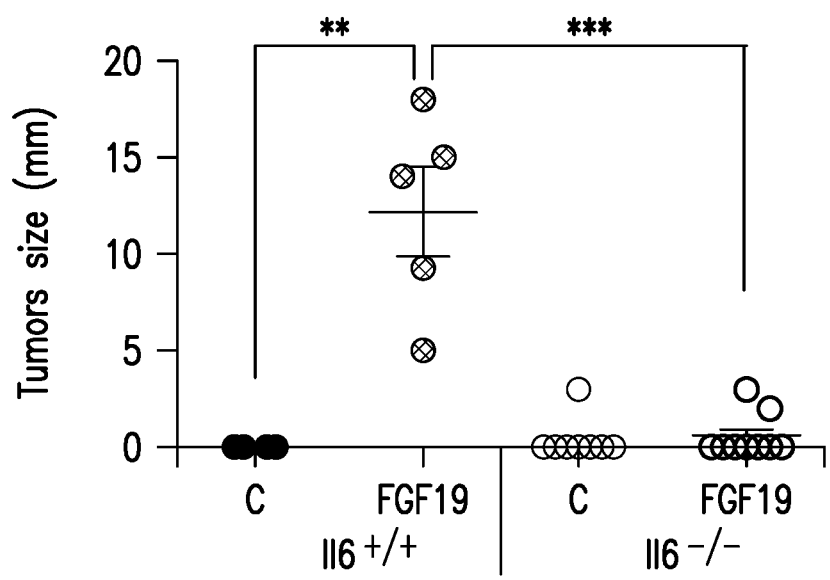
Figure 6C:
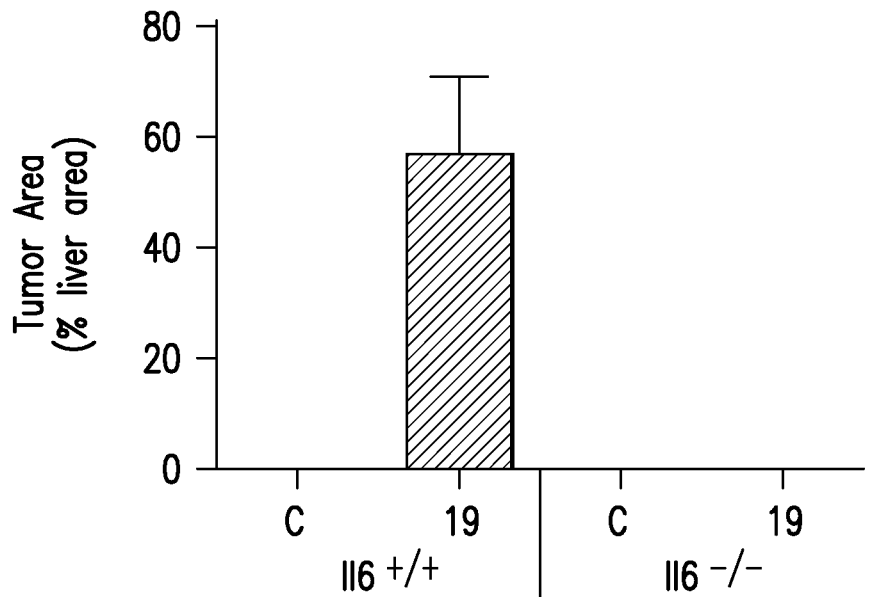
Figure 6D:
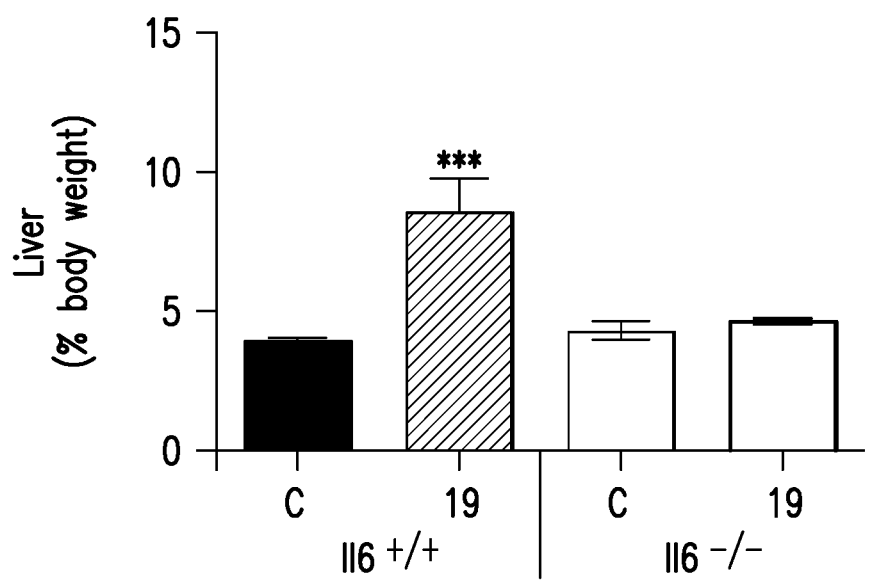

To determine the functional significance of IL-6 in FGF19-induced HCC progression, AAV-FGF19 were injected intravenously into wild type (Il6$^{+/+}$) or Il-6-deficient (Il6$^{-/-}$) mice. HCC development was evaluated 12 months post-AAV administration (FIGS. 6A-6D). Prolonged exposure to FGF19 induced HCC formation, as evidenced by large, glutamine synthetase-positive liver tumors in Il6$^{+/+}$ mice. In contrast, genetic ablation of Il-6 resulted in a significant decrease in FGF19-induced tumor multiplicity (FIG. 6A), tumor size (FIG. 6B), and glutamine synthetase-positive tumor area (FIG. 6C). In addition, FGF19 expression increased liver-to-body weight ratios in Il6$^{+/+}$ mice, but not in Il6$^{-/-}$ mice (FIG. 6D). These observations are similar to that seen in mice with hepatocellular deficiency of STAT3 (FIGS. 3A-3F).

Figure 6E:
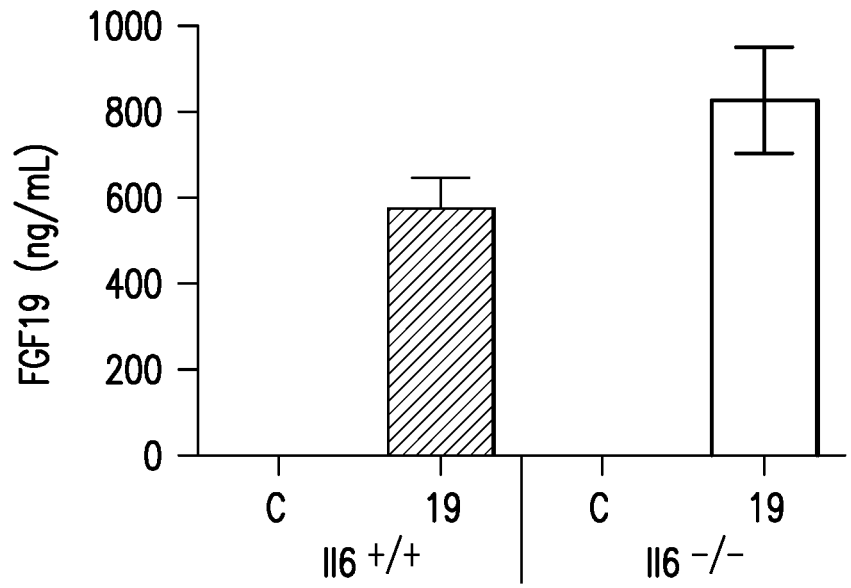
Figure 6F:
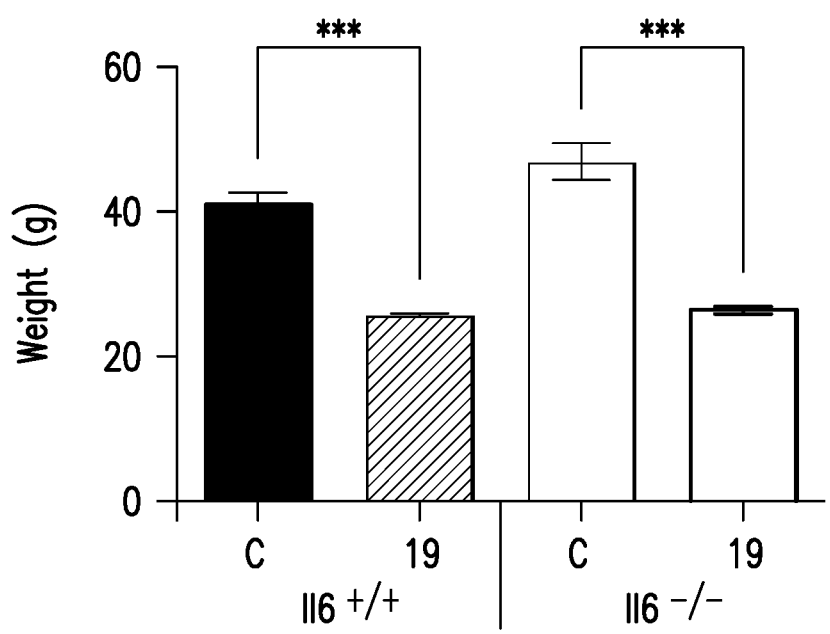
Figure 6G:
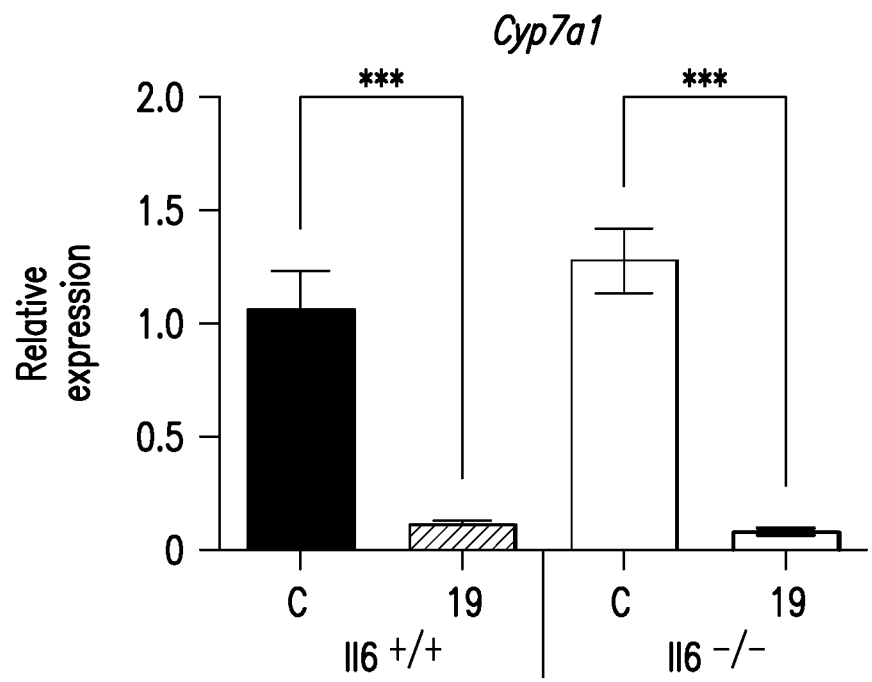
Figure 6H:
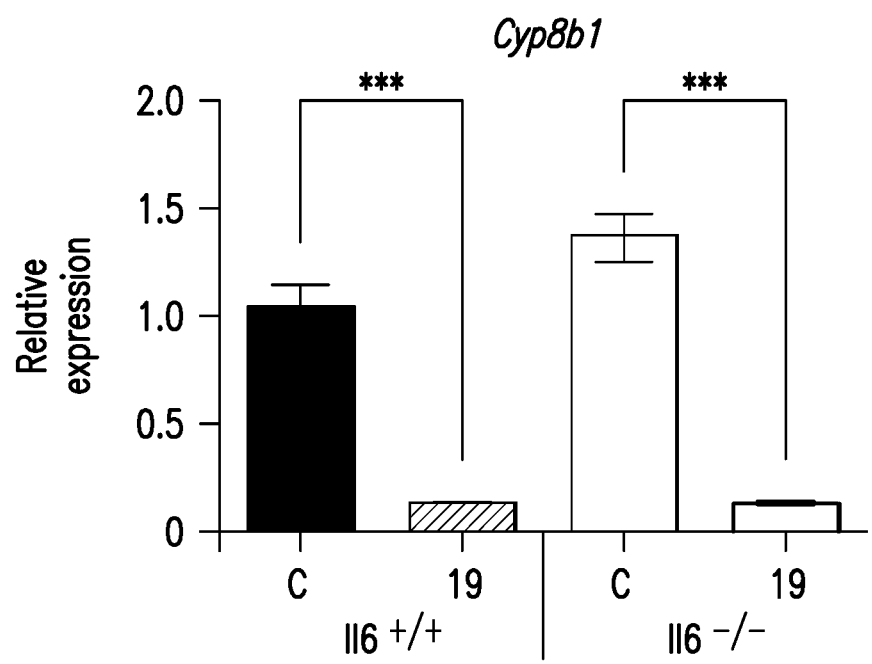
Figure 10A:
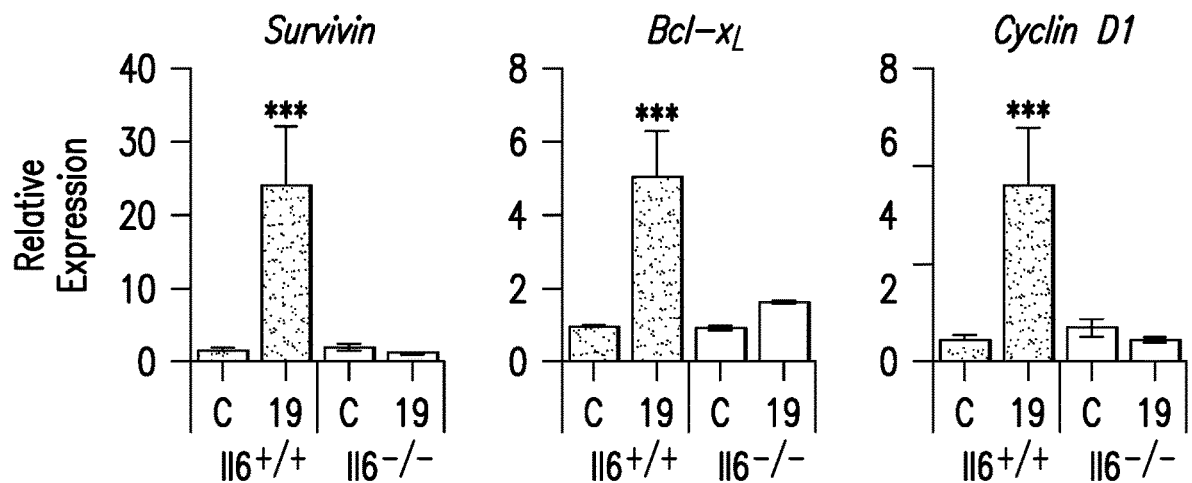
FIGS. 10A-10C depict the effect of FGF19 on relative expression of anti-apoptotic and cell proliferation genes in Il6$^{+/+}$ and Il6$^{-/-}$ mice.
Figure 10B:
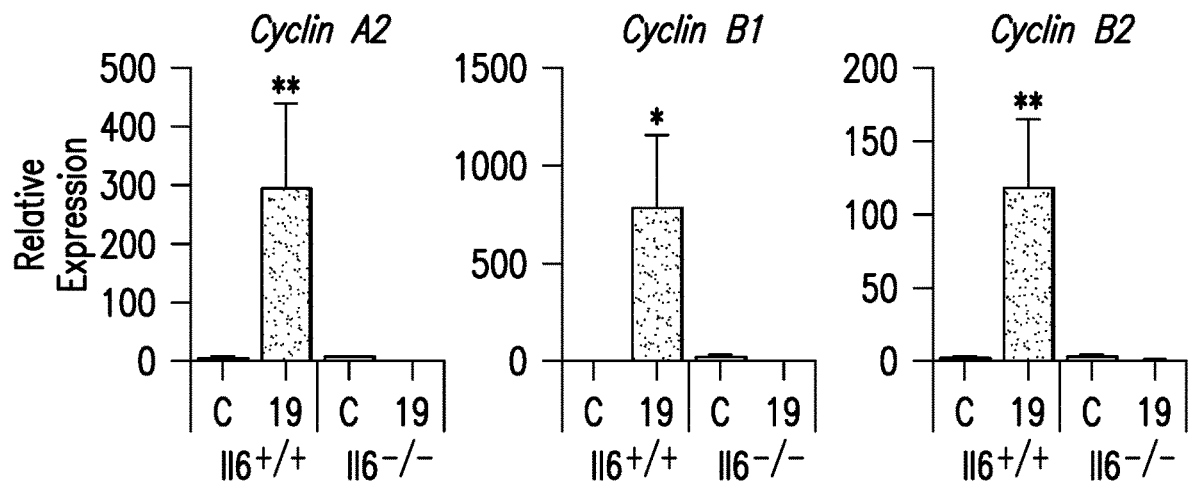
Figure 10C:
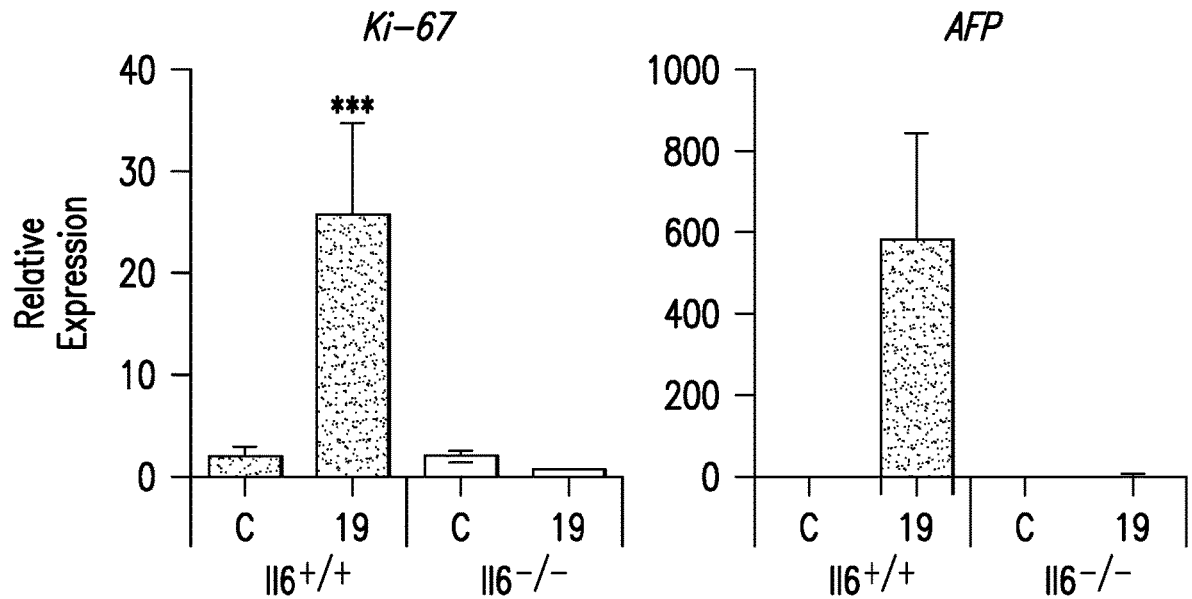
Figure 11A:
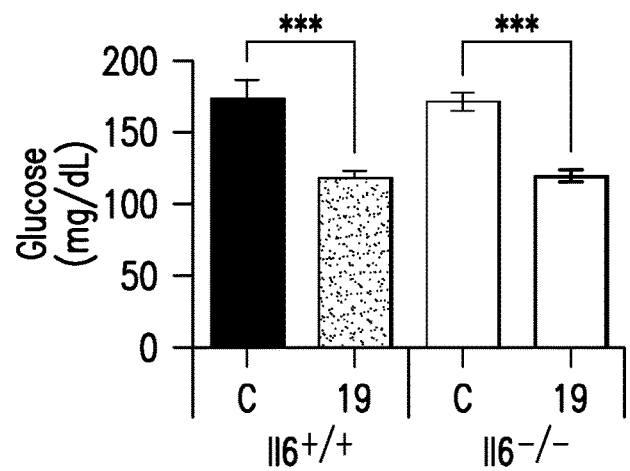
FIGS. 11A-11C depict the effect of genetic ablation of Il6 on FGF19-mediated metabolic action.
Figure 11B:
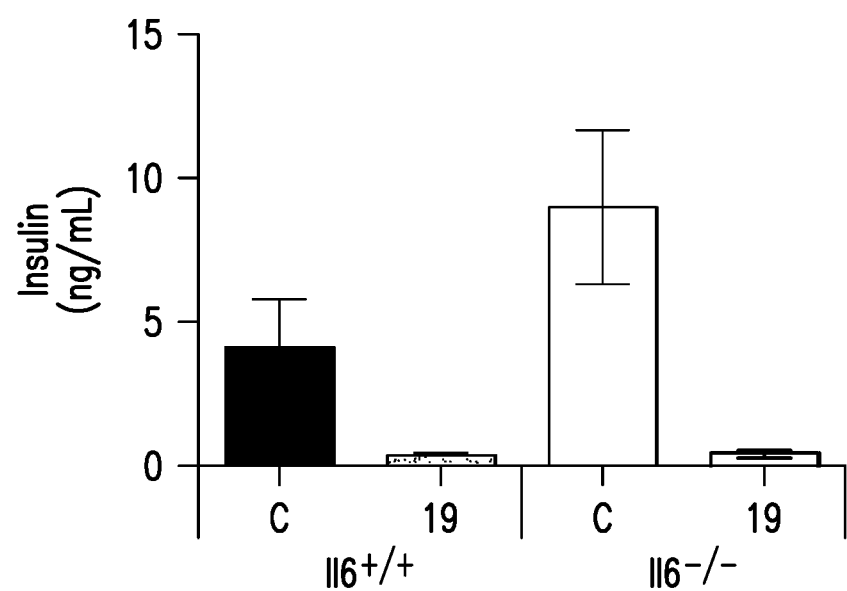
Figure 11C:
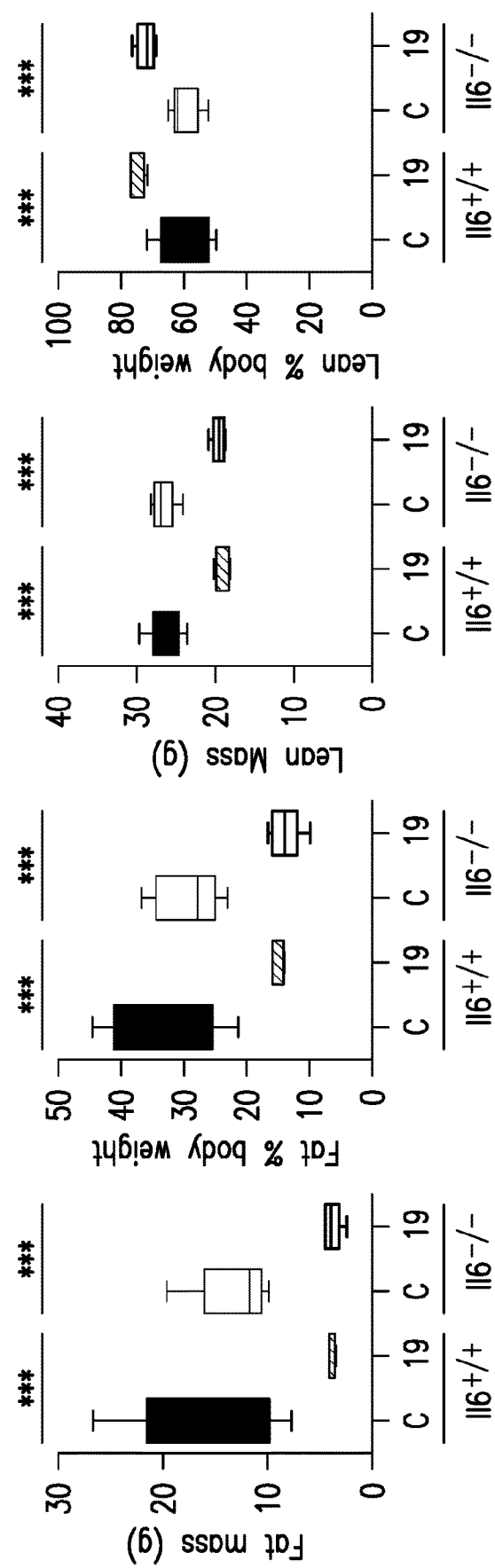

Circulating levels of FGF19 in Il6$^{-/-}$ mice were detected at levels equivalent to or greater than in Il6$^{+/+}$ mice, thereby excluding the possibility of reduced FGF19 expression as a cause of the diminished tumorigenicity (FIG. 6E). Il-6 deficiency also reduced hepatic mRNA levels of STAT3 target genes (Survivin, Bcl-xL, and Cyclin D1; FIG. 10A), cyclins (Cyclin a2, Cyclin b1, Cyclin b2; FIG. 10B), and markers of proliferation (Ki-67; FIG. 10C) and HCC (AFP; FIG. 10C) in livers from FGF19-expressing mice. To determine whether genetic ablation of Il-6 has an effect on FGF19-mediated metabolic action, body weight, plasma glucose, and insulin levels in these mice were monitored (FIGS. 11A-11C). No significant differences in these parameters were detected in FGF19-treated Il6$^{-/-}$ and Il6$^{-/-}$ mice (FIGS. 6F, 11A and 11B). Lack of IL-6 expression altered neither FGF19-triggered Cyp7a1 expression nor Cyp8b1 inhibition (FIGS. 6G and 6H). In addition, FGF19 efficiently reduced body fat composition in both Il6$^{+/+}$ and Il6$^{-/-}$ mice (FIG. 11C).

These data indicate that IL-6 is dispensable for FGF19-controlled metabolic improvement and bile acid metabolism in mice.

Example 7

The Effect of Pharmacological Inhibition of STAT3/IL-6 Axis on FGF19-Mediated HCC The in vivo efficacy of inhibitors of the STAT3/IL-6 pathway was tested in engineered mouse models of FGF19-mediated HCC. The diabetic db/db model allows the study of anti-diabetic effects as well as tumorigenic effects of FGF19. Mdr2$^{-/-}$ model, a model of chronic liver disease, enables simultaneous interrogation of hepatoprotective as well as HCC-promoting actions of FGF19. These models are clinically relevant, as multiple reports were published correlating higher HCC incidence and progression with co-commitant diabetes or chronic liver diseases (Davila et al., 2005, *Gut*, 54:533-539; El-Serag, 2004, *Gastroenterology*, 127:S27-34; El-Serag et al., 2004, *Gastroenterology*, 126: 460-468).

Figure 7A:
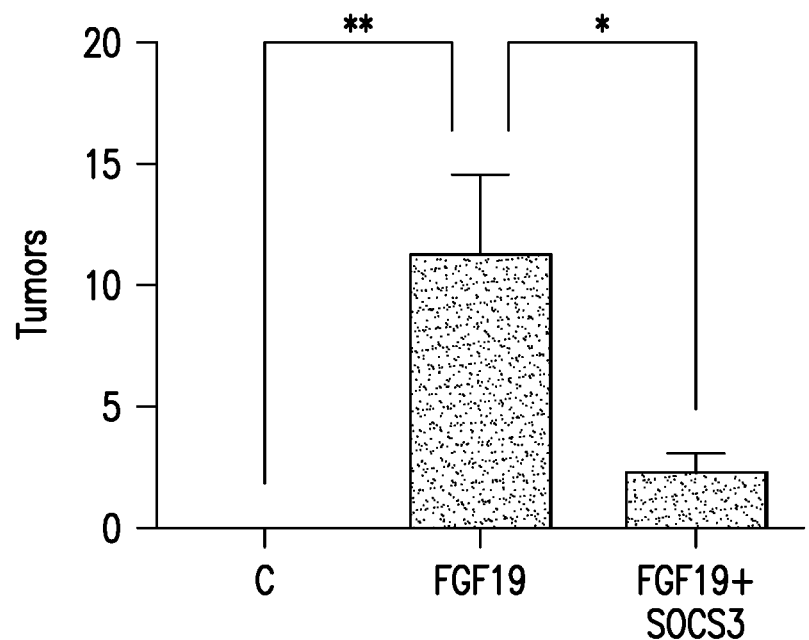
FIGS. 7A-7G depict the effect of pharmacological inhibition of the STAT3/IL-6 axis on FGF19-dependent HCC.
Figure 7B:
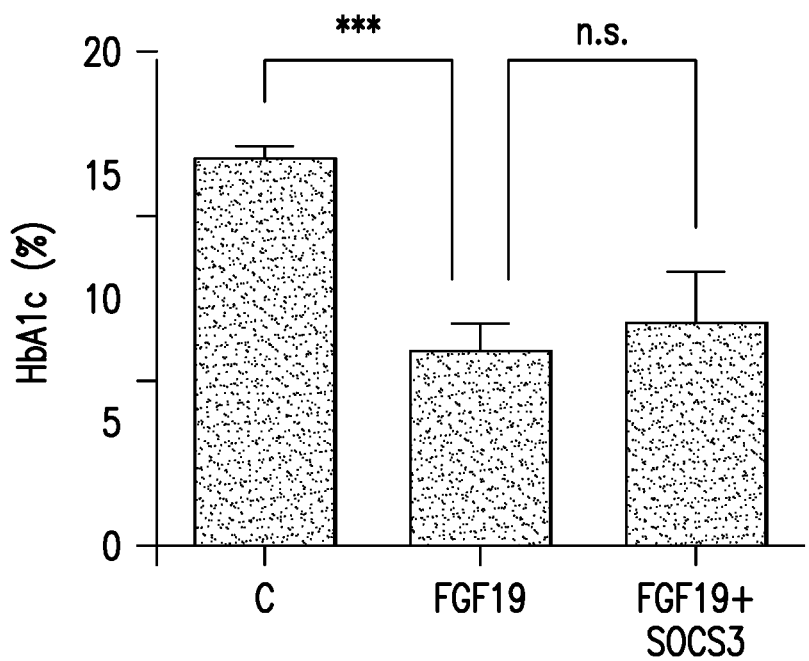
Figure 12A:
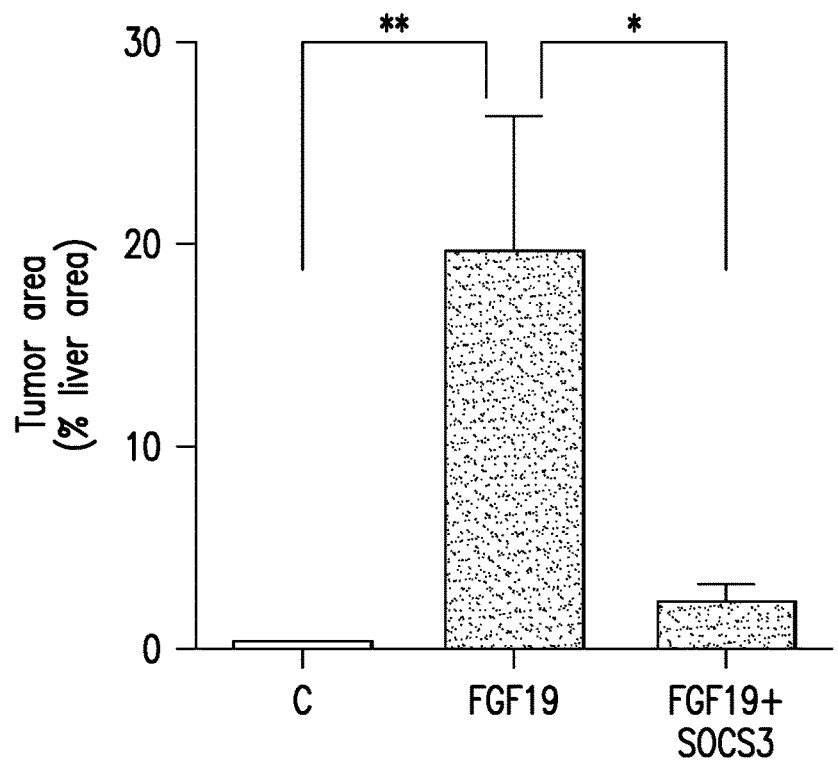
FIGS. 12A-12L depict the effect of pharmacological inhibition of STAT3/IL-6 axis on FGF19-mediated HCC and FGF19 metabolic functions.
Figure 12B:
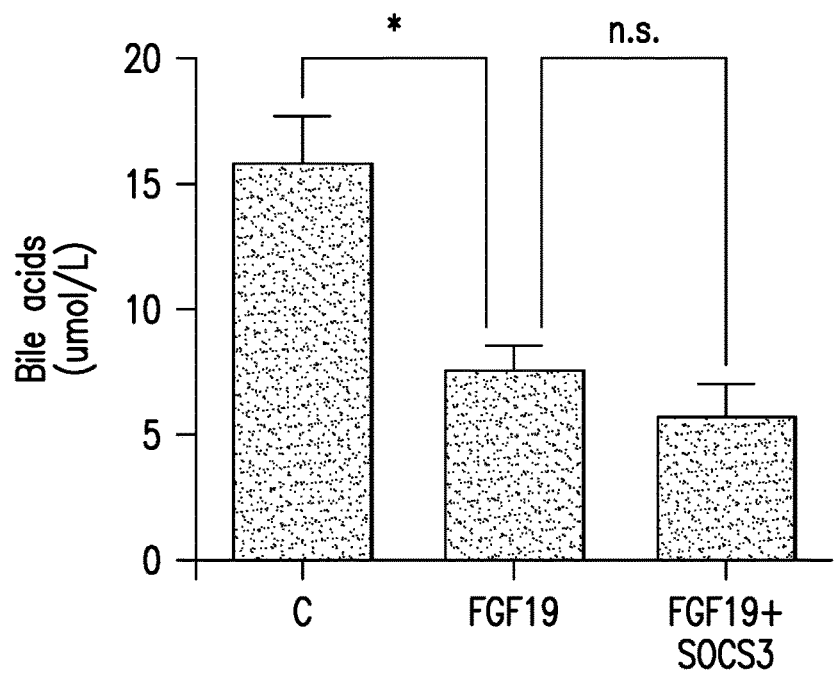
Figure 12C:
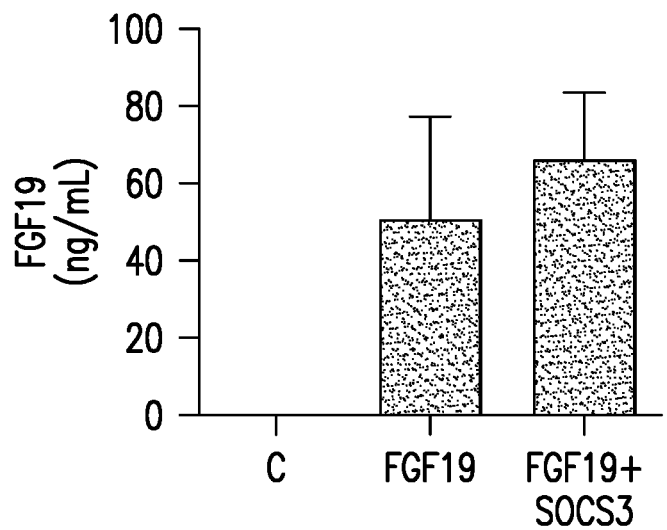

In a 24-week efficacy study, db/db mice were co-administered with AAV-FGF19 and AAV-SOCS3 (suppressor of cytokine signaling 3 (SOCS3)) at a 1:10 ratio intravenously to evaluate the role of SOCS3 as an endogenous inhibitor of STAT3 to prevent FGF19-mediated HCC. 24 weeks after AAV injection, db/db mice developed HCC macroscopically and histologically. Co-expression of SOCS3 significantly reduced FGF19-associated liver tumor formation (FIGS. 7A and 12A). SOCS3 had no impact on FGF19-mediated hemoglobin A1c (HbA1c)-lowering (FIG. 7B) and bile acid lowering (FIG. 12B) effects when co-expressed in db/db mice. Similar circulating FGF19 levels were observed in both groups of mice (FIG. 12C).

Figure 7C:
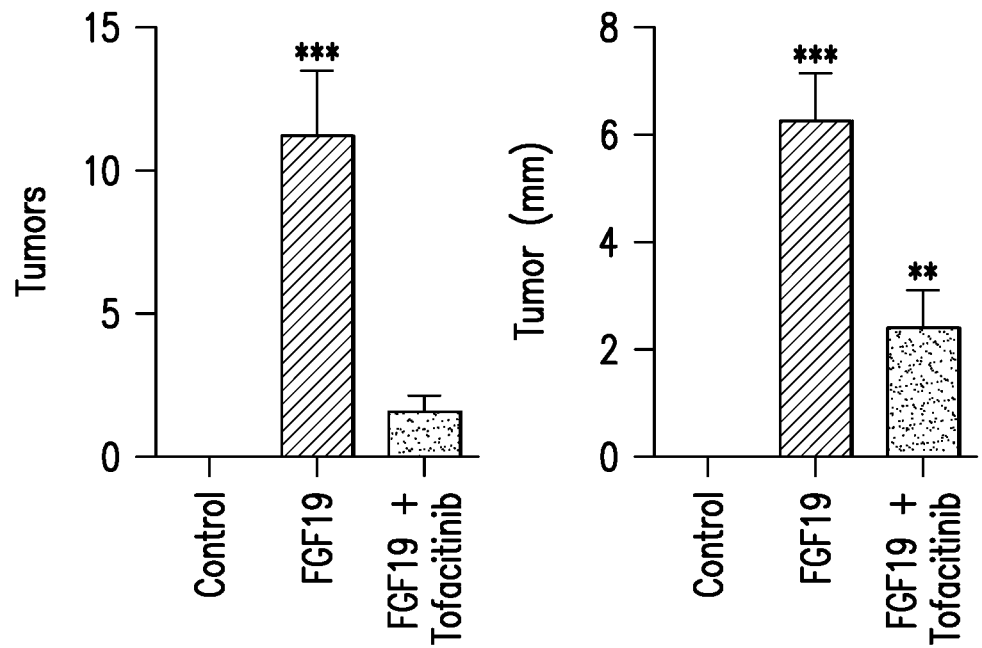
Figure 7D:
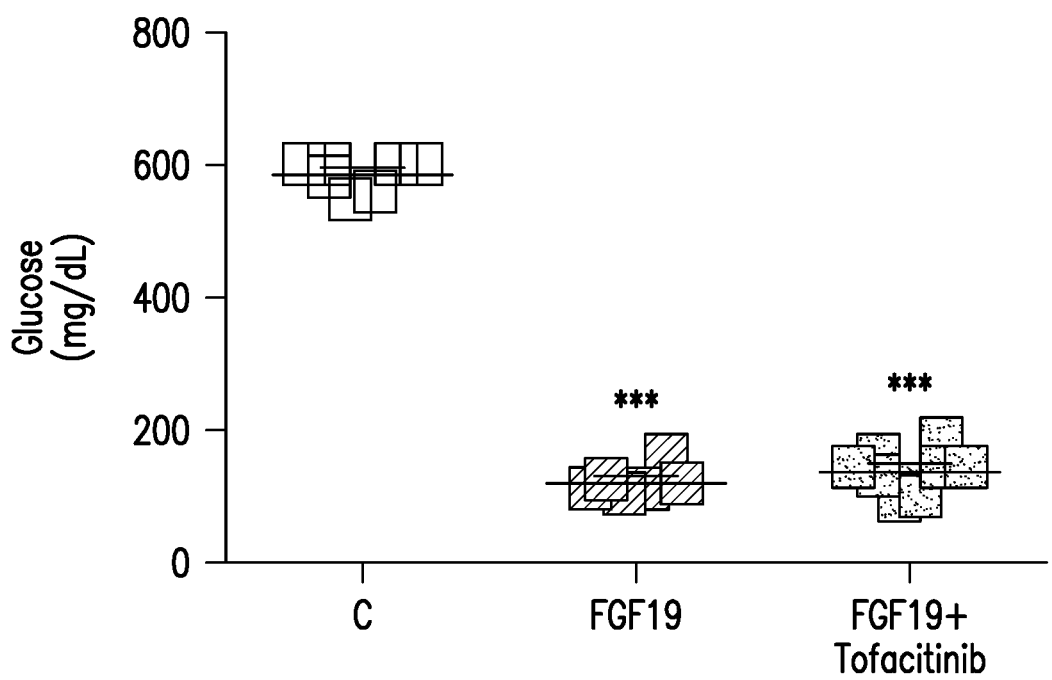
Figure 12D:
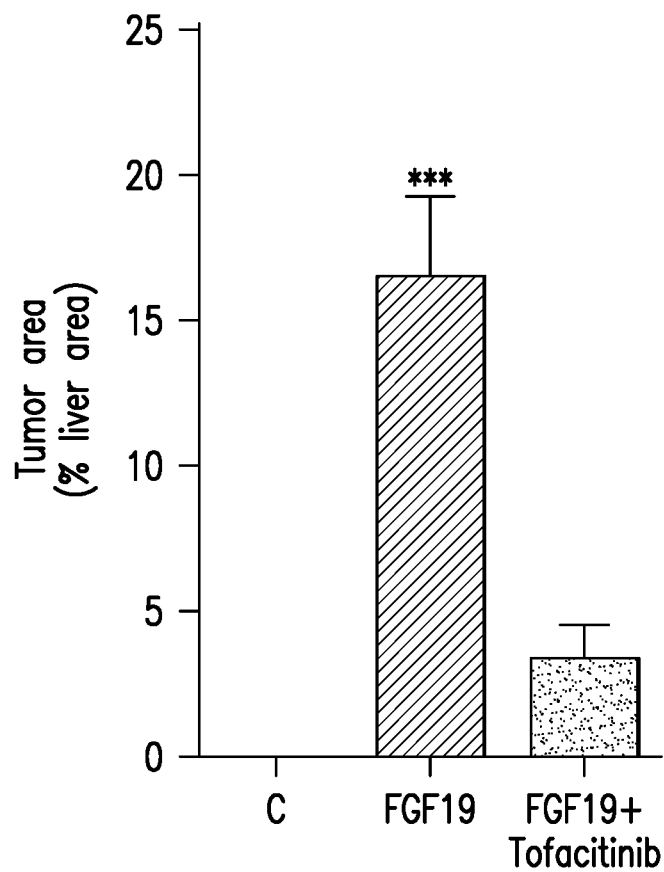
Figure 12E:
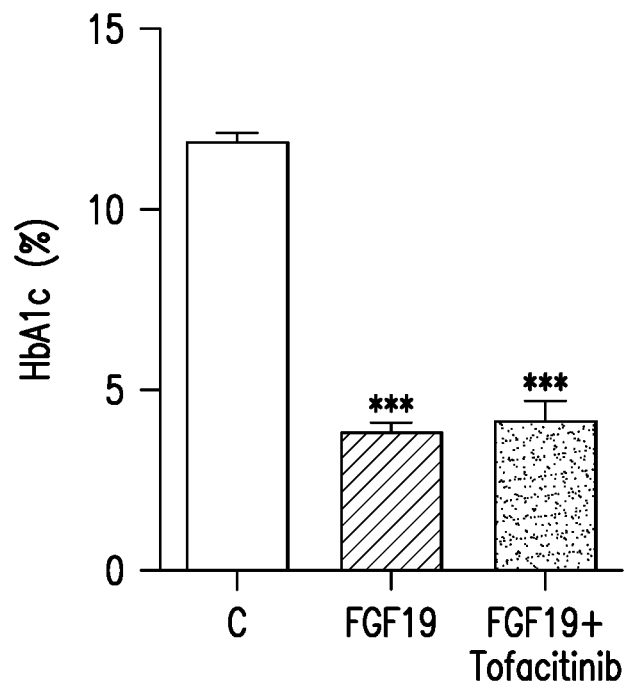
Figure 12F:
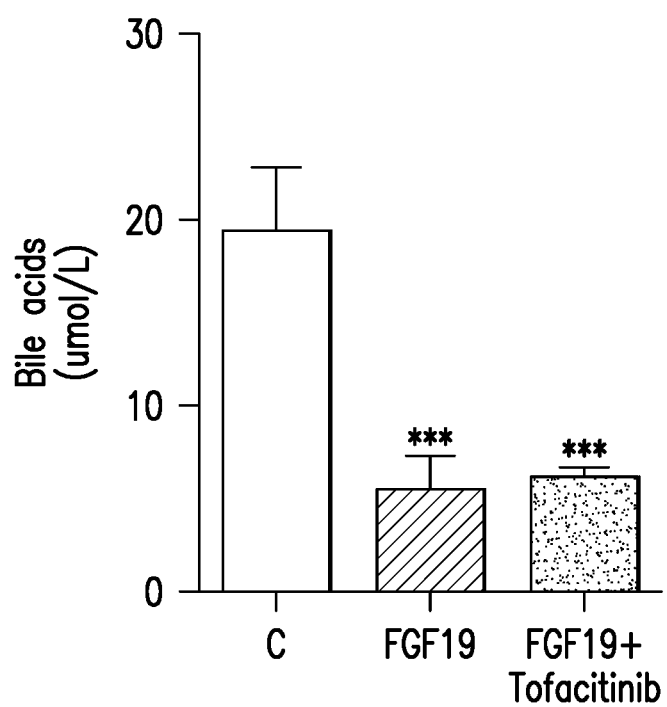
Figure 12G:
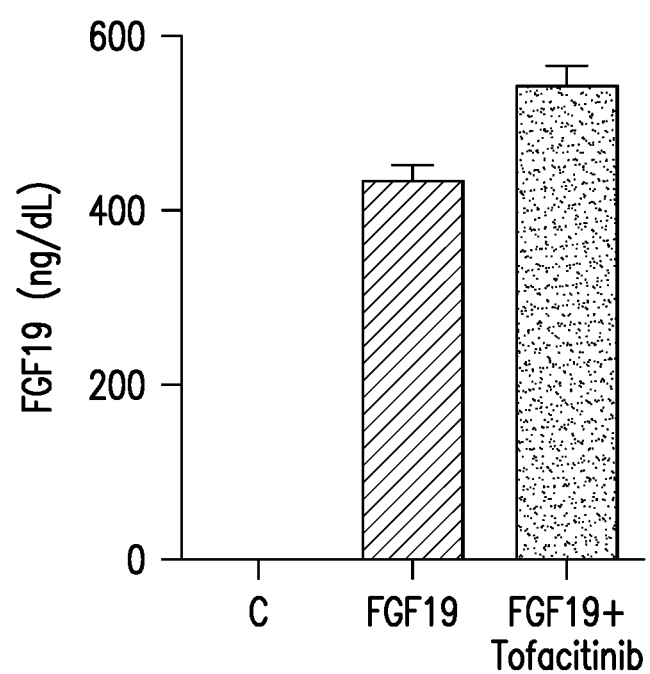

Administration of pan-JAK inhibitor tofacitinib as part of a diet to db/db mice 4 weeks after injection of AAV-FGF19 reduced the number of macroscopically detectable tumors and average tumor load in FGF19-expressing mice (assessed by staining of histological liver sections with H&E or anti-glutamine synthetase) (FIGS. 7C and 12D). Tofacitinib had no impact on FGF19's effects on normalizing blood levels of glucose (FIG. 7D), HbA1c (FIG. 12E), and bile acids (FIG. 12F). Similar circulating FGF19 levels were observed in both groups of mice (FIG. 12G).

Figure 7E:
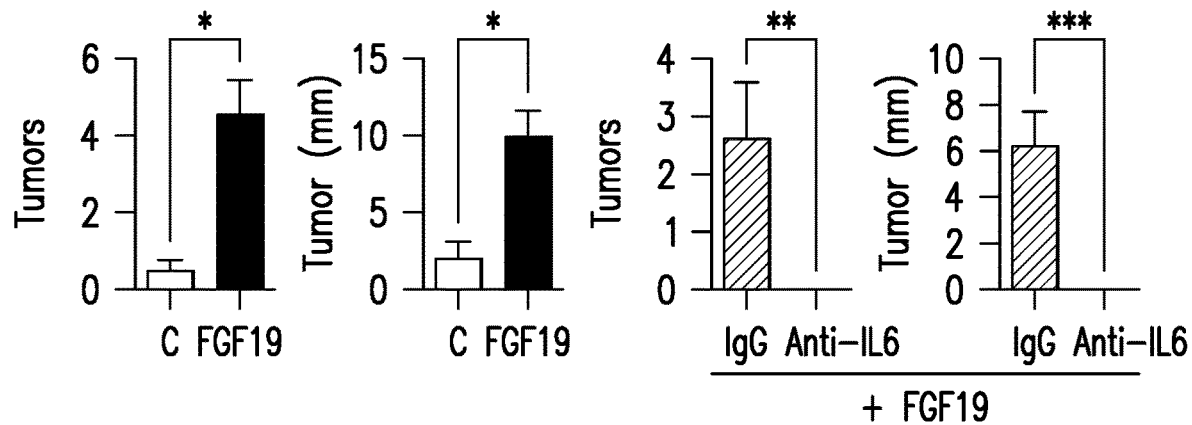
Figure 7F:
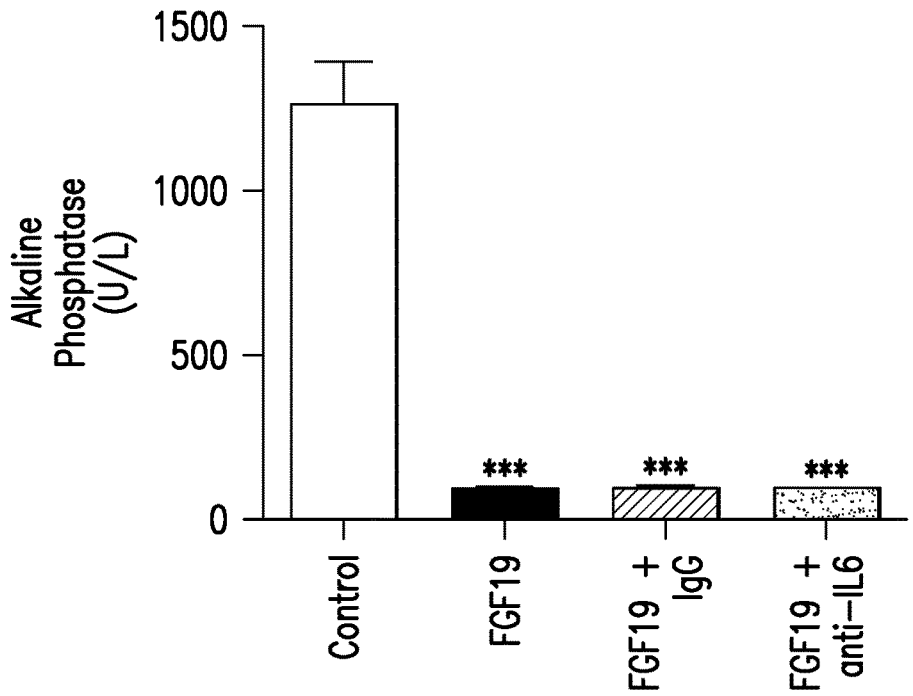
Figure 7G:
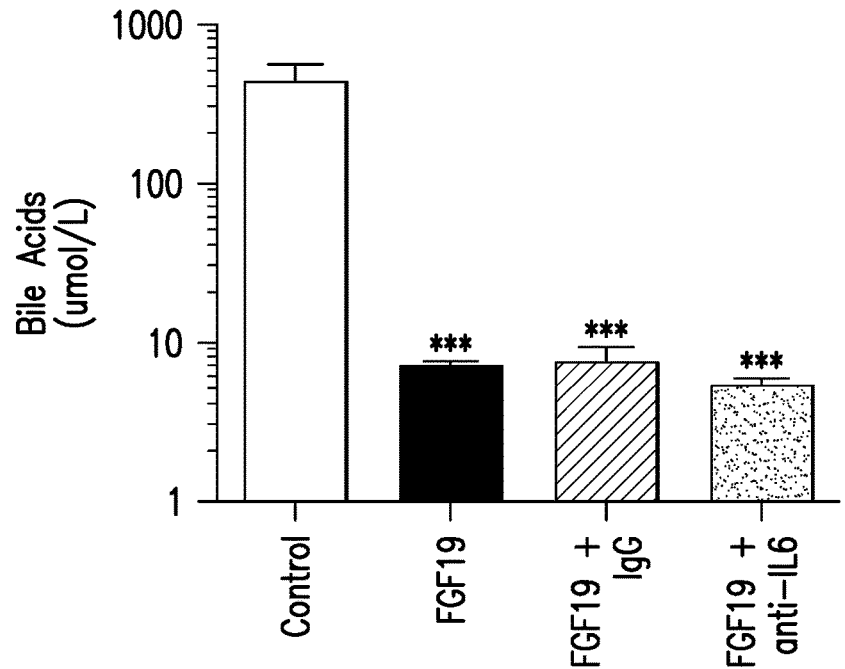
Figure 12H:
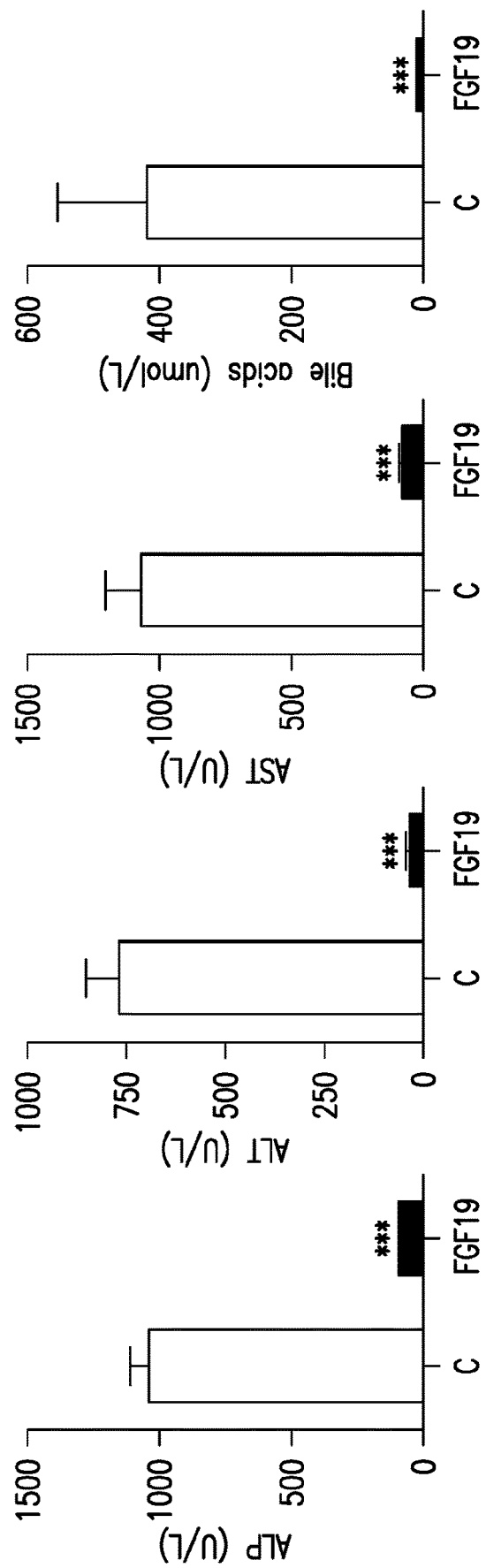
Figure 12I:
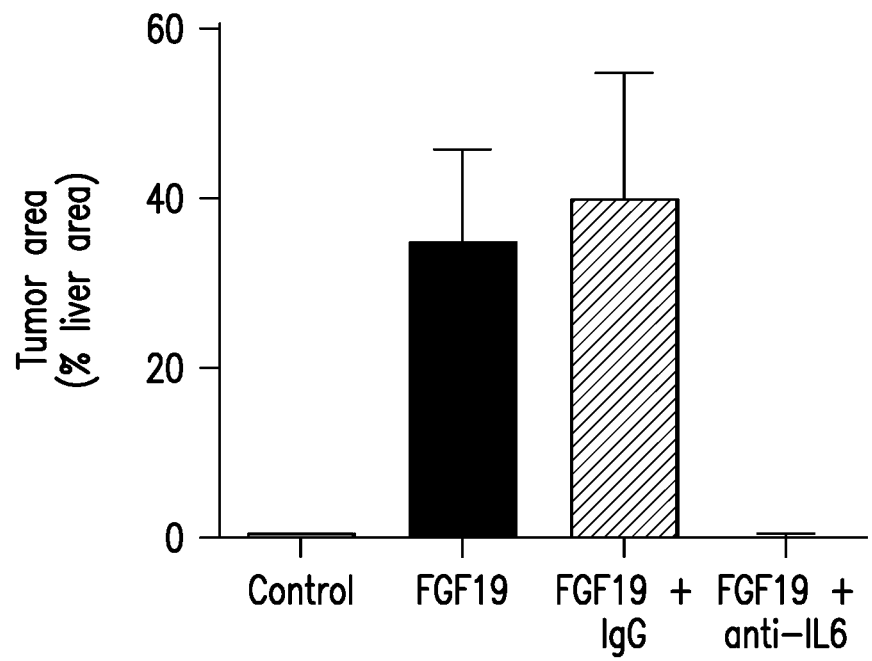
Figure 12J:
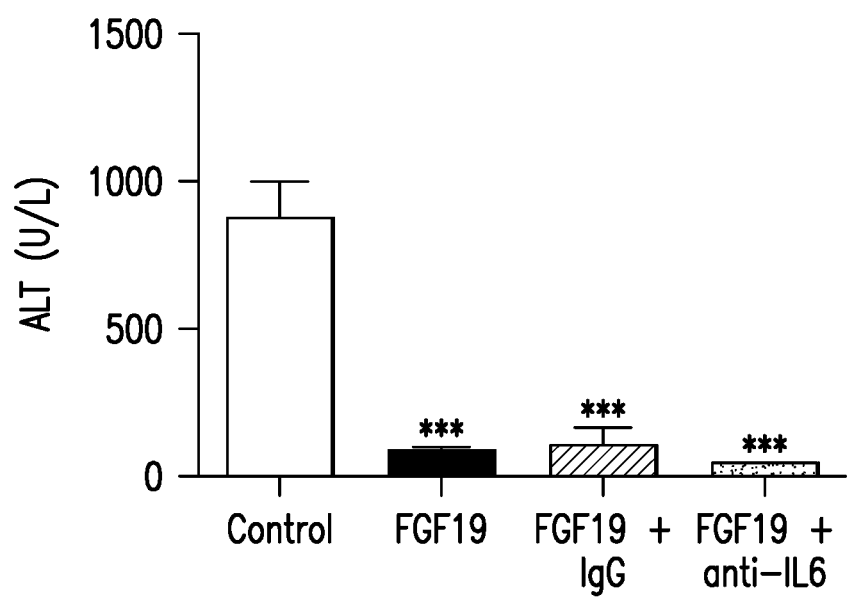
Figure 12K:
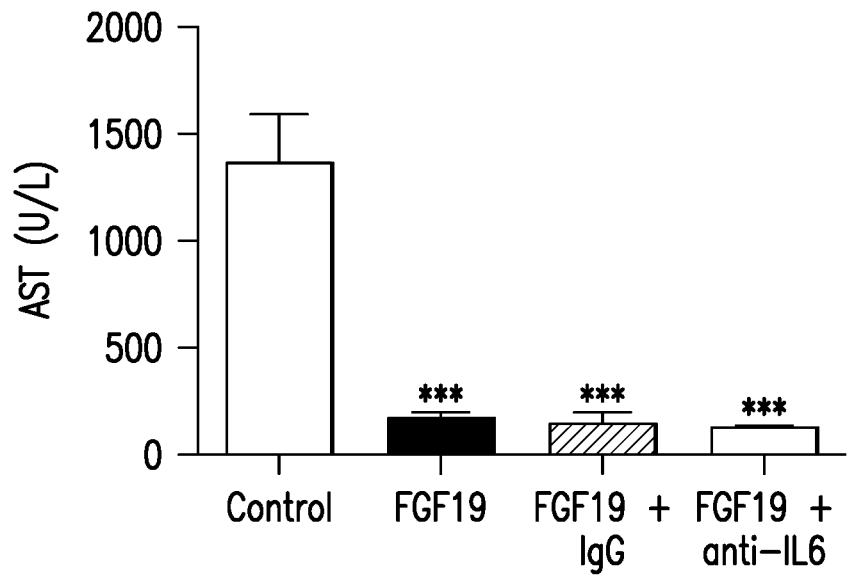
Figure 12L:
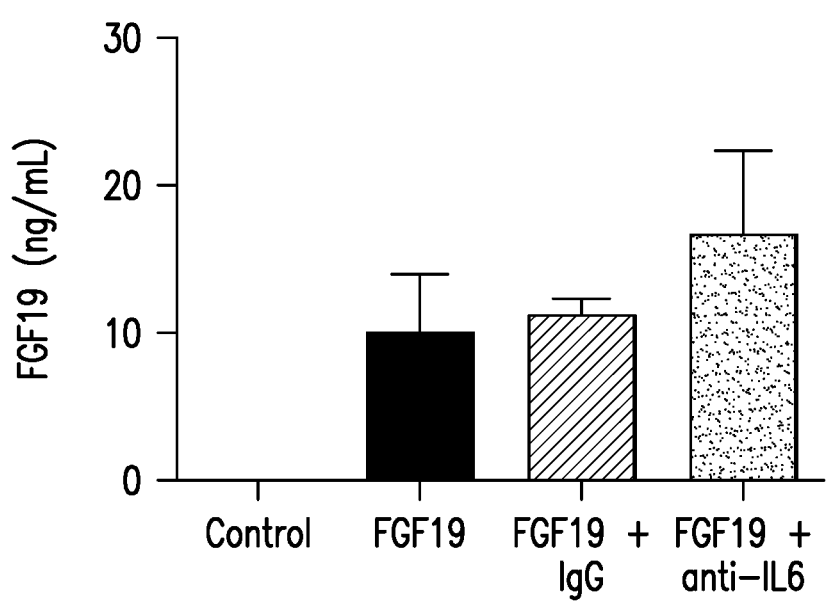

Mdr2$^{-/-}$ mice administrated with AAV-FGF19 exhibited significant improvement in serum liver enzyme levels, with reductions observed for alkaline phosphatase (ALP), alanine aminotransferase (ALT), aspartate aminotransferase (AST) (FIG. 12H). Prolonged expression of FGF19 induced liver tumor formation in these mice (FIG. 7E). Anti-IL-6 antibody treatment (at 10 mg/kg, intraperitoneally once every week, for a total of 10 weekly treatments) was initiated after 14 weeks of continuous FGF19 exposure. FGF19-expressing Mdr2$^{-/-}$ mice treated with anti-IL-6 antibody had livers free of tumors, whereas those treated with isotype control antibodies develop HCC (FIGS. 7E and 12I). Importantly, treatment of Mdr2$^{-/-}$ mice with anti-IL-6 antibody reduced FGF19-mediated hepatocarcinogenicity without altering FGF19's anti-cholestatic effects on lowering serum levels of ALP (FIG. 7F), ALT (FIG. 12J), AST (FIG. 12K), and bile acids (FIG. 7G). Similar circulating FGF19 levels were observed in all groups of mice (FIG. 12L).

Thus, these data demonstrate that inhibition of the IL-6/STAT3 signaling with an endogenous negative regulator SOCS3, a small molecule chemical inhibitor of JAK kinases, or a neutralizing antibody against IL-6 effectively abolished FGF19's pro-tumorigenic activity.

Example 8

Expression of FGF19 and STAT3 Target Genes in Human HCCs

The association between FGF19 expression and STAT3 activation in primary tumors from The Cancer Genome Atlas (TCGA) database, and in formalin-fixed, paraffin-embedded or frozen human HCC samples were examined. The analysis revealed that FGF19 amplification occurs frequently in a variety of human cancers, including hepatocellular carcinomas (7%), esophageal carcinomas (35%), head and neck squamous cell carcinomas (24%), breast invasive carcinomas (16%), and lung squamous cell carcinomas (14%). No mutations or homozygous deletions were detected in the FGF19 gene in the TCGA LIHC (liver hepatocellular carcinomas) data set; one hundred percent of the genetic alterations in FGF19 detected in these tumors were identified as gene amplifications.

Next, the correlation between FGF19 gene copy number and expression level was analyzed. FGF19 mRNA levels correlated with gene copy numbers in human liver cancer, as well as in other cancer types. Compared with normal livers, FGF19 expression was significantly higher in HCC. Similar elevated levels of FGF19 were observed in tumor samples and adjacent non-tumor tissues, resembling results observed in mouse models.

Figure 13:
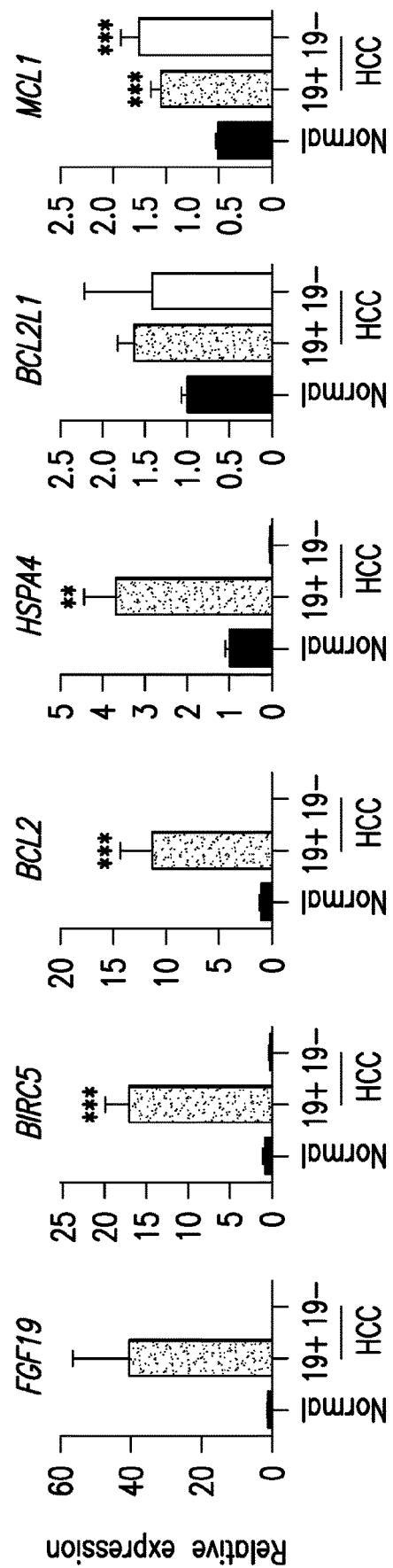
FIG. 13 depicts the upregulation of STAT3 target genes (BIRC5, BCL2, HSPA4, BCL2L1 and MCL1) in FGF19-expressing human HCCs. Quantitative RT-PCR was performed on RNA extracted from frozen FGF19-expressing (19+) human HCC samples (n=5), FGF19-non-expressing (19-) human HCC samples (n=5), or normal livers (n=5). Values are mean±SEM. *P<0.001, P<0.01 by one-way ANOVA.

Further analysis revealed that FGF19 expression is correlated with mRNA levels of STAT3 target genes, such as BIRC5, BCL2, HSPA4 and BCL2L1. In situ hybridization was used to measure FGF19 and BIRC5 mRNA levels in 83 human HCC specimens and 10 normal livers. Notably FGF19 mRNA was undetectable using this technique in any of the normal liver tissues. In contrast, FGF19 mRNA levels were significantly elevated in ten of the formalin-fixed, paraffin-embedded human HCC specimens tested (12%). Moreover, FGF19 and BIRC5 expression levels were concomitantly amplified in all 10 of these tumor samples, further establishing a positive correlation between the expression of FGF19 and BIRC5, a STAT3 target gene, in human HCC. Upregulation of STAT3 target genes, including BIRC5, BCL2, HSPA4, was also confirmed by quantitative RT-PCR analysis in frozen human HCC specimens expressing FGF19, but not in HCC samples lacking FGF19 expression (FIG. 13).

Example 9

Individualized Treatment Decisions for HCC Patients

The following procedures can be taken to determine whether a HCC patient is suitable for an anti-IL-6 antibody or an anti-IL-6 receptor antibody treatment, such as a siltuximab or tocilizumab.

The expression level of FGF19 in the tumor sample can be determined using Real-time quantitative PCR (qRT-PCR) assays. Total RNA from the tumor sample is extracted using RNeasy Mini kit (Qiagen) and treated with DNase I (Thermo Fisher Scientific). Real-time quantitative PCR (qRT-PCR) assays is performed using QuantiTect multiplex qRT-PCR master mix (Qiagen) and premade Taqman gene expression assays (Life Technologies). Samples are loaded into an optical 384-well plate and qRT-PCR is performed in duplicates on QuantStudio 7 Flex Real-Time PCR System (Applied Biosystems). Target gene expression is determined using the comparative threshold cycle (ΔΔCt) method and normalized to the expression of housekeeping genes glyceraldehyde 3-phosphate dehydrogenase (GAPDH) or β-actin.

If the HCC patient is determined to have amplified expression of FGF19, and if the patient is not otherwise prevented from receiving an anti-IL-6 antibody or an anti-IL-6 receptor antibody treatment, such treatment is prescribed.

Particular embodiments of this invention are described herein. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference in its entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

What is claimed is:

1. A method of treating the initiation or progression of a fibroblast growth factor 19 (FGF19)-mediated cancer or tumor without impacting FGF19-mediated bile acid metabolism in a subject in need thereof, comprising, administering to the subject a therapeutically effective amount of an anti-interleukin-6 (anti-IL-6) antibody, wherein the FGF19-mediated cancer or tumor is a liver cancer or tumor.

2. The method of claim 1, wherein the anti-IL-6 antibody is siltuximab, clazakizumab, elsilimomab, or sirukumab.

3. The method of claim 1, wherein the anti-IL-6 antibody is siltuximab, and wherein the dose of the siltuximab (i) is in the range of about 0.1 to 100 mg/kg per day; (ii) is in the range of about 5 to about 25 mg/kg/day; (iii) is about 5 mg/kg per day; (iv) is about 10 mg/kg per day; (v) is about 11 mg/kg per day; or (vi) is about 15 mg/kg per day.

4. The method of claim 1, wherein the anti-IL-6 antibody is siltuximab, and wherein the siltuximab is administered once every 3 or 4 weeks by intravenous infusion.

5. The method of claim 1, wherein the administration treats the cancer or tumor without substantially affecting the metabolic function mediated by FGF19.

6. The method of claim 5, wherein the metabolic function is the ability to regulate bile acid synthesis, glucose metabolism or energy homeostasis.

7. The method of claim 1, wherein the liver cancer or tumor is a hepatocellular carcinoma (HCC).

8. The method of claim 1, wherein the expression level of FGF19 or at least one STAT3 target gene is amplified in the cancer or tumor as compared to a control.

9. The method of claim 8, wherein the at least one STAT3 target gene is BIRC5, BCL2, HSPA4, BCL2L1, or MCL1.

10. The method of claim 8, wherein the expression level of the FGF19 or the at least one STAT target gene is determined by Quantitative Polymerase Chain Reaction (qPCR), Real-Time Polymerase Chain Reaction (RT-PCR), RNA-seq, Microarray, Serial Analysis of Gene Expression (SAGE), MassARRAY technique, or Fluorescence In Situ Hybridization (FISH), an immunohistochemistry (IHC) assay, an immunoblotting (IB) assay, flow cytometry (FACS), or Enzyme-Linked Immunosorbent Assay (ELISA).

11. A method of modulating FGF19 signaling in a liver cancer cell or liver tumor cell, the method comprising contacting the cell with an anti-IL-6 antibody, thereby reducing FGF19-mediated oncogenic signaling without impacting FGF19-mediated bile acid metabolism in the liver cancer cell or liver tumor cell.

* * * * *